US009328122B2

(12) United States Patent
Rong et al.

(10) Patent No.: US 9,328,122 B2
(45) Date of Patent: May 3, 2016

(54) 7-SUBSTITUTED HANFANGICHIN B DERIVATIVE, AND PREPARATION METHOD AND USE THEREOF

(71) Applicant: HANGZHOU BENSHENG PHARMACEUTICAL CO., LTD., Zhejiang (CN)

(72) Inventors: Frank Rong, Zhejiang (CN); Rongzhen Xu, Zhejiang (CN); Hongxi Lai, Fujian (CN); Fuwen Xie, Fujian (CN)

(73) Assignee: HANGZHOU BENSHENG PHARMACEUTICALS CO., LTD., Hangzhou (CN)

( * ) Notice: Subject to any disclaimer, the term of this patent is extended or adjusted under 35 U.S.C. 154(b) by 0 days.

(21) Appl. No.: 14/373,526

(22) PCT Filed: Jan. 21, 2013

(86) PCT No.: PCT/CN2013/070800
§ 371 (c)(1),
(2) Date: Jul. 21, 2014

(87) PCT Pub. No.: WO2013/107428
PCT Pub. Date: Jul. 25, 2013

(65) Prior Publication Data

US 2014/0357647 A1 Dec. 4, 2014

(30) Foreign Application Priority Data

Jan. 21, 2012 (WO) ................ PCT/CN2012/070698

(51) Int. Cl.
*C07D 498/18* (2006.01)
*C07D 491/18* (2006.01)

(52) U.S. Cl.
CPC .................................... *C07D 491/18* (2013.01)

(58) Field of Classification Search
CPC ..................................................... C07D 491/18
USPC .......................................... 540/469; 514/279
See application file for complete search history.

(56) References Cited

FOREIGN PATENT DOCUMENTS

| | | | |
|---|---|---|---|
| CN | 1293196 | A | 5/2001 |
| CN | 1511527 | A | 7/2004 |
| CN | 101371839 | A | 2/2009 |
| JP | S62-207216 | A | 9/1987 |
| JP | H02-134382 | A | 5/1990 |

OTHER PUBLICATIONS

Chen et al. Journal of Biological Chemistry (1935), 109, 681-5). Abstract.*
Kawashima et al. (General Pharmacology (1990), 21(3), 343-7). Abstract.*
Kawashima et al. (General Pharmacology (1991), 22(1), 165-168). Abstract.*
International Search Report with Written Opinion corresponding to International Patent Application No. PCT/ CN2013/070800, mailed Apr. 25, 2013—search results only.
Kawashima (1990) "Structure and hypotensive activity relationships of tetrandrine derivatives in stroke-prone spontaneously hypertensive rats," Gen Pharmacol. 21:343-347.
Ogino et al., "Studies on the Crude Drug Containing Angiotensin I Converting Enyme Inhibitors (III) On the Activity of the Principles in Stephania tetrandra S. Moore and their Derivertives" Natural Medicines 1998, 52(2), p. 172-178; English abstract.
Kawashima (1991) "Antihypertensive effect of synthetic tetrandrine derivatives in SHR rats," Gen Pharmacol. 22 (1):165-168.

* cited by examiner

*Primary Examiner* — Bruck Kifle
(74) *Attorney, Agent, or Firm* — Lathrop & Gage LLP; Brian C. Trinque; Benjamin D. Heuberger

(57) ABSTRACT

The present invention belongs to the field of natural medicine and pharmaceutical chemistry and specifically relates to novel 7-substituted fangchinoline derivatives of formula (I) and a pharmaceutically acceptable adduct, complex and salt thereof, to a process for the preparation of these compounds, pharmaceutical compositions containing such compounds and their use in preparing antineoplastic medicaments.

I

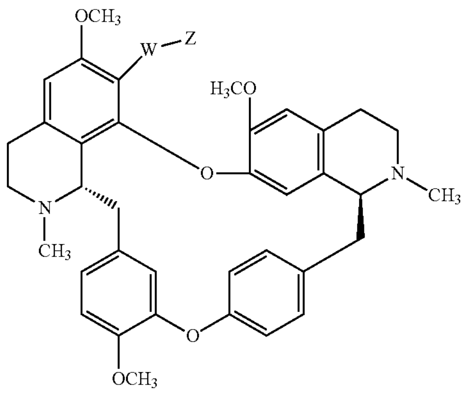

27 Claims, 5 Drawing Sheets

7-SUBSTITUTED HANFANGICHIN B DERIVATIVE, AND PREPARATION METHOD AND USE THEREOF

RELATED APPLICATIONS

This application is a 35 U.S.C. §371 filing of International Application No. PCT/CN2013/070800, filed Jan. 21, 2013, which claims priority to International Application No. PCT/CN2012/070698, filed Jan. 21, 2012, each of which is incorporated herein by reference in its entirety.

TECHNICAL FIELD

The present invention belongs to the field of natural medicine and pharmaceutical chemistry and relates to novel fangchinoline derivatives, in particular 7-substituted fangchinoline derivatives, to a process for the preparation of these compounds, compositions containing such compounds and their use in preparing antineoplastic medicaments.

BACKGROUND OF THE INVENTION

Fangchinoline, or FAN (also known as Hanfangchin B), is a bisbenzylisoquinoline alkaloid extracted from the root of the Chinese herb fangji powder. Fangchinoline is naturally present in the root of fangji family plant *Stephania tetrandra* S. Moore, the root of *Cyclea peltata* Diels and the root and rootstock of *thalictrum dichocarpum* sutchuenense. Fangchinoline is a natural calcium antagonist and has remarkable therapeutic effects on many diseases. For example, it has broad-spectrum anti-inflammatory and antibacterial effect, anti-hypertension effect, anti-diabetic effect, anti-hepatic fibrosis effect, and protective effect on brain cells. Recent studies have found that it also has significant anti-tumor effect, such as the inhibiting effect on W-256, Ehrlich's ascites carcinoma, and S-45, has inhibiting effect on KB cells and Hela cells, and exhibits strong inhibiting effect on human transplanted liver cancer 7402 and 7405 cell lines.

It is reported that fangchinoline exhibits inhibition on human colon cancer cell line LoVo. In the experiment, nude mice bearing the tumor are subjected to successive administration for 60 days. The results show that, as compared with the control group, the tumor in the administered group remarkably shrinks and grows slowly, and the microvessel density is significantly lower. In addition, during the administration, the mice do not exhibit adverse reactions. This demonstrates that fangchinoline has tumor inhibiting effect in vivo with minimal side effects (Zhenjun Wang et al., Use of fangchinolin in vascularization inhibiting medicine [P]. CN1511528A. 2004).

Changdong Wang et al. studied the inhibition of fangchinoline on human prostate cancer cell PC3. The results showed that the inhibition of fangchinoline on the PC3 cell is dose and time dependent. The studies on the cell cycle process indicated that the inhibition of fangchinoline on the PC3 cell is related to the increase of cells in G1/S phase. In addition, fangchinoline exhibits in vivo antitumor activity by diminishing the tumor volume and promoting the apoptosis and exhibits inhibition on the transplanted tumor PC3 in nude mice (Changdong Wang, et al. Fangchinoline induced G1/S arrest by modulating expression of p27, PCNA, and cyclin D in human prostate carcinoma cancer PC3 cells and tumor xenograft[1*]. J. Biosci. Biotechnol. Biochem.* 2010, 74(3):488-493).

Yalin Tang et al. studied the combination of G-quadruplex DNA with fangchinoline to improve the stability of G-quadruplex, thereby reducing the cell proliferation and promoting apoptosis. The experimental results for in vitro antitumor cell proliferation indicate that G-quadruplex DNA, after its combination with fangchinoline, exhibits good inhibiting effect on human leukemia cell line HL-60, human gastric cancer cell line BGC-823, human liver cancer cell line Bel-7402 and human nasopharyngeal cancer cell line KB (Yalin Tang et al., Novel use of bisbenzylisoquinoline alkaloids [P]. CN 101371839A. 2009).

Up to now, there have been few reports on the structural modification and activity of fangchinoline. Recent years have witnessed studies by Fengpeng Wang et al. on the structural modification of fangchinoline, but reports on the related pharmacodynamics activity data have not yet been seen (Fengpeng Wang et al., Dibenzylisoquinoline alkaloids and its preparing process and medical composition [P]. CN 1293196A. 2001).

The present invention conducts structural modification of fangchinoline at its 7'-position hydroxyl group, determines the antitumor activity thereof and discovers that a portion of the novel compounds exhibit significantly improved antitumor activity.

SUMMARY OF THE INVENTION

One object of the present invention is to provide novel 7-substituted fangchinoline derivatives particularly of formula (I), or a pharmaceutically acceptable salt thereof

I

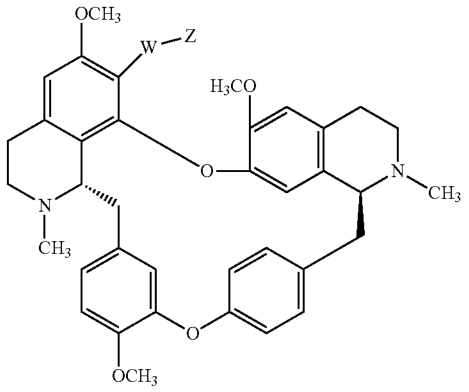

wherein

W is —$OCHR_1$—, —$OSO_2$—, or —OC(O)—;

Z is selected from the group consisting of H, $C_1$-$C_6$ alkyl optionally substituted with a substituent, $C_2$-$C_6$ alkenyl optionally substituted with a substituent, $C_3$-$C_7$ cycloalkyl or cycloalkenyl optionally substituted with a substituent, heterocyclyl optionally substituted with a substituent, aryl or heteroaryl optionally substituted with a substituent, and $R_2R_3NCH_2CH(OH)$—, or Z and $R_1$, together with the carbon atom to which they are attached, form $C_3$-$C_7$ cycloalkyl optionally substituted with a substituent;

$R_1$ is H, or $R_1$ and Z, together with the carbon atom to which they are attached, form $C_3$-$C_7$ cycloalkyl optionally substituted with a substituent;

$R_2$ and $R_3$ are independently H, $C_1$-$C_6$ alkyl or $C_2$-$C_6$ alkenyl optionally substituted with hydroxyl, $C_1$-$C_6$ alkoxy, halogen, $C_3$-$C_7$ cycloalkyl or cycloalkenyl, aryl or heteroaryl, or $R_2$ and $R_3$, together with the nitrogen atom to which they are attached, form 3-7 membered nitrogen-containing heterocycle; said nitrogen-containing heterocycle optionally comprises an additional heteroatom selected from oxygen, sulfur and nitrogen and is optionally substituted with a substituent;

wherein said substitutent is selected from the group consisting of halogen, amino, $C_1$-$C_6$ alkyl amino, di($C_1$-$C_6$ alkyl) amino, nitro, cyano, hydroxyl, $C_1$-$C_6$ alkoxy, $C_1$-$C_6$ haloalkoxy, thiol and $C_1$-$C_6$ alkylthio; for said aryl, heteroaryl, $C_3$-$C_7$ cycloalkyl or cycloalkenyl, heterocyclyl and nitrogen-containing heterocyclyl, said substitutent is also selected from the group consisting of $C_1$-$C_6$ alkyl, hydroxyl $C_1$-$C_6$ alkyl and $C_1$-$C_6$ haloalkyl;

wherein when W is —$OCH_2$—, Z is not ethyl, n-propyl or isopropyl; when W is —OC(O)—, Z is not ethyl or propyl.

The second object of the present invention is to provide a process for preparing the 7-substituted fangchinoline derivative of formula (I) of the present invention:

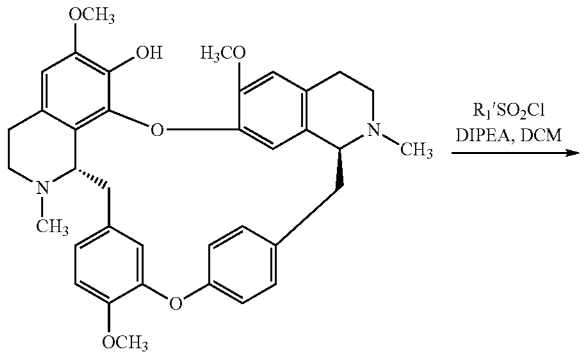

FAN

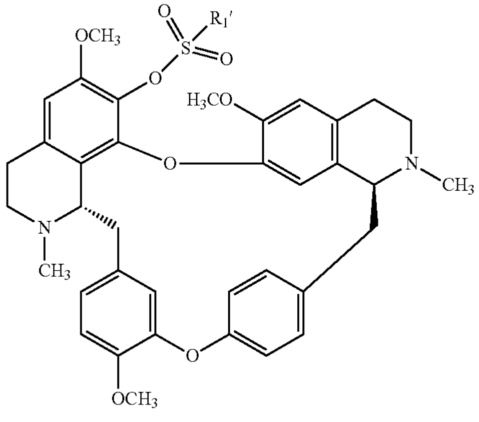

I-1 the 7-substituted fangchinoline derivative of formula (I-1) is produced by reacting fangchinoline (FAN) with a corresponding alkyl or aromatic sulfonyl chloride ($R_1$'$SO_2Cl$) in the presence of an alkali at room temperature, wherein $R_1$' is selected from the group consisting of H, $C_1$-$C_6$ alkyl optionally substituted with a substituent, $C_2$-$C_6$ alkenyl optionally substituted with a substituent, $C_3$-$C_7$ cycloalkyl or cycloalkenyl optionally substituted with a substituent, heterocyclyl optionally substituted with a substituent, and aryl or heteroaryl optionally substituted with a substituent, in which said substituent is as defined in claim 1;

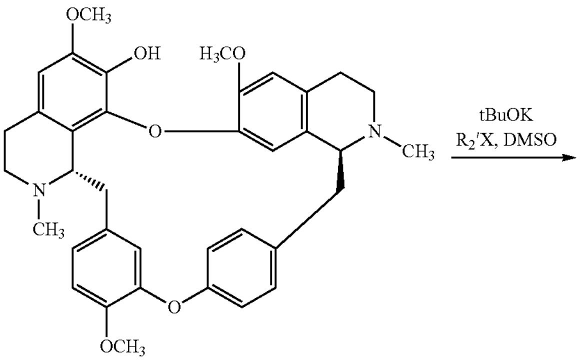

FAN

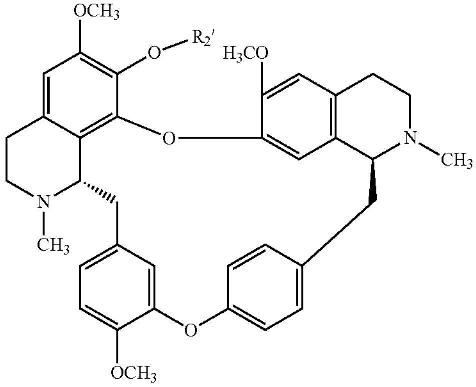

I-2 the 7-substituted fangchinoline derivative of formula (I-2) is produced by reacting fangchinoline (FAN) firstly with a strong alkali and then with a corresponding halohydrocarbon ($R_2$'X) in the presence of an alkali at room temperature or under heating conditions, wherein $R_2$' is $CHR_1Z$, in which $R_1$ and Z are as defined in claim 1 without Z being $R_2R_3NCH_2CH(OH)$—;

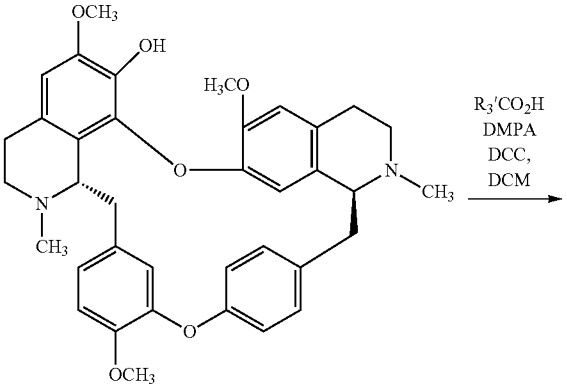

FAN

-continued

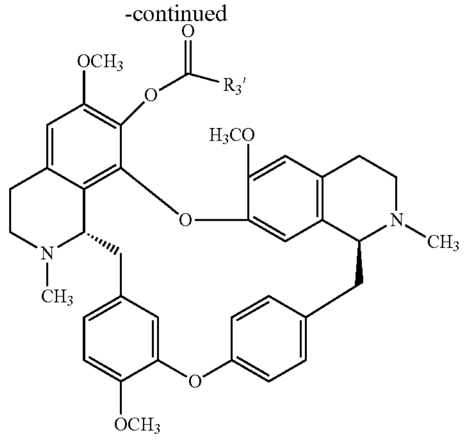

I-3 the 7-substituted fangchinoline derivative of formula (I-3) is produced by reacting fangchinoline (FAN) with a corresponding organic acid ($R_3'CO_2H$) in the presence of a condensating agent and an alkali at room temperature, wherein $R_3'$ is $C_1$-$C_6$ alkyl optionally substituted with a substituent, $C_2$-$C_6$ alkenyl optionally substituted with a substituent, $C_3$-$C_7$ cycloalkyl or cycloalkenyl optionally substituted with a substituent, heterocyclyl optionally substituted with a substituent, or aryl or heteroaryl optionally substituted with a substituent, in which the substituent is as defined in claim 1;

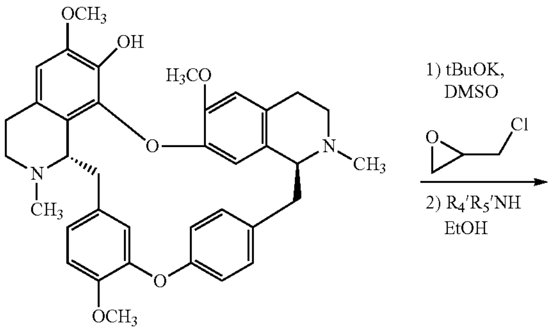

FAN

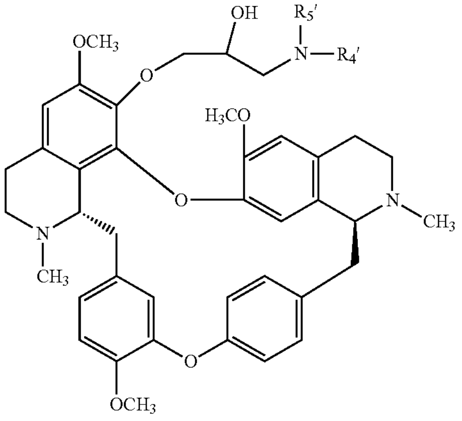

I-4 the 7-substituted fangchinoline derivative of formula (I-4) can be produced by a two-step reaction: firstly reacting fangchinoline with potassium tert-butoxide and chloromethyl propylene oxide to give an intermediate, and then reacting this intermediate with a corresponding organic amine to give the product, wherein $R_4'$ and $R_5'$ are defined as $R_2$ and $R_3$ in claim 1.

The third object of the present invention is to provide a pharmaceutical composition comprising the compound of the present invention. Said pharmaceutical composition comprises at least one compound of the present invention and optionally a pharmaceutically acceptable excipient.

The fourth object of the present invention is to provide the use of the compound of the present invention or a pharmaceutical composition comprising said compound in the manufacture of a medicament, in particular an antitumor medicament. Correspondingly, the present invention provides a method for treating a subject suffering from tumor, comprising administering to the subject in need thereof an effective amount of at least one compound of the present invention. Said tumor is particularly selected from leukemia, multiple myeloma, lymphoma, liver cancer, gastric cancer, breast cancer, cholangiocellular carcinoma, pancreatic cancer, lung cancer, colorectal cancer, osteosarcoma, melanoma, human cervical cancer, glioma, nasopharyngeal carcinoma, laryngeal carcinoma, esophageal cancer, middle ear tumor, prostate cancer and the like.

The present invention also relates to the compounds of the present invention used for treating a tumor.

DETAILED DESCRIPTION OF THE INVENTION

Figure 1:
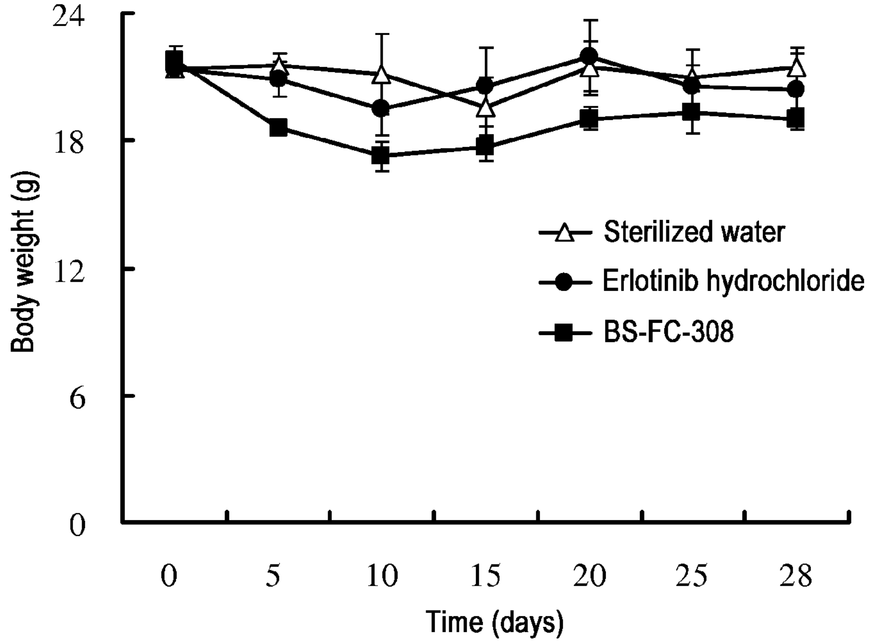
FIG. 1 is a curve showing the dynamic effect of BS-FC-308 on body weight of nude mice.

The present invention provides a novel fangchinoline derivative with antitumor activity, in particular a 7-substituted fangchinoline derivative of formula (I), or a pharmaceutically acceptable salt thereof,

I

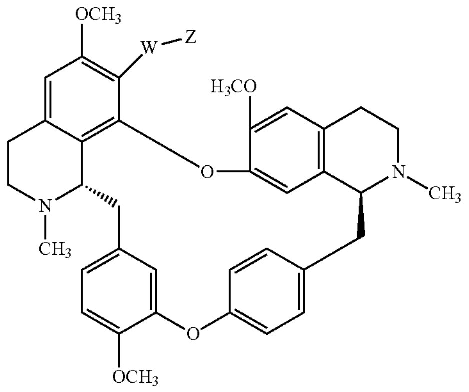

wherein

W is —$OCHR_1$—, —$OSO_2$—, or —OC(O)—;

Z is selected from the group consisting of H, $C_1$-$C_6$ alkyl optionally substituted with a substituent, $C_2$-$C_6$ alkenyl optionally substituted with a substituent, $C_3$-$C_7$ cycloalkyl or cycloalkenyl optionally substituted with a substituent, heterocyclyl optionally substituted with a substituent, aryl or heteroaryl optionally substituted with a substituent, and $R_2R_3NCH_2CH(OH)$—, or Z and $R_1$, together with the carbon atom to which they are attached, form $C_3$-$C_7$ cycloalkyl optionally substituted with a substituent;

$R_1$ is H, or $R_1$ and Z, together with the carbon atom to which they are attached, form $C_3$-$C_7$ cycloalkyl optionally substituted with a substituent;

$R_2$ and $R_3$ are independently H, $C_1$-$C_6$ alkyl or $C_2$-$C_6$ alkenyl optionally substituted with hydroxyl, $C_1$-$C_6$ alkoxy, halogen, $C_3$-$C_7$ cycloalkyl or cycloalkenyl, aryl or heteroaryl, or $R_2$ and $R_3$, together with the nitrogen atom to which they are attached, form 3-7 membered nitrogen-containing heterocycle; said nitrogen-containing heterocycle optionally comprises an additional heteroatom selected from oxygen, sulfur and nitrogen and is optionally substituted with a substituent;

wherein said substitutent is selected from the group consisting of halogen, amino, $C_1$-$C_6$ alkyl amino, di($C_1$-$C_6$ alkyl) amino, nitro, cyano, hydroxyl, $C_1$-$C_6$ alkoxy, $C_1$-$C_6$ haloalkoxy, thiol and $C_1$-$C_6$ alkylthio; for said aryl, heteroaryl, $C_3$-$C_7$ cycloalkyl or cycloalkenyl, heterocyclyl and nitrogen-containing heterocyclyl, said substitutent is also selected from the group consisting of $C_1$-$C_6$ alkyl, hydroxyl $C_1$-$C_6$ alkyl and $C_1$-$C_6$ haloalkyl;

wherein when W is —$OCH_2$—, Z is not ethyl, n-propyl or isopropyl; when W is —OC(O)—, Z is not ethyl or propyl.

When W is —$OSO_2$—, the compound of formula (I) of the present invention corresponds to formula (I-1)

I-1

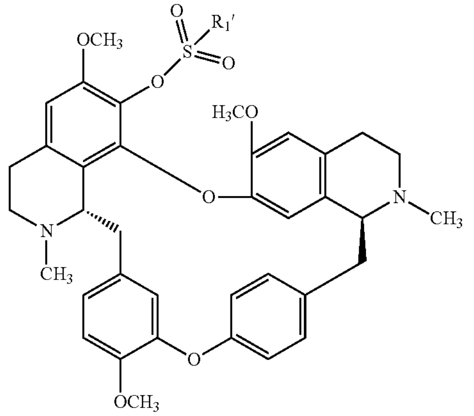

wherein Z=$R_1$', which is selected from the group consisting of H, $C_1$-$C_6$ alkyl optionally substituted with a substituent, $C_2$-$C_6$ alkenyl optionally substituted with a substituent, $C_3$-$C_7$ cycloalkyl or cycloalkenyl optionally substituted with a substituent, a heterocyclyl optionally substituted with a substituent, an aryl or a heteroaryl optionally substituted with a substituent; wherein said substitutent is as defined in the above formula (I).

When W is —$OCHR_1$—, $R_1$ and Z are defined as in the above formula (I) but Z is not $R_2R_3NCH_2CH(OH)$—, the compound of formula (I) of the present invention is of formula (I-2),

I-2

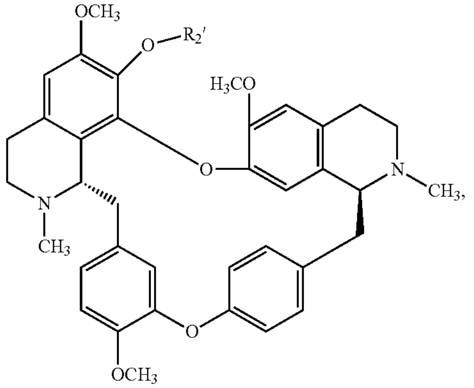

wherein $R_2$' is —$CHR_1$Z.

When W is —OC(O)—, the compound of formula (I) of the present invention is of formula (I-3),

I-3

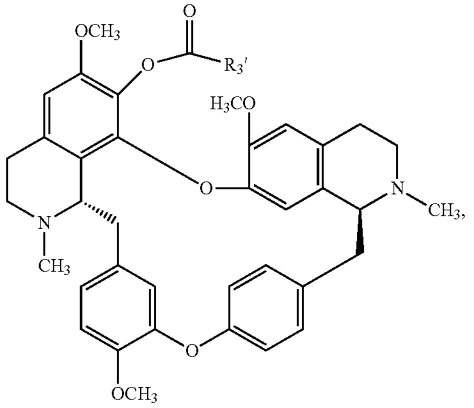

wherein $R_3'$=Z, which is $C_1$-$C_6$ alkyl optionally substituted with a substituent, $C_2$-$C_6$ alkenyl optionally substituted with a substituent, $C_3$-$C_7$ cycloalkyl or cycloalkenyl optionally substituted with a substituent, heterocyclyl optionally substituted with a substituent, aryl or heteroaryl optionally substituted with a substituent; wherein said substituent is as defined in the above formula (I).

When W is —$OCH_2$— and Z is $R_2R_3NCH_2CH(OH)$—, the compound of formula (I) of the present invention is of formula (I-4),

I-4

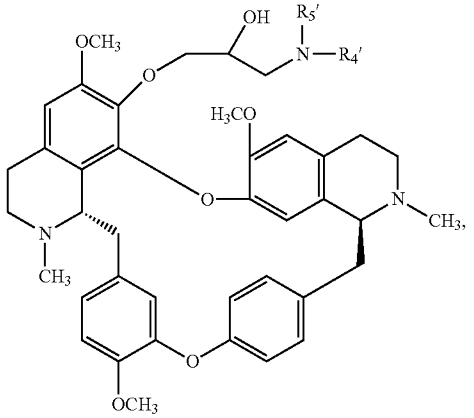

wherein $R_4'$ and $R_5'$ are defined as $R_2$ and $R_3$ in the above formula (I).

According to the first embodiment, the present invention relates to a 7-substituted fangchinoline derivative of formula (I) or a pharmaceutically acceptable salt thereof, wherein W is —$OSO_2$—; Z is selected from the group consisting of H, $C_1$-$C_6$ alkyl optionally substituted with a substituent, $C_2$-$C_6$ alkenyl optionally substituted with a substituent, $C_3$-$C_7$ cycloalkyl or cycloalkenyl optionally substituted with a substituent, heterocyclyl optionally substituted with a substituent, and aryl or heteroaryl optionally substituted with a substituent; wherein said substitutent is selected from the group consisting of halogen, amino, $C_1$-$C_6$ alkyl amino, di($C_1$-$C_6$ alkyl)amino, nitro, cyano, hydroxyl, $C_1$-$C_6$ alkoxy, $C_1$-$C_6$ haloalkoxy, thiol and $C_1$-$C_6$ alkylthio; for said aryl, heteroaryl, $C_3$-$C_7$ cycloalkyl or cycloalkenyl, and heterocyclyl, said substitutent is also selected from the group consisting of $C_1$-$C_6$ alkyl, hydroxyl $C_1$-$C_6$ alkyl and $C_1$-$C_6$ halo alkyl.

In the above embodiment, preferably, Z is selected from the group consisting of $C_1$-$C_6$ alkyl aryl optionally substituted with a substituent, and aryl or heteroaryl optionally substituted with a substituent; wherein said substituent is selected from the group consisting of halogen, amino, $C_1$-$C_6$ alkyl amino, di($C_1$-$C_6$ alkyl)amino, nitro, cyano, hydroxyl, $C_1$-$C_6$ alkoxy, $C_1$-$C_6$ haloalkoxy, thiol, and $C_1$-$C_6$ alkylthio; for said aryl and heteroaryl, said substituent is also selected from $C_1$-$C_6$ alkyl, hydroxyl $C_1$-$C_6$ alkyl and $C_1$-$C_6$ haloalkyl.

In the above embodiment, more preferably, Z is selected from the group consisting of $C_1$-$C_6$ alkyl optionally substituted with a substituent, phenyl optionally substituted with a substituent; wherein said substituent is selected from the group consisting of halogen, $C_1$-$C_6$ alkoxy and $C_1$-$C_6$ haloalkoxy; said phenyl can also be substituted with a substituent selected from the group consisting of $C_1$-$C_6$ alkyl, hydroxyl $C_1$-$C_6$ alkyl and $C_1$-$C_6$ haloalkyl.

In the above embodiment, most preferably, Z is phenyl optionally substituted with $C_1$-$C_6$ alkyl.

In the second embodiment, the present invention relates to a 7-substituted fangchinoline derivative of formula (I) or a pharmaceutically acceptable salt thereof, wherein W is $OCH_2$—; Z is selected from the group consisting of $C_1$-$C_6$ alkyl optionally substituted with a substituent, $C_2$-$C_6$ alkenyl optionally substituted with a substituent, $C_3$-$C_7$ cycloalkyl or cycloalkenyl optionally substituted with a substituent, heterocyclyl optionally substituted with a substituent, aryl or heteroaryl optionally substituted with a substituent, $R_2R_3NCH_2CH(OH)$—; $R_2$ and $R_3$ are independently H, $C_1$-$C_6$ alkyl, or $C_2$-$C_6$ alkenyl, which are optionally substituted with hydroxyl, $C_1$-$C_6$ alkoxy, halogen, $C_3$-$C_7$ cycloalkyl or cycloalkenyl, aryl or heteroaryl, or $R_2$ and $R_3$ together with the nitrogen atom to which they are attached form 3-7 membered nitrogen-containing heterocycle; said nitrogen-containing heterocycle optionally comprises an additional heteroatom selected from the group consisting of oxygen, sulfur and nitrogen and is optionally substituted with a substituent; wherein said substitutent is selected from the group consisting of halogen, amino, $C_1$-$C_6$ alkyl amino, di($C_1$-$C_6$ alkyl) amino, nitro, cyano, hydroxyl, $C_1$-$C_6$ alkoxy, $C_1$-$C_6$ haloalkoxy, thiol and $C_1$-$C_6$ alkylthio; for said aryl, heteroaryl, $C_3$-$C_7$ cycloalkyl or cycloalkenyl, heterocyclyl and nitrogen-containing heterocyclyl, said substitutent is also selected from the group consisting of $C_1$-$C_6$ alkyl, hydroxyl $C_1$-$C_6$ alkyl and $C_1$-$C_6$ haloalkyl.

In the above embodiment, preferably, Z is aryl or heteroaryl optionally substituted with a substituent; wherein said substituent is selected from the group consisting of halogen, amino, $C_1$-$C_6$ alkyl amino, di($C_1$-$C_6$ alkyl)amino, nitro, cyano, hydroxyl, $C_1$-$C_6$ alkoxy, $C_1$-$C_6$ haloalkoxy, thiol, $C_1$-$C_6$ alkylthio, $C_1$-$C_6$ alkyl, hydroxyl $C_1$-$C_6$ alkyl and $C_1$-$C_6$ haloalkyl.

In the above embodiment, more preferably, Z is phenyl optionally substituted with a substituent selected from halogen, $C_1$-$C_6$ alkyl, $C_1$-$C_6$ haloalkyl, $C_1$-$C_6$ alkoxy, hydroxyl $C_1$-$C_6$ alkyl and $C_1$-$C_6$ halo alkoxyl.

In the second embodiment, preferably, Z is $R_2R_3NCH_2CH(OH)$—; $R_2$ and $R_3$ are independently H, $C_1$-$C_6$ alkyl or $C_2$-$C_6$ alkenyl optionally substituted with hydroxyl, $C_1$-$C_6$ alkoxy, halogen, $C_3$-$C_7$ cycloalkyl or cycloalkenyl, aryl or heteroaryl, or $R_2$ and $R_3$ together with the nitrogen atom to which they are attached form 3-7 membered nitrogen-containing heterocycle; said nitrogen-containing heterocycle optionally comprises an additional heteroatom selected from the group consisting of oxygen, sulfur and nitrogen and is optionally substituted with a substituent; wherein said substitutent is selected from the group consisting of halogen, amino, $C_1$-$C_6$ alkyl amino, di($C_1$-$C_6$ alkyl)amino, nitro, cyano, hydroxyl, $C_1$-$C_6$ alkoxy, $C_1$-$C_6$ haloalkoxy, thiol, $C_1$-$C_6$ alkylthio, $C_1$-$C_6$ alkyl, hydroxyl $C_1$-$C_6$ alkyl and $C_1$-$C_6$ haloalkyl.

In the above preferred embodiments, preferably, said nitrogen-containing heterocycle is piperidinyl, piperazinyl, morpholinyl, thiazinyl, pyrrolidinyl, oxazolidinyl or thiazolidyl, the substituent being optionally substituted with a substituent selected from the group consisting of halogen, amino, $C_1$-$C_6$ alkyl amino, di($C_1$-$C_6$ alkyl) amino, nitro, cyano, hydroxyl, $C_1$-$C_6$ alkoxy, $C_1$-$C_6$ haloalkoxy, thiol, $C_1$-$C_6$ alkylthio, $C_1$-$C_6$ alkyl, hydroxyl $C_1$-$C_6$ alkyl and $C_1$-$C_6$ haloalkyl; more preferably, said nitrogen-containing heterocycle is piperidinyl optionally substituted with $C_1$-$C_6$ alkyl, thiazinyl optionally substituted with $C_1$-$C_6$ alkyl, piperazinyl optionally substituted with N-cyano.

In the above preferred embodiments, preferably, said $R_2$ and $R_3$ are independently H, methyl, ethyl, hydroxyethyl, cyclopropylmethyl, allyl, methoxypropyl, or furfuryl.

In the second embodiment above, preferably, Z is $C_2$-$C_6$ alkenyl or $C_3$-$C_7$ cycloalkyl or cycloalkenyl; more preferably, Z is vinyl, 1-methylvinyl or cyclopropyl.

In the third embodiment, the present invention relates to the 7-substituted fangchinoline derivative of formula (I) or a pharmaceutically acceptable salt thereof, wherein W is —OCHR$_1$—, Z and R$_1$ together with the carbon atom to which they are attached form $C_3$-$C_7$ cycloalkyl optionally substituted with a substituent, wherein said substituent is selected from the group consisting of halogen, amino, $C_1$-$C_6$ alkyl amino, di($C_1$-$C_6$ alkyl)amino, nitro, cyano, hydroxyl, $C_1$-$C_6$ alkoxy, $C_1$-$C_6$ haloalkoxy, thiol, $C_1$-$C_6$ alkylthio, $C_1$-$C_6$ alkyl, hydroxyl $C_1$-$C_6$ alkyl and $C_1$-$C_6$ haloalkyl. Preferably, Z and R$_1$ together with the carbon atom to which they are attached form a cyclopentyl or cyclohexyl.

In the fourth embodiment, the present invention relates to the 7-substituted fangchinoline derivative of formula (I) or a pharmaceutically acceptable salt thereof, wherein W is —OC(O)—; Z is selected from the group consisting of $C_1$-$C_6$ alkyl optionally substituted with a substituent, $C_2$-$C_6$ alkenyl optionally substituted with a substituent, $C_3$-$C_7$ cycloalkyl or cycloalkenyl optionally substituted with a substituent, heterocyclyl optionally substituted with a substituent, and aryl or heteroaryl optionally substituted with a substituent;

wherein said substituent is selected from the group consisting of halogen, amino, $C_1$-$C_6$ alkyl amino, di($C_1$-$C_6$ alkyl)amino, nitro, cyano, hydroxyl, $C_1$-$C_6$ alkoxy, $C_1$-$C_6$ haloalkoxy, thiol and $C_1$-$C_6$ alkylthio; for said aryl, heteroaryl, $C_3$-$C_7$ cycloalkyl or cycloalkenyl and heterocyclyl, said substituent is also selected from the group consisting of $C_1$-$C_6$ alkyl, hydroxyl $C_1$-$C_6$ alkyl and $C_1$-$C_6$ halo alkyl.

In the fourth embodiment above, preferably, Z is phenyl, pyridyl, or pyridazinyl, each of which is optionally substituted with a substituent selected from the group consisting of methyl, ethyl, isopropyl, amino, methylamino, dimethylamino, diethylamino, methoxyl, trifluoromethoxy and halogen.

Some of the 7-substituted fangchinoline derivatives of the present invention are shown below. It is observed by measurements that they exhibit an antitumor activity superior to or at least comparable to that of fangchinoline. These examples are only intended to further illustrate the present invention but not to make any restriction over the scope of the present invention.

BS-FC-102

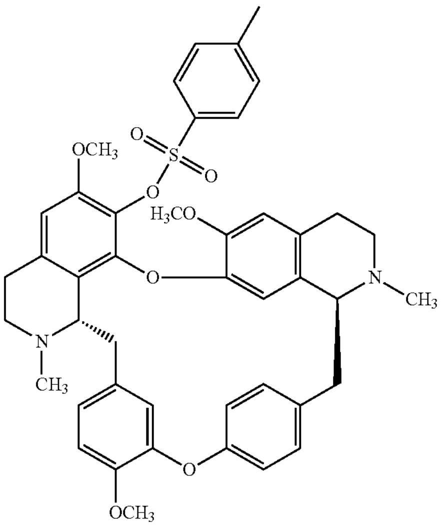

-continued

BS-FC-104

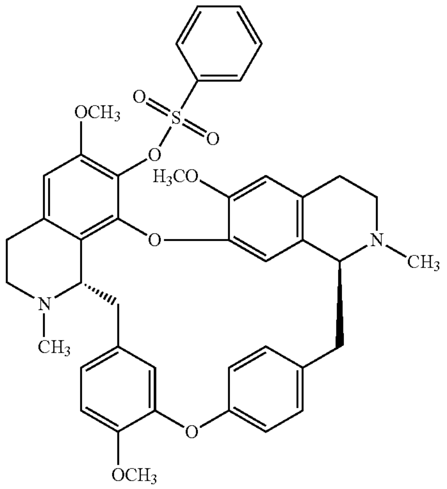

BS-FC-105

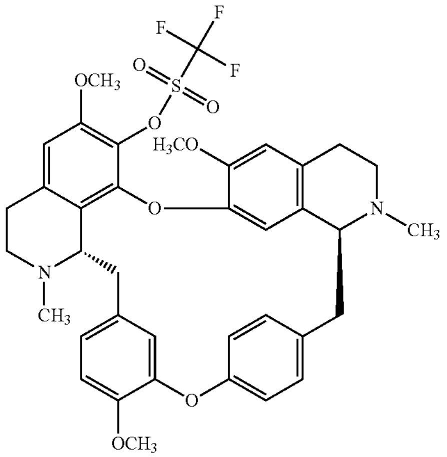

BS-FC-201

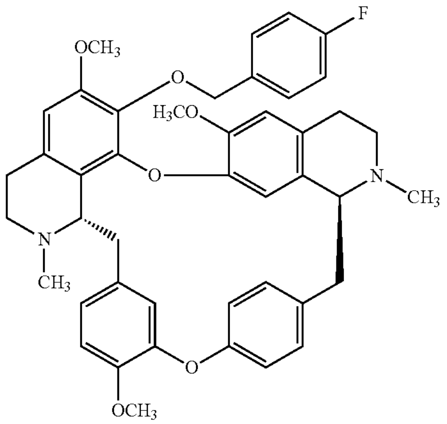

BS-FC-202
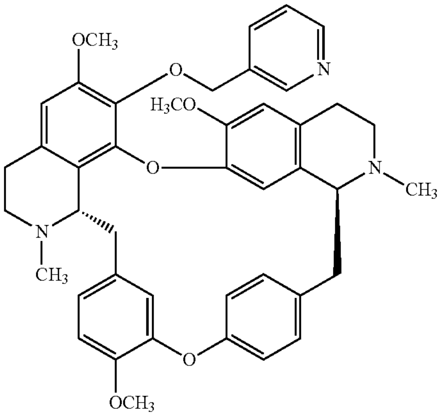
BS-FC-203
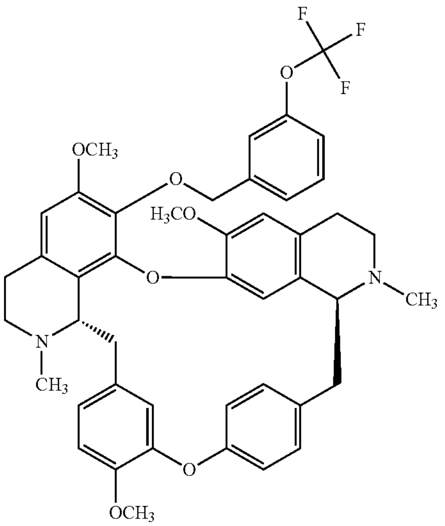
BS-FC-204
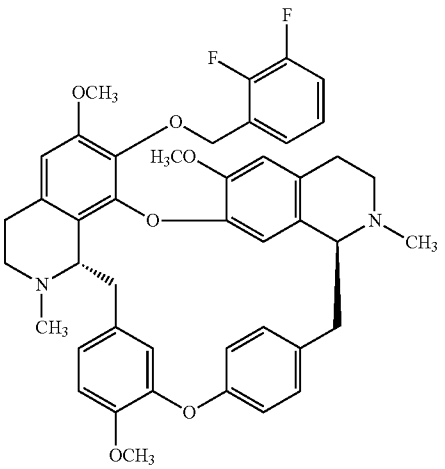
BS-FC-205
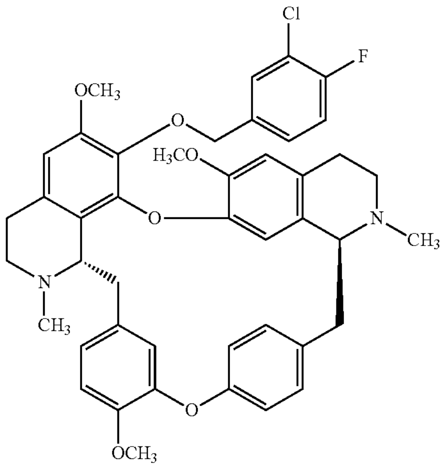
BS-FC-206
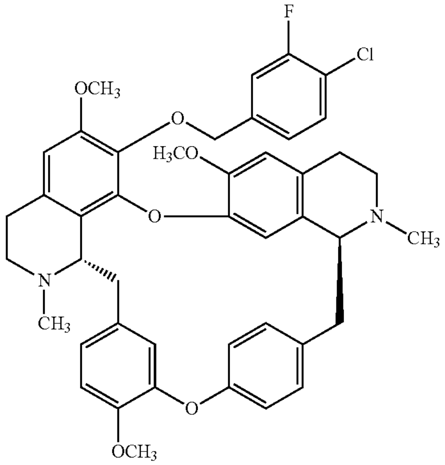
BS-FC-208
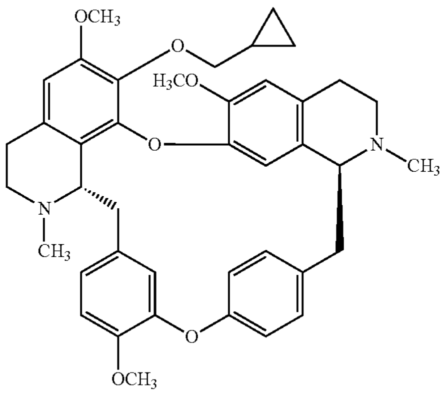

-continued
BS-FC-213
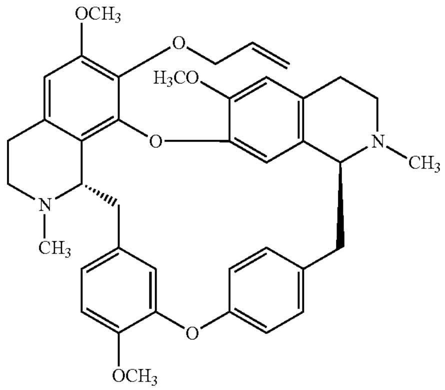
BS-FC-215
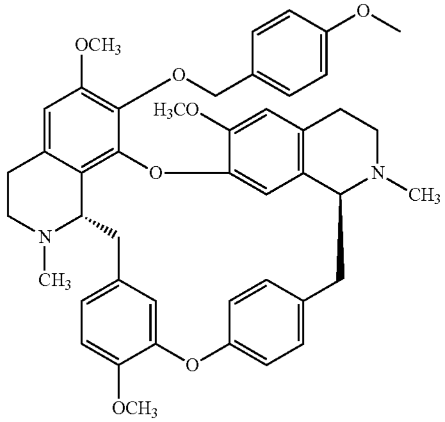
BS-FC-216
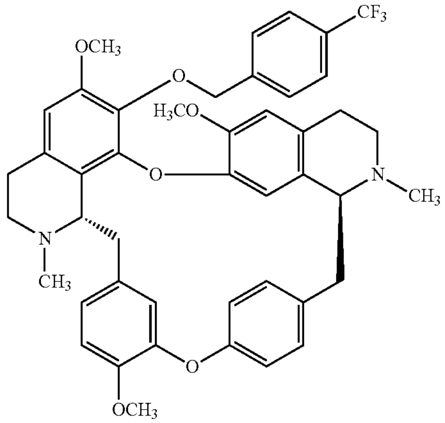
-continued
BS-FC-217
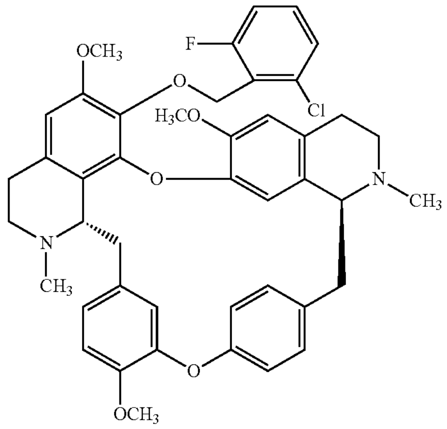
BS-FC-220
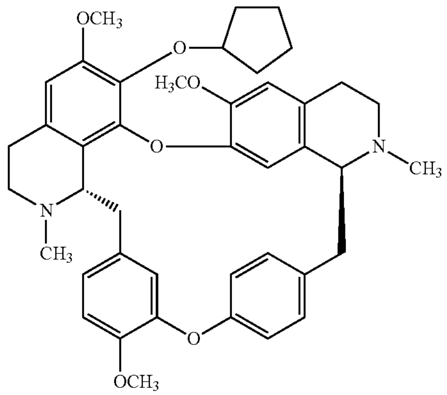
BS-FC-221
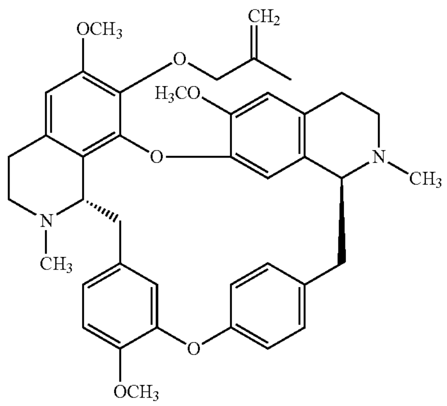

-continued
BS-FC-301
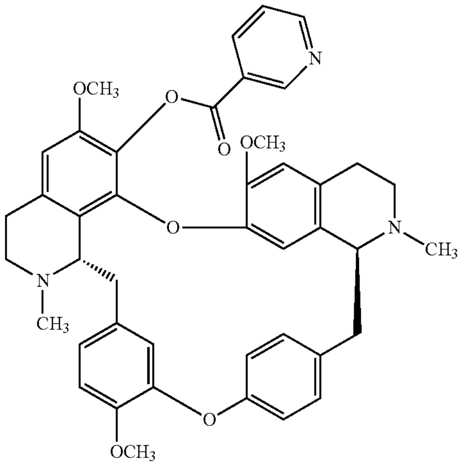
BS-FC-302
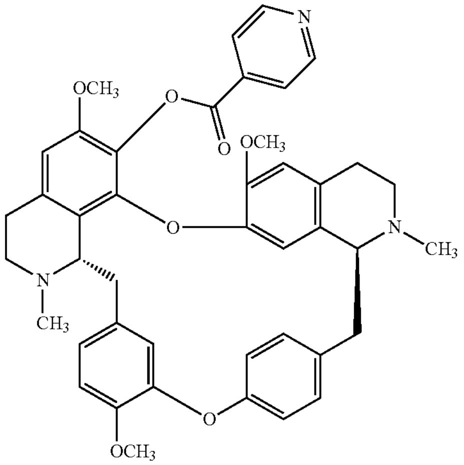
BS-FC-304
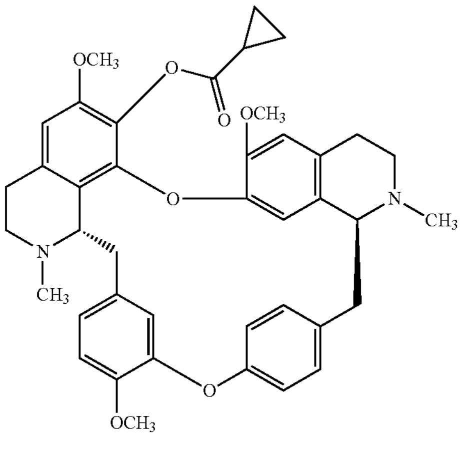
-continued
BS-FC-305
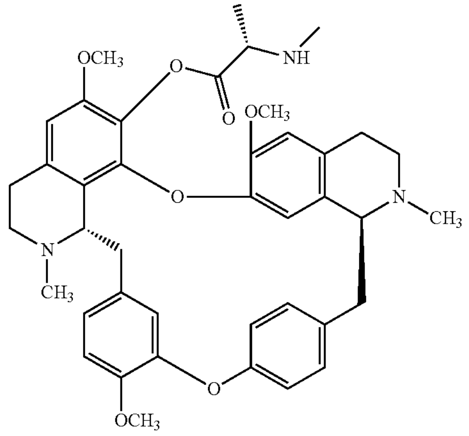
BS-FC-307
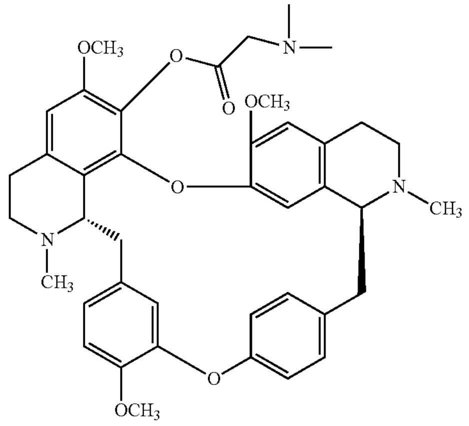
BS-FC-308
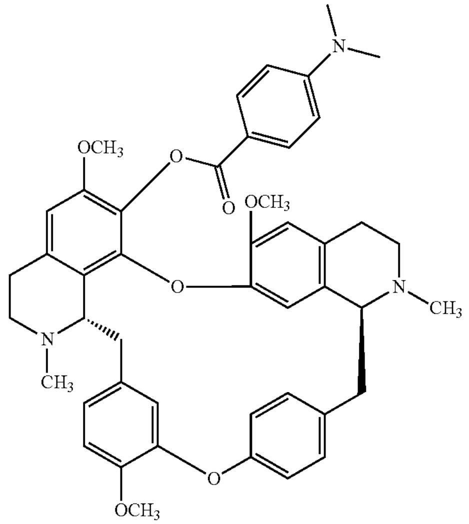

-continued
BS-FC-309
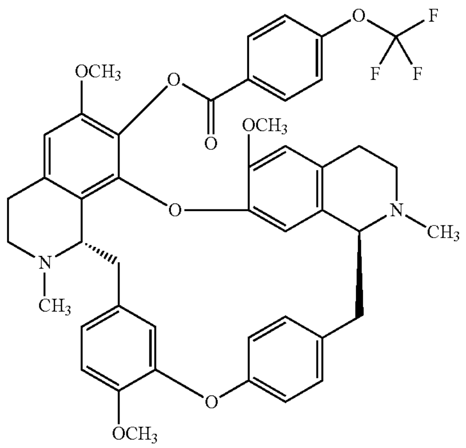
BS-FC-310
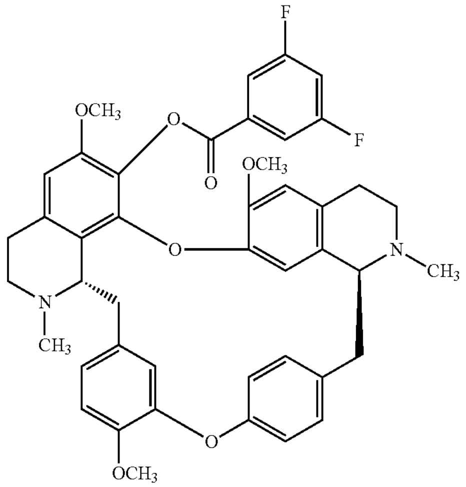
BS-FC-311
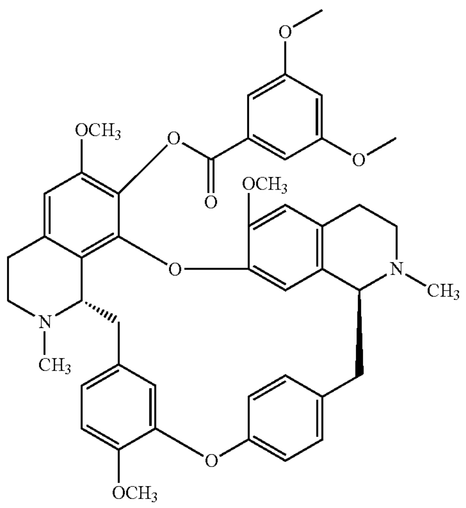
-continued
BS-FC-313
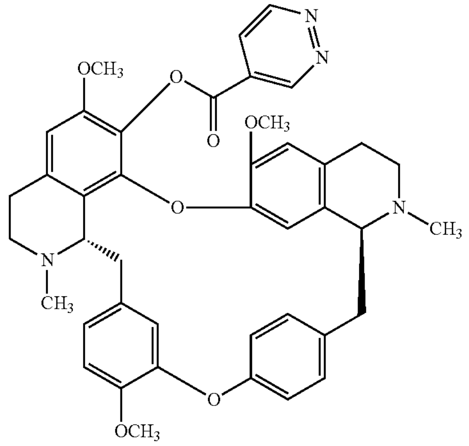
BS-FC-314
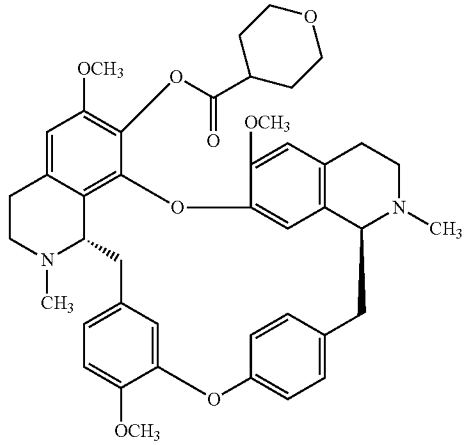
BS-FC-315
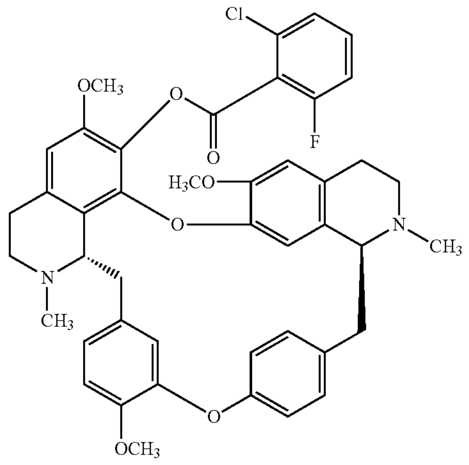

-continued
BS-FC-318
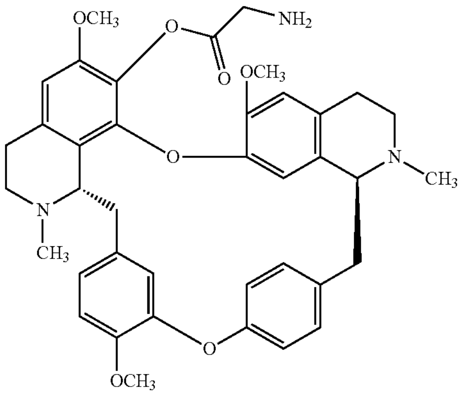
BS-FC-324
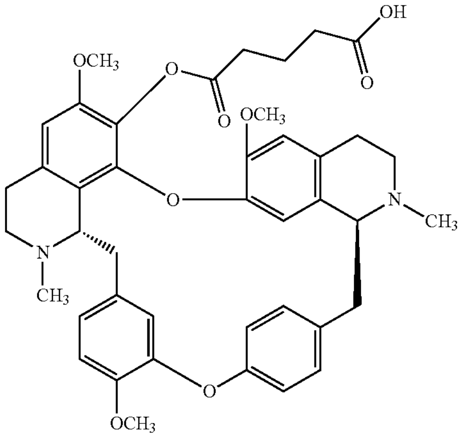
BS-FC-401
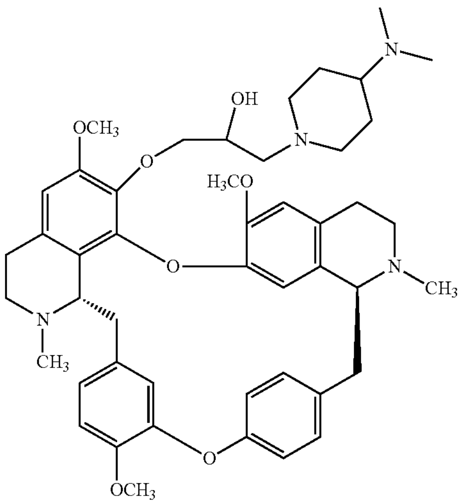
-continued
BS-FC-402
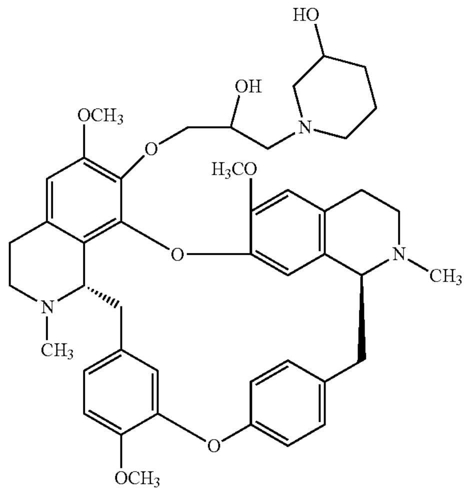
BS-FC-403
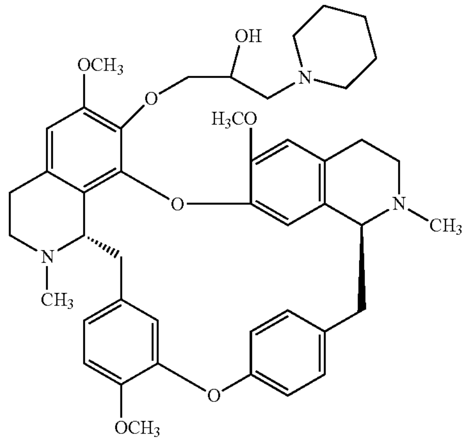
BS-FC-404
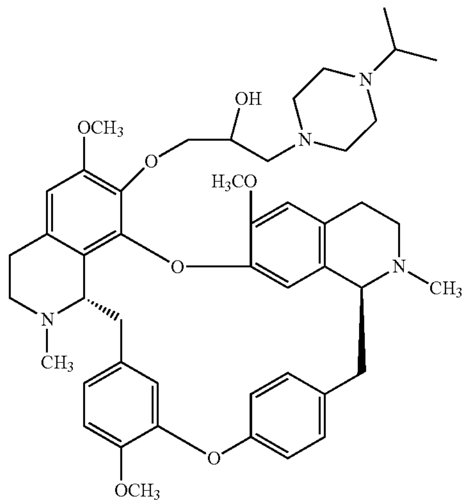

-continued
BS-FC-405
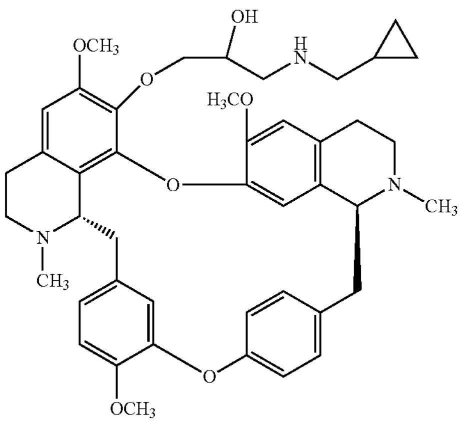
BS-FC-406
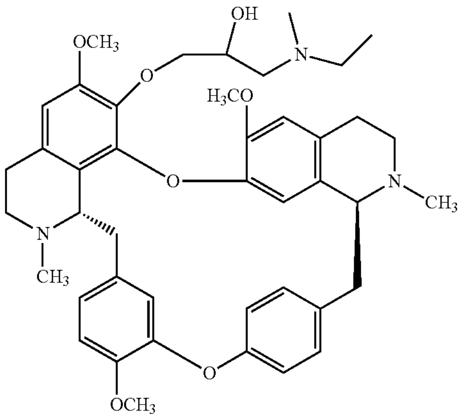
BS-FC-407
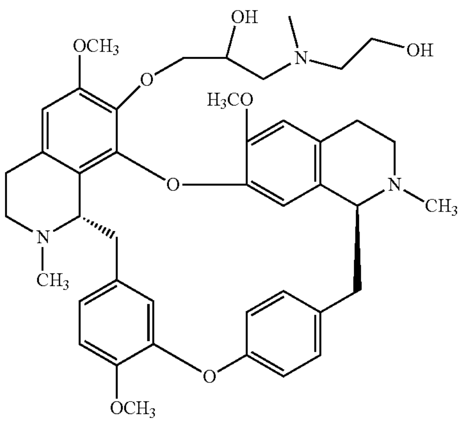
-continued
BS-FC-409
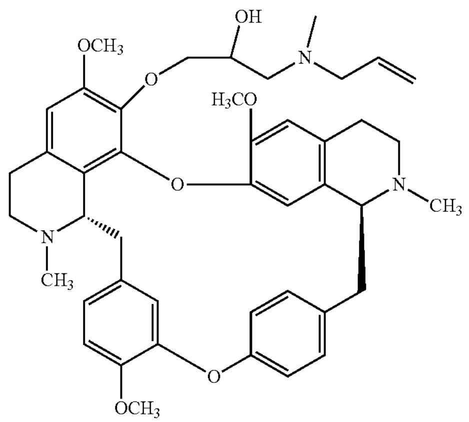
BS-FC-410
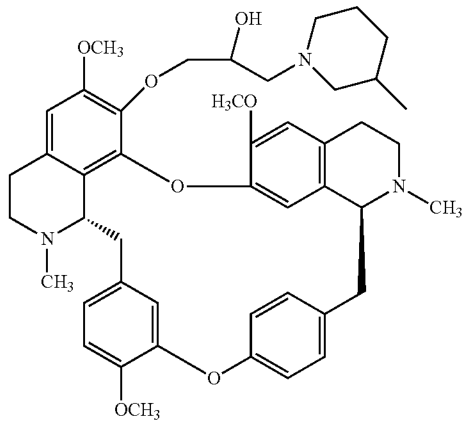
BS-FC-416
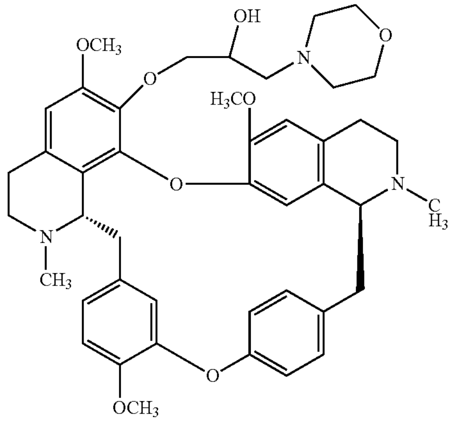

-continued
BS-FC-417
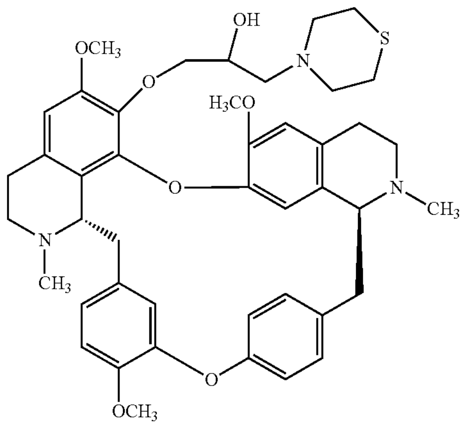
BS-FC-418
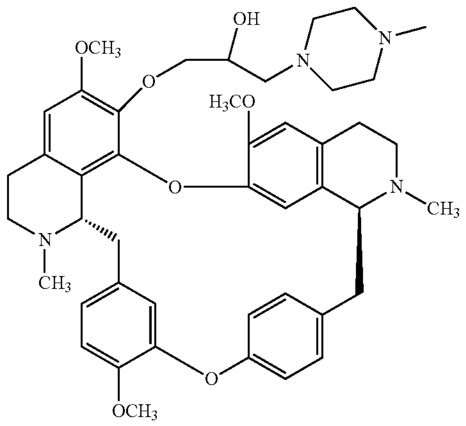
BS-FC-419
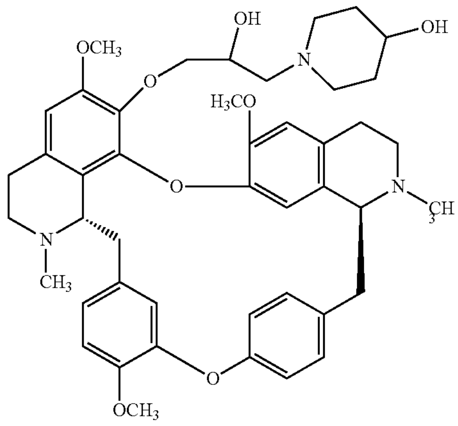
-continued
BS-FC-420
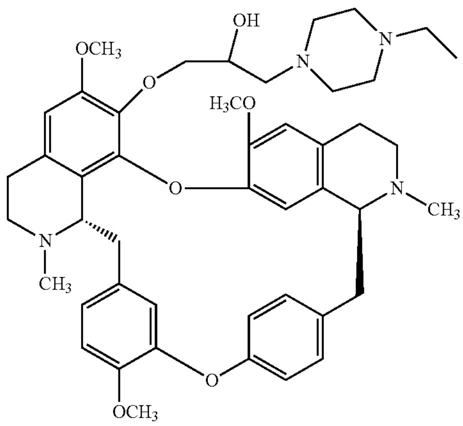
BS-FC-421
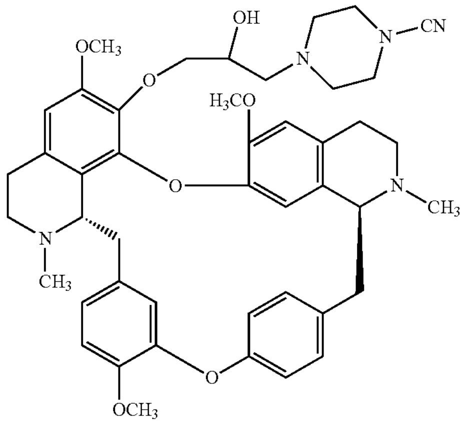
BS-FC-422
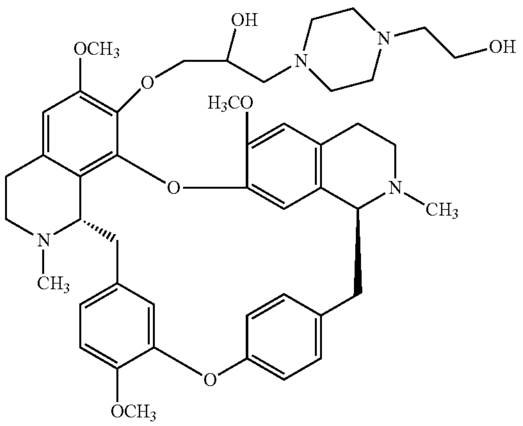

-continued
BS-FC-424
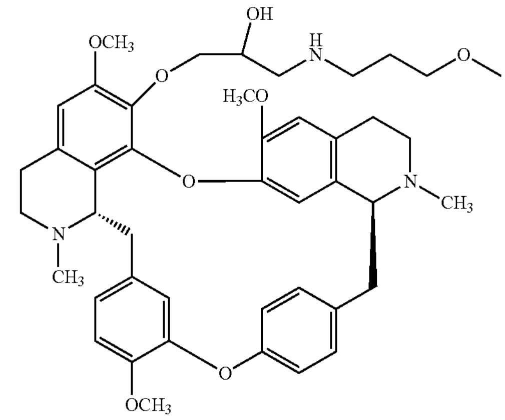
BS-FC-425
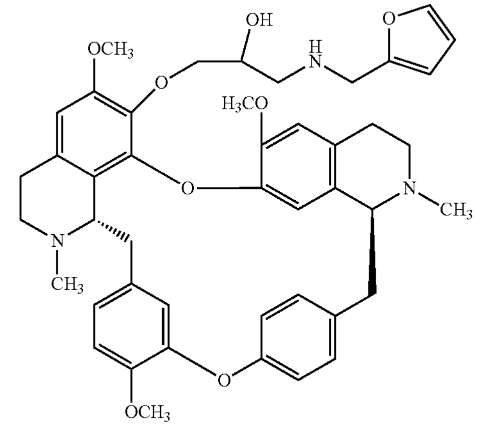
BS-FC-501
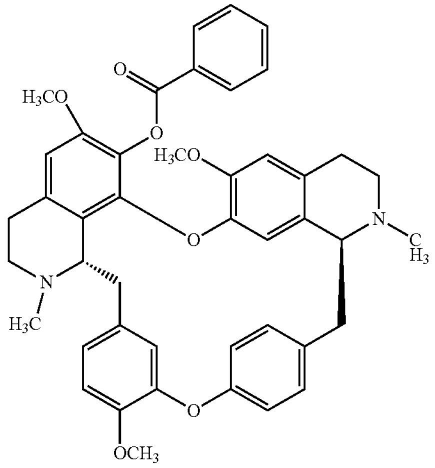
-continued
BS-FC-502
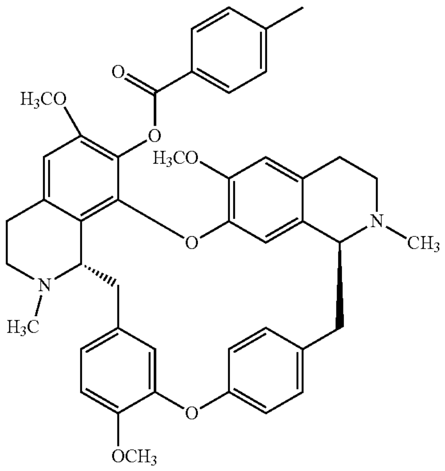
BS-FC-503
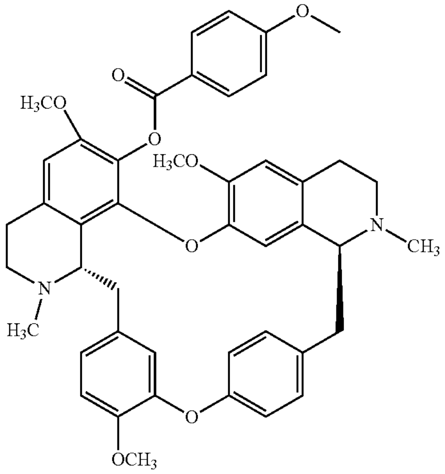

-continued

BS-FC-504

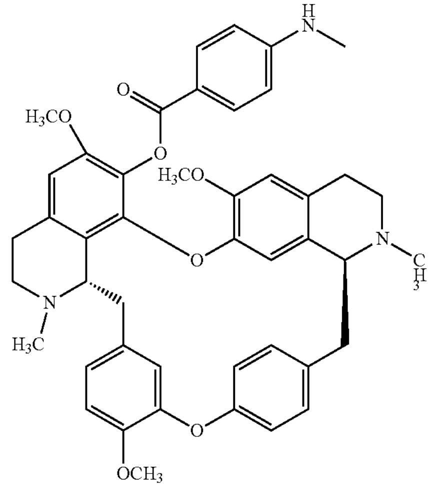

BS-FC-505

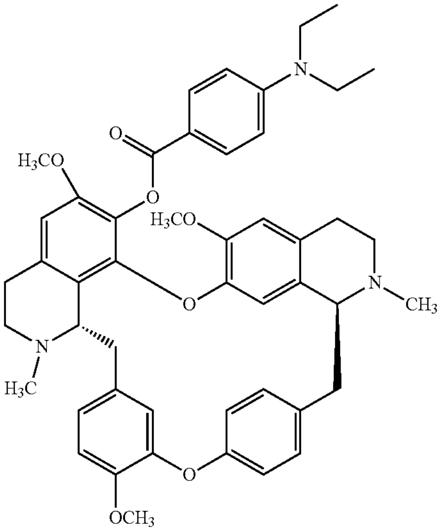

-continued

BS-FC-506

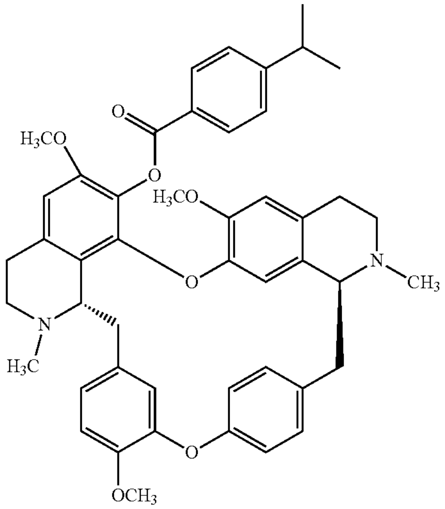

BS-FC-507

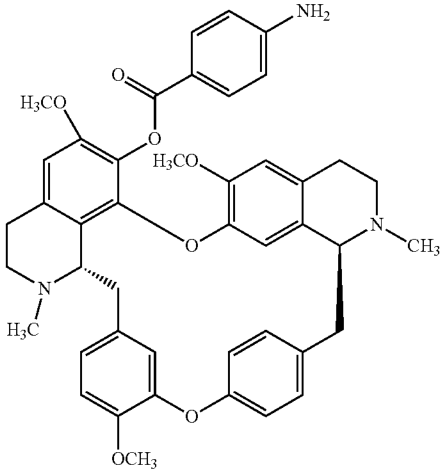

Some data for the compounds listed above are shown in the following table:

| Compound ID | Molecular formula | Molecular weight | Appearance | State | Yield from reaction (%) |
|---|---|---|---|---|---|
| BS-FC-102 | $C_{44}H_{46}N_2O_8S$ | 762.91 | Bright yellow | Powdery solid | 57 |
| BS-FC-104 | $C_{43}H_{44}N_2O_8S$ | 748.88 | Bright yellow | Powdery solid | 54 |
| BS-FC-105 | $C_{38}H_{39}F_3N_2O_8S$ | 740.79 | White | Powdery solid | 60 |
| BS-FC-201 | $C_{44}H_{45}FN_2O_6$ | 716.84 | Bright yellow | Powdery solid | 45 |
| BS-FC-202 | $C_{43}H_{45}N_3O_6$ | 699.83 | Bright yellow | Powdery solid | 21 |
| BS-FC-203 | $C_{45}H_{45}F_3N_2O_7$ | 782.84 | White | Powdery solid | 19 |
| BS-FC-204 | $C_{44}H_{44}F_2N_2O_6$ | 734.83 | Bright yellow | Powdery solid | 13 |
| BS-FC-205 | $C_{44}H_{44}ClFN_2O_6$ | 751.28 | Bright yellow | Powdery solid | 31 |
| BS-FC-206 | $C_{44}H_{44}ClFN_2O_6$ | 751.28 | Bright yellow | Solid | 24 |
| BS-FC-208 | $C_{41}H_{46}N_2O_6$ | 662.81 | Bright yellow | Powdery solid | 34 |
| BS-FC-213 | $C_{40}H_{44}N_2O_6$ | 648.79 | Bright yellow | Powdery solid | 46 |
| BS-FC-215 | $C_{45}H_{48}N_2O_7$ | 728.87 | Bright yellow | Powdery solid | 46 |
| BS-FC-216 | $C_{45}H_{45}F_3N_2O_6$ | 766.84 | Bright yellow | Powdery solid | 42 |
| BS-FC-217 | $C_{44}H_{44}ClFN_2O_6$ | 751.28 | Bright yellow | Powdery solid | 23.9 |
| BS-FC-220 | $C_{42}H_{48}N_2O_6$ | 676.84 | Bright yellow | Solid | 44 |
| BS-FC-221 | $C_{41}H_{46}N_2O_6$ | 662.81 | Bright yellow | Powdery solid | 25 |
| BS-FC-301 | $C_{43}H_{43}N_3O_7$ | 713.82 | Bright yellow | Solid | 21 |
| BS-FC-302 | $C_{43}H_{43}N_3O_7$ | 713.82 | Bright yellow | Powdery solid | 66.9 |
| BS-FC-304 | $C_{41}H_{44}N_2O_7$ | 676.80 | Bright yellow | Powdery solid | 36 |
| BS-FC-305 | $C_{41}H_{47}N_3O_7$ | 693.83 | Bright yellow | Powdery solid | 40 |
| BS-FC-307 | $C_{41}H_{47}N_3O_7$ | 693.80 | White | Powdery solid | 10 |
| BS-FC-308 | $C_{46}H_{49}N_3O_7$ | 755.90 | Bright yellow | Powdery solid | 35 |
| BS-FC-309 | $C_{45}H_{43}F_3N_2O_8$ | 796.83 | Bright yellow | Powdery solid | 38 |
| BS-FC-310 | $C_{44}H_{42}F_2N_2O_7$ | 748.81 | White | Powdery solid | 47 |

-continued

| Compound ID | Molecular formula | Molecular weight | Appearance | State | Yield from reaction (%) |
|---|---|---|---|---|---|
| BS-FC-311 | $C_{46}H_{48}N_2O_9$ | 772.88 | Bright yellow | Powdery solid | 19 |
| BS-FC-313 | $C_{42}H_{42}N_4O_7$ | 714.81 | Bright yellow | Powdery solid | 28 |
| BS-FC-314 | $C_{43}H_{48}N_2O_8$ | 720.85 | Bright yellow | Powdery solid | 34 |
| BS-FC-315 | $C_{44}H_{42}ClFN_2O_7$ | 765.27 | Bright yellow | Powdery solid | 49 |
| BS-FC-318 | $C_{39}H_{43}N_3O_7$ | 665.77 | Bright yellow | Powdery solid | 29 |
| BS-FC-324 | $C_{42}H_{46}N_2O_9$ | 722.82 | White | Powdery solid | 29 |
| BS-FC-401 | $C_{47}H_{60}N_4O_7$ | 792.47 | Bright yellow | Powdery solid | 26 |
| BS-FC-402 | $C_{45}H_{55}N_3O_8$ | 765.4 | Bright yellow | Powdery solid | 21 |
| BS-FC-403 | $C_{45}H_{55}N_3O_7$ | 749.4 | Bright yellow | Powdery solid | 27 |
| BS-FC-404 | $C_{47}H_{60}N_4O_7$ | 792.45 | Bright yellow | Powdery solid | 18 |
| BS-FC-405 | $C_{44}H_{53}N_3O_7$ | 735.39 | Bright yellow | Powdery solid | 25 |
| BS-FC-406 | $C_{43}H_{53}N_3O_7$ | 723.39 | Bright yellow | Powdery solid | 23 |
| BS-FC-407 | $C_{43}H_{53}N_3O_8$ | 739.38 | Bright yellow | Powdery solid | 30 |
| BS-FC-408 | $C_{46}H_{58}N_4O_7$ | 778.98 | Bright yellow | Powdery solid | 25 |
| BS-FC-409 | $C_{44}H_{53}N_3O_7$ | 735.91 | Bright yellow | Powdery solid | 20 |
| BS-FC-410 | $C_{46}H_{57}N_3O_7$ | 763.96 | Bright yellow | Powdery solid | 28 |
| BS-FC-413 | $C_{42}H_{48}F_3N_3O_7$ | 763.84 | Bright yellow | Powdery solid | 21 |
| BS-FC-414 | $C_{42}H_{51}N_3O_8$ | 725.87 | Bright yellow | Powdery solid | 22 |
| BS-FC-416 | $C_{44}H_{53}N_3O_8$ | 751.37 | Bright yellow | Powdery solid | 17 |
| BS-FC-417 | $C_{44}H_{53}N_3O_7S$ | 767.36 | Bright yellow | Powdery solid | 23 |
| BS-FC-418 | $C_{45}H_{56}N_4O_7$ | 764.41 | Bright yellow | Powdery solid | 26 |
| BS-FC-419 | $C_{45}H_{55}N_3O_8$ | 765.4 | Bright yellow | Powdery solid | 28 |
| BS-FC-420 | $C_{46}H_{58}N_4O_7$ | 778.43 | Bright yellow | Powdery solid | 38 |
| BS-FC-421 | $C_{45}H_{53}N_5O_7$ | 774.4 | Bright yellow | Powdery solid | 24 |
| BS-FC-422 | $C_{46}H_{58}N_4O_8$ | 794.43 | Bright yellow | Powdery solid | 35 |
| BS-FC-424 | $C_{44}H_{55}N_3O_8$ | 753.92 | Bright yellow | Powdery solid | 27 |
| BS-FC-425 | $C_{45}H_{51}N_3O_8$ | 761.37 | Bright yellow | Powdery solid | 28 |
| BS-FC-501 | $C_{44}H_{44}N_2O_7$ | 712.84 | White | Powdery solid | 10 |
| BS-FC-502 | $C_{45}H_{46}N_2O_7$ | 726.87 | White | Powdery solid | 8 |
| BS-FC-503 | $C_{45}H_{46}N_2O_8$ | 742.87 | White | Powdery solid | 9 |
| BS-FC-504 | $C_{45}H_{47}N_3O_7$ | 741.88 | White | Powdery solid | 7 |
| BS-FC-505 | $C_{48}H_{53}N_3O_7$ | 783.97 | White | Powdery solid | 8 |
| BS-FC-506 | $C_{47}H_{50}N_2O_7$ | 754.92 | Bright yellow | Powdery solid | 9 |
| BS-FC-507 | $C_{44}H_{45}N_3O_7$ | 727.86 | White | Powdery solid | 10 |

The compounds as follows are particularly preferred according to the present invention: BS-FC-102, BS-FC-104, BS-FC-204, BS-FC-207, BS-FC-208, BS-FC-213, BS-FC-216, BS-FC-220, BS-FC-221, BS-FC-304, BS-FC-308, BS-FC-311, BS-FC-315, BS-FC-403, BS-FC-405, BS-FC-409, BS-FC-410, BS-FC-417, BS-FC-421. It is discovered that they exhibit an antitumor activity against at least one type of tumor that is significantly superior to that of unmodified fangchinoline.

The compounds as follows are most preferred according to the present invention. They exhibit an excellent antitumor activity fully superior to that of fangchinoline.

BS-FC-104

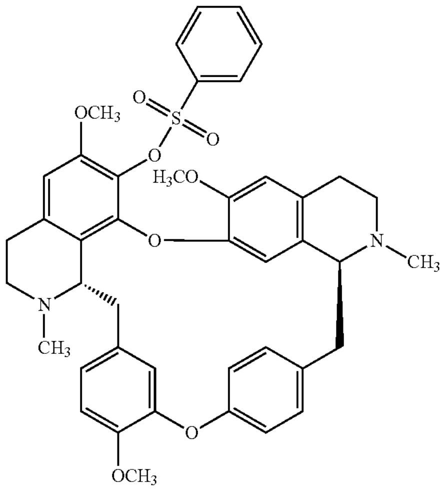

7-benzenesulfonyl fangchinoline

-continued
BS-FC-221
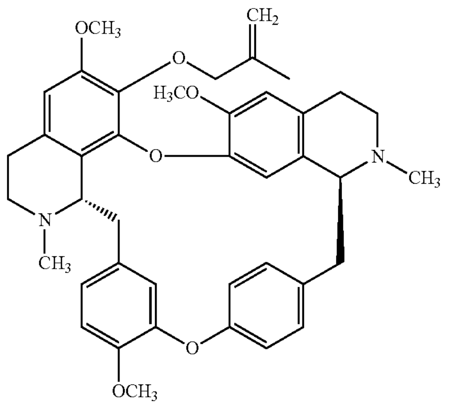
7-isobutenyloxy fangchinoline
BS-FC-308
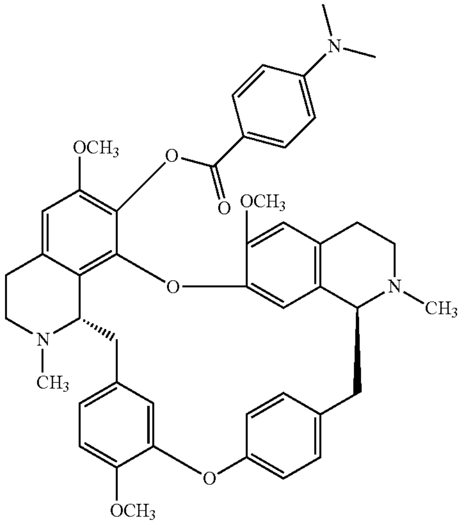
7-(N,N-dimethylamino-benzoyloxy)-fangchinoline
BS-FC-311
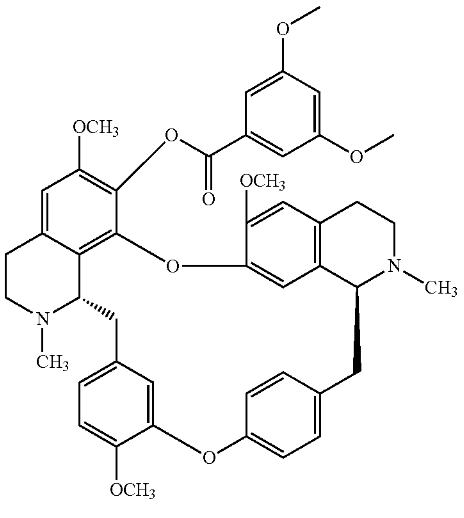
7-(3,5-dimethoxy-benzoyloxy)-fangchinoline
-continued
BS-FC-403
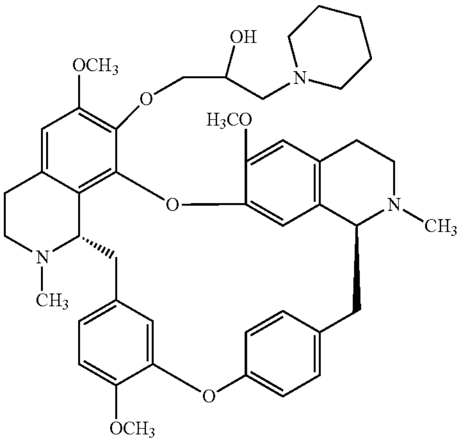
7-(1-piperidyl-2-hydroxy-propoxy)-fangchinoline
BS-FC-405
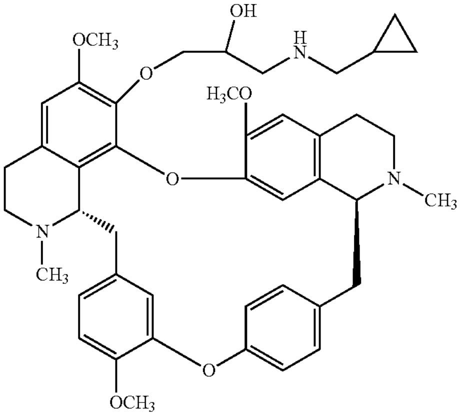
7-(1-cyclopropylmethylamino-2-hydroxy-propoxy)-fangchinoline
BS-FC-409
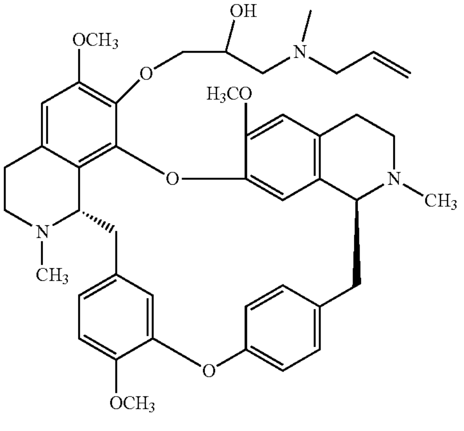
7-(1-N-allylmethylamino-2-hydroxy-propoxy)-fangchinoline -continued

BS-FC-410

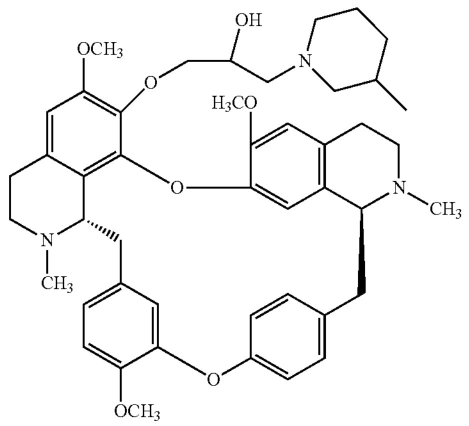

and, 7-(1-(3-methyl)piperidyl-2-hydroxy-propoxy)-fangchinoline

BS-FC-421

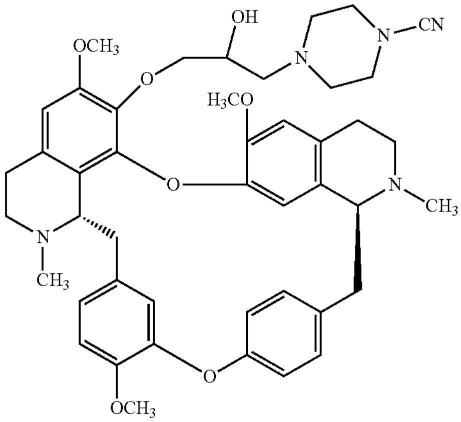

7-(1-N-cyanopiperazinyl-2-hydroxy-propoxy)-fangchinoline

The present invention relates to salts, solvates, hydrates, adducts, complexes, polymorphs and prodrugs of the compounds of formula (I) of the present invention.

As used herein, the term "alkyl" refers to a straight or branched alkyl containing designated number of carbon atoms. The alkyl can comprise 1-6, 1-5, 1-4 or 1-3 carbon atoms. Examples of alkyl include, but not limited to, methyl, ethyl, n-propyl, isopropyl, tert-butyl, n-pentyl, and n-hexyl.

The term "alkenyl" refers to a straight or branched alkenyl containing designated number of carbon atoms. The alkenyl can comprise 2-6, 2-5, 2-4 or 2-3 carbon atoms. Examples of alkenyl include, but not limited to, vinyl, allyl, butenyl, and isobutenyl.

The term "alkynyl" refers to a straight or branched alkynyl containing designated number of carbon atoms. The alkynyl can comprise 2-6, 2-5, 2-4 or 2-3 carbon atoms. Examples of alkynyl include, but not limited to, acetenyl and propinyl.

The term "$C_3$-$C_7$ cycloalkyl or cycloalkenyl" refers to a 3-7 membered monocyclic hydrocarbon radical having either a saturated or an unsaturated ring. $C_3$-$C_7$ cycloalkyl or cycloalkenyl can be cyclopropyl, cyclobutyl, cyclopentyl, cyclohexyl, cycloheptyl, cyclopropenyl and cyclohexenyl.

The term "aryl" refers to a monocyclic aryl or polycyclic aryl, fused or unfused, containing 6-14 (such as 6-12, 6-20) carbon atoms. In the case of polycyclic aryl, at least one ring is aromatic. Aryl can also be fused with a heterocyclyl. Examples of aryl include phenyl, biphenyl, naphthyl, 5,6,7,8-tetrahydronaphthyl, 2,3-dihydrobenzofuranyl, etc.

The term "heteroaryl" refers to an aromatic ring group having 1-4 heteroatoms (e.g. 1, 2, 3 or 4 heteroatoms) in the ring as ring atom(s). A heteroatom refers to nitrogen, oxygen or sulfur. A heteroaryl can be a monocyclic heteroaryl having 5-7 ring atoms or a bicyclic heteroaryl having 7-11 ring atoms. Said bicyclic heteroaryl should comprise at least one aromatic heterocycle, and the other ring can be aromatic or non-aromatic, with or without a heteroatom. Examples of heteroaryl include such as pyrrolyl, pyrazolyl, imidazolyl, oxazolyl, pyridinyl, pyrimidinyl, furanyl, thiophenyl, isoxazolyl, indolyl, etc.

The term "heterocyclyl" refers to a non-aromatic cyclic group containing 1-4 heteroatoms (e.g. 1, 2, 3 or 4 heteroatoms) as ring members. A heteroatom refers to nitrogen, oxygen or sulfur. A heterocyclyl can be a monocyclic heterocyclyl having 4-8 ring atoms (such as 4-7 membered ring, 5-7 membered ring and 5-6 membered ring) or a bicyclic heterocyclyl having 7-11 ring atoms. A heterocyclyl can be either aromatic or non-aromatic. Examples of heterocyclyls include azacyclobutyl, pyrrolidinyl, pyrrolinyl, tetrahydrofuryl, dihydrofuryl, piperazinyl, piperidyl, morpholinyl, thiomorpholinyl, tetrahydropyranyl, tetrahydrothienyl, etc.

The term "nitrogen-containing heterocyclyl" refers to a "heterocyclyl" as defined above that comprises at least one nitrogen atom as a ring member.

The term "halogen" refers to fluorine, chlorine, bromine or iodine.

The term "alkylamino" refers to an amino group substituted with one or two alkyls defined as above.

The term "alkoxy" includes alkyl-O-group, wherein the alkyl is defined as above.

The term "alkylthio" includes alkyl-S-group, wherein the alkyl is defined as above.

The term "pharmaceutically acceptable adducts and complexes of the compounds of formula (I)" refers to the product formed by a compound of the present invention with further combined small molecule or biological macromolecule via a non-chemical bond or non-covalent intermolecular force.

As used herein, the term "pharmaceutically acceptable salts of the compounds of formula (I)" can be exemplified by organic acid salts formed by an organic acid bearing a pharmaceutically acceptable anion. These organic acid salts include, but not limited to, tosylate, methanesulfonate, malate, acetate, citrate, malonate, tartrate, succinate, benzoate, ascorbate, α-ketoglutarate, and α-glycerophosphate. Suitable inorganic salts may also be formed, including but not limited to, hydrochloride, sulfate, nitrate, bicarbonate and carbonate, phosphate, hydrobromate, hydriodate salts and the like.

A pharmaceutically acceptable salt may be obtained using standard procedures well known in the art, for example by reacting a sufficient amount of alkaline compound with a suitable acid that provides a pharmaceutically acceptable anion.

As used herein, the term "polymorph" means a solid crystalline form of the compound of the present invention or a complex thereof. Various polymorphs of one same compound may exhibit different physical, chemical and/or spectroscopic properties. The different physical properties include, but not limited to, stability (e.g., thermal or light stability), compressibility and density (which are important for formulation and manufacture of the product), and dissolution rate (which may affect its bioavailability and absorbability). Differences in stability may result in a change in chemical reactivity (e.g., differential oxidation, such that a dosage form comprised of one polymorph discolors more rapidly than one comprised of another polymorph) or mechanical properties (e.g., in storage, crushed parts of the tablet of a kinetically favored polymorph is converted to a thermodynamically more stable polymorph) or both (e.g., tablets composed of one polymorph are more susceptible to breakdown at high humidity). Different physical properties of various polymorphs may affect their processing. For example, one polymorph may be more likely to form a solvate or may be more difficult to be filtered out or purified by washing than another one due to, for example, their different particle shapes or size distributions.

As used herein, the term "hydrate" means such a compound of the present invention or a salt thereof as further comprising a stoichiometric or non-stoichiometric amount of water bound via non-covalent intermolecular forces.

Unless otherwise indicated, the term "prodrug" used herein means a derivative of an inventive compound that, via hydrolyzation, oxidization, or other reactions under a biological condition (in vitro or in vivo), can provide a compound of this invention. A prodrug may only become active upon such a reaction under a biological condition, or may have activities in its unreacted form. Typically, a prodrug can be prepared using known methods, such as those described in *Burger's Medicinal Chemistry and Drug Discovery* (1995) 172-178, 949-982 (Manfred E. Wolff, 5th edition), *Prodrugs and Targeted Delivery* by J. Rautio (2011) 31-60 (Wiley-VCH, *Methods and Principles in Medicinal Chemistry*, Vol. 47), and *Fundamentals of Medicinal Chemistry* (2003) by G. Thomas, 195-200 (Wiley).

The two chiral centers of the 7-substituted fangchinoline derivatives in the compounds of the present invention have the stereochemical structure represented by the structural formula (I). The stereochemical definitions and conventions used herein generally follow McGraw-Hill Dictionary of Chemical Terms (S. P. Parker, Ed., McGraw-Hill Book Company, New York, 1984); and Eliel, E. and Wilen, S., Stereochemistry of Organic Compounds (John Wiley & Sons, Inc., New York, 1994). Many organic compounds are present in optically active forms, i.e., they have the ability to rotate a plane of plane-polarized light.

The "antitumor activity" as used herein refers to direct inhibition or killing of tumor cells or tissue. The examples of the present application partially determine the antitumor activity of the compounds of the present invention.

The terms "treatment", "treating", "treat" and the like used herein refer generally to obtaining a desired pharmacological and/or physiological effect. The effect may be prophylactic in terms of completely or partially preventing a disease or symptoms thereof and/or may be therapeutic in terms of partial or complete stabilization or cure of a disease and/or adverse effects caused by the disease. "Treatment" as used herein covers any treatment of a disease in a subject, including: (a) preventing the disease or symptoms from occurring in a subject who is predisposed to the disease or symptoms but has not yet been diagnosed as having it; (b) inhibiting the symptoms of a disease, i.e., arresting its development; or (c) relieving the symptoms of a disease, i.e., causing regression of the disease or symptoms.

The compounds of the present invention can be prepared through a conventional organic chemistry synthesis process. For example, the 7-substituted fangchinoline derivatives of formula (I) of the present invention are prepared as follows.

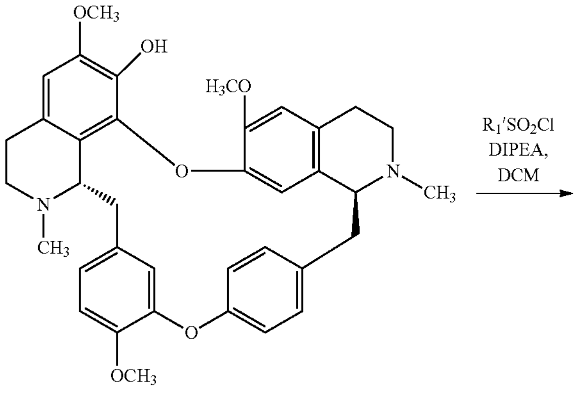

FAN

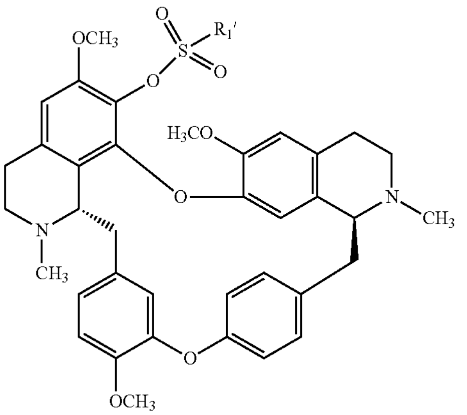

I-1

The 7-substituted fangchinoline derivative of formula (I-1) can be produced by reacting fangchinoline (FAN) with a corresponding alkyl or aromatic sulfonyl chloride ($R_1$'$SO_2$Cl) in the presence of an alkali at room temperature.

The alkali used in the above reaction can be either an organic or an inorganic alkali. Examples can be such as triethylamine, diisopropylethylamine, sodium hydroxide, etc. The organic sulfonyl chloride can be either a commercially available starting material or prepared from an organic sulfonic acid.

The above reaction typically takes place in a solvent. The solvent for the reaction includes, but not limited to, dichloromethane, acetonitrile, N,N-dimethylformamide, tetrahydrofuran, etc.

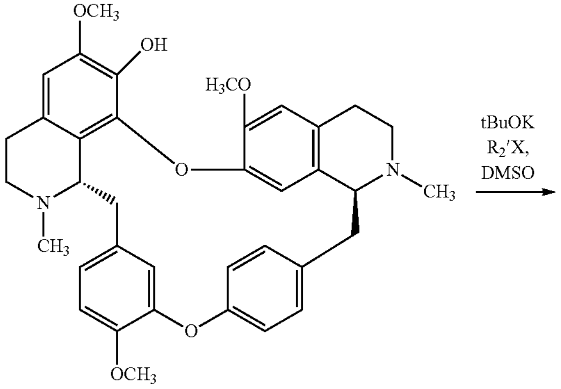

FC

-continued

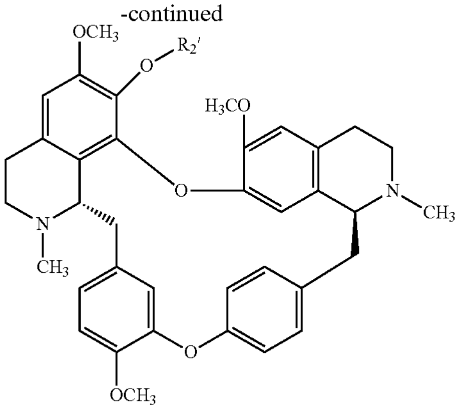

I-2

The 7-substituted fangchinoline derivative of formula (I-2) can be produced by reacting fangchinoline (FAN) firstly with a strong alkali and then with a corresponding halohydrocarbon ($R_2$'X) in the presence of an alkali.

The alkali used in the above reaction includes, but not limited to, organic alkali such as potassium tert-butoxide, sodium ethoxide, and potassium ethoxide. The chlorohydrocarbon can be a commercially available starting material.

The temperature of the above reaction depends on the reactivity of the chlorohydrocarbon and can be either at room temperature or under heating condition, such as at a temperature of 30 to 80° C.

The above reaction typically takes place in a solvent. The solvent used for the reaction includes, but not limited to, dimethylsulfoxide, acetonitrile, N,N-dimethylformamide and tetrahydrofuran.

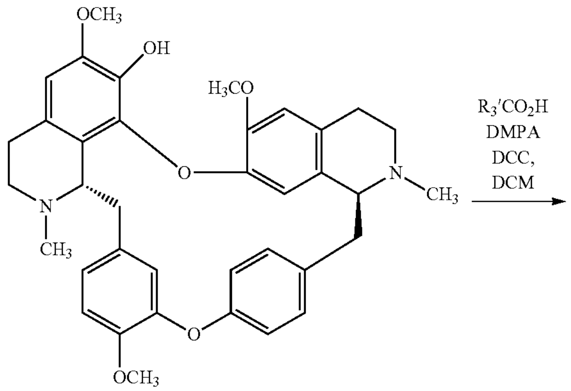

FC

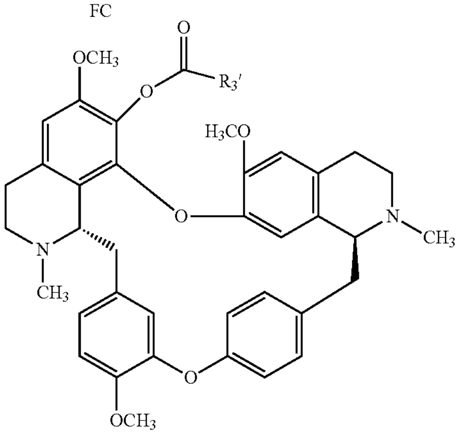

I-3

The 7-substituted fangchinoline derivative of formula (I-3) can be produced by reacting fangchinoline (FAN) with a corresponding organic acid ($R_3$'$CO_2$H) in the presence of a condensating agent and an alkali at room temperature.

The alkali used in the above reaction includes, but not limited to, an organic alkali, such as triethylamine, diisopropylethylamine, and dimethylaminopyridine. The organic acid can be a commercially available starting material and an organic acyl chloride may also be used in this reaction.

The temperature of the above reaction depends on the reactivity of the organic acid and can be either at room temperature or under heating condition, such as at a temperature of 30 to 60° C.

The above reaction typically takes place in the presence of a condensating agent. The condensating agent herein can be, but not limited to, an organic condensating agent, such as diisopropylcarbodiimide, dicyclohexylcarbodiimide, etc.

The esterification reaction typically takes place in a solvent but it may also take place in the absence of a solvent. The solvent used includes, but not limited to, an organic polar solvent, such as dichloromethane (DCM), tetrahydrofuran (THF), N,N-dimethylformamide (DMF), dimethylsulfoxide (DMSO), etc.

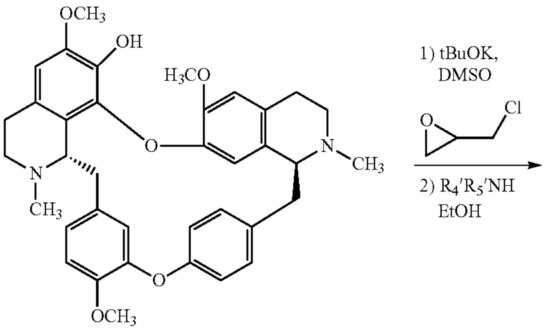

FC

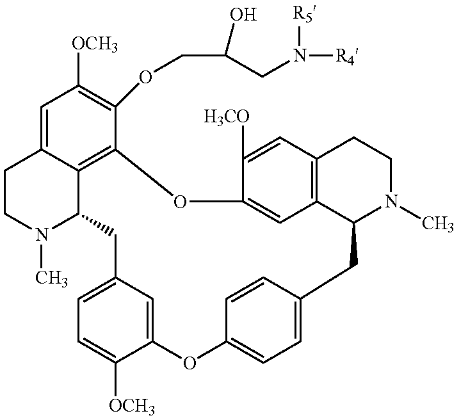

I-4

The 7-substituted fangchinoline derivative of formula (I-4) can be produced by a two-step reaction:

(1) reacting fangchinoline with potassium tert-butoxide at a low temperature and add chloromethyl propylene oxide dropwise at an ice bath temperature. The reaction lasts 30 min to 2 hr, followed by extraction to give the substituted intermediate.

(2) reacting this intermediate with a corresponding organic amine to give the product. The temperature of the amination depends on the reactivity of the organic amine and it typically needs heating, such as at a temperature of 80 to 120° C.

The amination typically takes place in a polar solvent. The solvent used includes, but not limited to, ethanol, tetrahydrofuran (THF), N,N-dimethylformamide (DMF), dimethylsulfoxide (DMSO), etc.

In formula (I-1), (I-2), (I-3), and (I-4), $R_1$, $R_2$, $R_3$ and $R_4$ are defined the same as in the above formula (I).

The starting materials for the above reaction, such as organic acids, organic amines, organic sulfonyl chloride and organic acyl chlorides, are all commercially available. The fangchinoline material can be either obtained by extraction from natural products or commercially available.

Conventional chemical conversion processes may be used to practice this invention. One skilled person in the art can determine suitable chemical agents, solvents, protecting groups, and reaction conditions for these chemical conversions. Relevant information are described, for example, in R. Larock, *Comprehensive Organic Transformations*, VCH Publishers (1989); T. W. Greene and P. G. M. Wuts, *Protective Groups in Organic Synthesis*, 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Protecting groups refer to the groups that, upon being attached to an active moiety (e.g., a hydroxyl or amino group), prevent the moiety from interference in a subsequent reaction and, after the reaction, can be removed through a conventional method. Examples of protecting groups for a hydroxyl include, but not limited to, alkyl, benzyl, allyl, trityl (also known as triphenylmethyl), acyl (e.g., benzoyl, acetyl, or HOOC—X"—CO—, wherein X" is alkylidene, alkenylene, cycloalkylene, or arylene), silyl (e.g., trimethylsilyl, triethylsilyl, and t-butyldimethylsilyl), alkoxylcarbonyl, aminocarbonyl (e.g., dimethylaminocarbonyl, methylethylaminocarbonyl, and phenylaminocarbonyl), alkoxymethyl, benzyloxymethyl, and alkylmercaptomethyl. Examples of protecting groups for an amino include, but not limited to, alkoxycarbonyl, alkanoyl, aryloxycarbonyl, aryl-substituted alkyl and the like. Protecting groups for hydroxyl and amino have been discussed in T. W. Greene and P. G. M. Wuts, Protective Groups in Organic Synthesis, 2nd. Ed., John Wiley and Sons (1991). All hydroxyl and amino protecting groups can be removed by a conventional method after the reaction.

The present invention also provides a pharmaceutical composition comprising the compound of formula (I) of the present invention.

The present invention provides a pharmaceutical composition which comprises at least one compound of formula (I) of the present invention as defined above and optionally a pharmaceutically acceptable excipient.

The methods for preparing various pharmaceutical compositions having a given amount of active components are known or will be apparent to those skilled in the art in light of this disclosure. As described in REMINGTON'S PHARMACEUTICAL SCIENCES, Martin, E. W., ed., Mack Publishing Company, 19th ed. (1995), the methods for preparing such pharmaceutical compositions include incorporation of other suitable pharmaceutical excipients, carriers, diluents, etc.

The pharmaceutical preparations of the present invention are produced by known methods, including mixing, dissolving, or freeze drying processes.

The compounds of the present invention may be formulated into a pharmaceutical composition and administered to a subject in a route suitable for the selected administration manner, e.g., orally or parenterally (for example, by an intravenous, intramuscular, topical or subcutaneous route).

Thus, the present compounds may be systemically administered, e.g., orally administered, in conjugation with a pharmaceutically acceptable carrier such as an inert diluent or an edible carrier. They may be enclosed in hard or soft gelatin capsules, or may be compressed into tablets. For therapeutic oral administration, the active compound may be combined with one or more excipients and may be taken in a form of ingestible tablet, buccal tablet, troche, capsule, elixir, suspension, syrup, wafer, and the like. Such a composition or preparation should contain at least 0.1% of the active compound. Of course, the proportion of active compound in the compositions and preparations may vary and may be from about 1% to about 99% by weight of a given unit dosage form. In a therapeutically useful composition, the active compound is present in an amount such that an effective dosage level is achieved.

A tablet, troche, pill, capsule and the like may also comprise a binder, such as gum tragacanth, arabic gum, corn starch or gelatin; an excipient such as calcium dihydrogenphosphate; a disintegrating agent such as corn starch, potato starch, alginic acid and the like; a lubricant such as magnesium stearate; and a sweetening agent such as sucrose, fructose, lactose or aspartame; or a flavoring agent such as peppermint, wintergreen oil, or cherry flavor. In case the unit dosage form is a capsule, it may comprise, in addition to the above materials, a liquid vehicle such as a vegetable oil or polyethylene glycol. Various other materials may be present as coatings or otherwise modify the physical form of the solid unit dosage form. For instance, a tablet, pill, or capsule may be coated with gelatin, wax, shellac or sugar, etc. A syrup or elixir may contain an active compound, a sweetening agent such as sucrose or fructose, a preservative such as methylparaben or propylparaben, a dye and a flavoring agent (such as cherry or orange flavor). Of course, any materials used in preparing unit dosage forms should be pharmaceutically acceptable and substantially non-toxic in the amounts employed. In addition, the active compound may be incorporated into a sustained-release preparation or in a device.

The active compound may also be administered intravenously or intraperitoneally by infusion or injection. An aqueous solution of the active compound or its salt may be prepared, optionally mixed with a nontoxic surfactant. Also can be prepared is dispersion in glycerol, liquid polyethylene glycol, triacetin, or a mixture thereof, or in an oil. Under ordinary storage and use conditions, these preparations contain a preservative to prevent the growth of microorganisms.

The pharmaceutical dosage forms suitable for injection or infusion may include a sterile aqueous solution, a dispersion or a sterile powder comprising active ingredient (optionally encapsulated in liposomes), which are adapted for an extemporaneous preparation of a sterile injectable or infusible solution or dispersion. In all cases, the final dosage form must be sterile and stable liquids under the manufacture and storage conditions. The liquid carrier or vehicle may be a solvent or a liquid dispersion medium comprising, for example, water, ethanol, a polyol (for example, glycerol, propylene glycol, liquid polyethylene glycol, and the like), a vegetable oil, a nontoxic glyceryl ester, and a suitable mixture thereof. A proper fluidity can be maintained, for example, by formation of liposomes, by maintenance of the required particle size in the case of dispersion or by the use of a surfactant. The prevention of microorganism can be achieved by various antibacterial and antifungal agents, such as parabens, chlorobutanol, phenol, sorbic acid, thimerosal, and the like. In many cases, an isotonic agent is preferably comprised, such as sugar, buffer agent or sodium chloride. Prolonged absorption of an injectable composition can be obtained by the use of a composition of the agents for delaying absorption, for example, aluminum monostearate and gelatin.

An injectable sterile solution is prepared by combining a required amount of the active compound in a suitable solvent with various additional desired components as listed above, followed by filtration and sterilization. For sterile powder used to prepare an injectable sterile solution, the preferred preparation process is vacuum drying and freeze drying techniques, which yield a powder of the active ingredient plus any additional desired ingredient present in the previous filtered sterile solution.

Useful solid carriers include finely divided solids such as talc, clay, microcrystalline cellulose, silica, alumina and the like. Useful liquid carriers include water, ethanol or ethylene glycol or a water-ethanol ethylene glycol mixture, in which the compound of the present invention can be dissolved or dispersed at an effective content, optionally with the aid of a non-toxic surfactant. An adjuvant (such as a flavour) and additional antimicrobial agent can be added to optimize the properties for a given application.

Thickening agent (such as a synthetic polymer, a fatty acid, a fatty acid salt and ester, a fatty alcohol, a modified cellulose or a modified inorganic material) can also be used with a liquid carrier to form a spreadable paste, gel, ointment, soap and the like for applying directly to the skin of a user.

The amount of the compound or an active salt or derivative thereof required for a treatment varies depending not only on the selected particular salt but also on the administration route, the nature of the condition to be treated and the age and condition of the subject, and will be ultimately determined at the discretion of the attendant physician or clinician.

The above formulations can be present in a unit dosage form which is a physically discrete unit containing a unit dosage, which is suitable for administering to a human or other mammalians. The unit dosage form may be a capsule or a tablet, or a plurality of capsules or tablets. Depending upon the intended particular therapy, the amount of the active ingredient in a unit dosage form can be varied or adjusted in the range of about 0.1 mg to about 1,000 mg or more.

The present invention also provides the use of a compound according to the present invention or a pharmaceutical composition comprising the compound of the present invention in manufacture of a medicament, especially an antitumor medicament. Accordingly, the present invention provides a method for treating a subject suffering from tumor, comprising administering to the subject in need thereof a therapeutically effective amount of at least one compound of the present invention. The 7-substituted fangchinoline derivatives of the present invention or a pharmaceutically acceptable salt thereof can be used, for example, for the treatment of leukemia, multiple myeloma, lymphoma, liver cancer, gastric cancer, breast cancer, cholangiocellular carcinoma, pancreatic cancer, lung cancer, colorectal cancer, osteosarcoma, melanoma, cervical cancer, glioma, nasopharyngeal carcinoma, laryngeal carcinoma, esophageal cancer, middle ear tumor, prostate cancer, etc.

The present invention will be explained in more detailed by the following examples. However, it should be understood that the following examples are intended for illustration only but not to limit the scope of the present invention in any way.

The raw chemicals used in the following examples are commercially available or may be obtained by a synthesis method known in the art.

Example 1

The Synthesis of Compound BS-FC-102

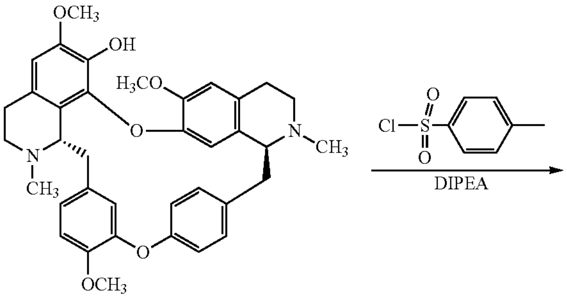

Fangchinoline

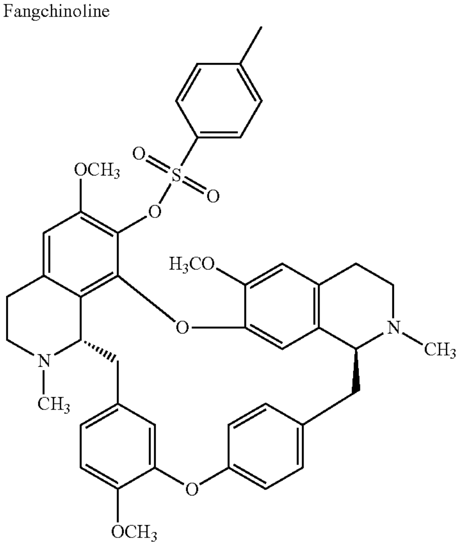

BS-FC-102 wherein DIPEA is N,N-diisopropylethylamine.

To dichloromethane (2 mL) were added fangchinoline (120 mg, 0.2 mmol) and paratoluenesulfonyl chloride (56 mg, 0.29 mmol), followed by N,N-diisopropylethylamine (51 mg, 0.39 mmol). The reaction solution was heated up to 40° C. and stirred for 2 hours. After the reaction was completed, the reaction solution was washed with saturated salt solution. The separated organic phase was dried with anhydrous sodium sulfate and rotavapped. The resulted crude product was separated and purified through preparative thin layer chromatography (dichloromethane: methanol=8:1) to give the bright yellow powdery compound BS-FC-102 (73 mg, yield 49%).

LC-MS: retention time: 1.11 min (95.24%); m/z 763 $[M+H]^+$, 382 $[½M+H]^+$.

$^1$H NMR (301 MHz, partial assignment of signals in $CDCl_3$) δ 1.23 (s, 3H, $CH_3$), 2.41 (s, 3H, N—$CH_3$), 2.90 (s, 3H, N—$CH_3$), 3.15 (s, 3H, $OCH_3$), 3.41 (s, 3H, $OCH_3$), 3.92 (s, 3H, 12-$OCH_3$), 5.84 (s, 1H, 8'-H), 6.17 (s, 1H, 5-H), 6.28 (d, 1H, J=9 Hz, 11'-H), 6.43 (s, 1H, H-benzene ring), 6.59 (s, 1H, H-benzene ring), 6.88 (m, 3H, H-benzene ring), 7.11-7.17 (m, 3H, H-benzene ring), 7.41-7.50 (m, 3H, H-benzene ring).

Compound BS-FC-104 was prepared by reacting fangchinoline with benzenesulfonyl chloride according to the process for preparing BS-FC-102 using the same reagents:

LC-MS: retention time: 0.99 min (100%); m/z 749.0 $[M+H]^+$, 374.9 $[½M+H]^+$.

Compound BS-FC-105 was prepared by reacting fangchinoline with trifluoromethylsulfonyl chloride according to the process for preparing BS-FC-102 using the same reagents:

LC-MS: retention time: 1.03 min (90.45%); m/z 741.0 $[M+H]^+$, 371.1 $[½M+H]^+$.

$^1H$ NMR (301 MHz, partial assignment of signals in $CDCl_3$) δ 2.73 (s, 3H, N—$CH_3$), 3.01 (s, 3H, N'—$CH_3$), 3.53 (s, 3H, 6'-$OCH_3$), 3.83 (s, 3H, 6-$OCH_3$), 3.96 (s, 3H, 12-$OCH_3$), 6.05 (s, 1H, 8'-H), 6.42 (m, 2H, H-benzene ring), 6.55 (s, 1H, H-benzene ring), 6.71 (s, 1H, H-benzene ring), 6.96 (m, 2H, 2H-benzene ring), 7.52 (m, 1H, 14'-H).

Example 2

The Synthesis of Compound BS-FC-206

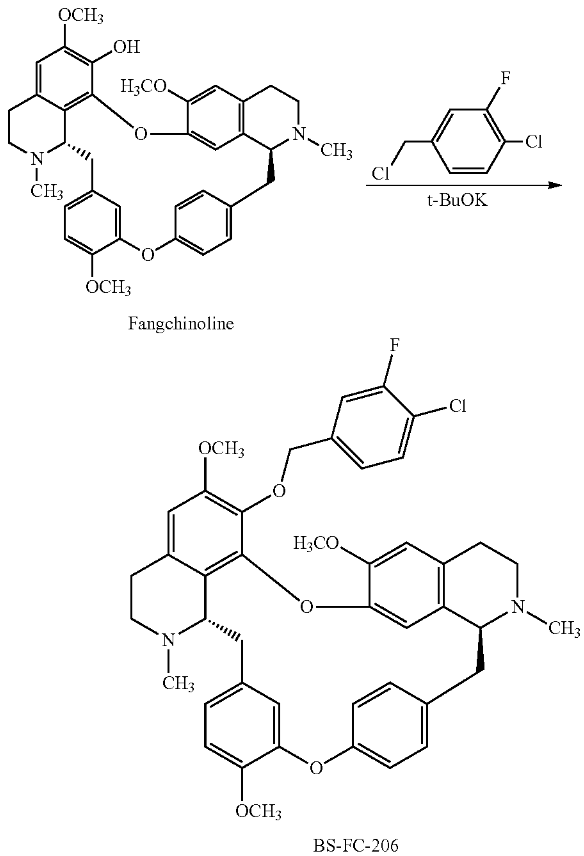

Fangchinoline

BS-FC-206 wherein: t-BuOK is potassium tert-butoxide.

To dimethylsulfoxide (2 mL) was added fangchinoline (80 mg, 0.13 mmol), followed by the addition of potassium tert-butoxide (22.5 mg, 0.1971 mmol) at 0° C. The reaction solution was warmed to room temperature and stirred for 0.5 hr. 3-fluoro-4-chloro benzyl chloride (26.5 mg, 0.12 mmol) dissolved in dimethylsulfoxide was added dropwise to the reaction solution. The reaction solution was heated up to 40° C. and stirred for 2 hr. After the reaction was completed, water (20 mL) was added to the reaction solution and dichloromethane (5 mL×3) was used for extraction. The organic phases were combined, washed with saturated salt solution and rotavapped. The resulted crude product was separated and purified through preparative thin layer chromatography (dichloromethane: methanol=10:1) to give the bright yellow powdery compound BS-FC-206 (23.6 mg, yield 24%).

LC-MS: retention time: 1.10 min (99.12%); m/z 751 $[M+H]^+$, 376 $[½M+H]^+$. $^1H$ NMR (301 MHz, partial assignment of signals in $CDCl_3$) δ 2.55 (s, 3H, N—$CH_3$), 3.48 (s, 3H, 6'-$OCH_3$), 3.76 (s, 3H, 6-$OCH_3$), 3.94 (s, 3H, 12-$OCH_3$), 5.81 (s, 1H, 8'-H), 6.60 (s, 1H, H-benzene ring), 6.74 (m, 1H, H-benzene ring).

Compound BS-FC-201 was prepared by reacting fangchinoline with parafluorobenzyl chloride according to the process for preparing BS-FC-206 using the same reagents:

LC-MS: retention time: 1.13 min (85.98%); m/z 717.0 $[M+H]^+$, 359.0 $[½M+H]^+$.

$^1H$ NMR (301 MHz, partial assignment of signals in $CDCl_3$) δ 2.53 (s, 3H, N—$CH_3$), 2.59 (s, 3H, N—$CH_3$), 3.41 (s, 3H, 6'-$OCH_3$), 3.61 (s, 3H, 6-$OCH_3$), 3.92 (s, 3H, 12-$OCH_3$), 5.77 (s, 1H, 8'-H), 6.36 (s, 1H, H-benzene ring), 6.46 (s, 1H, H-benzene ring), 6.53 (s, 1H, H-benzene ring), 6.78-6.89 (m, 5H, H-benzene ring), 7.11-7.36 (m, 3H, H-benzene ring).

Compound BS-FC-202 was prepared by reacting fangchinoline with 3-bromomethyl pyridine according to the process for preparing BS-FC-206 using the same reagents:

LC-MS: retention time: 0.79 min (92.16%); m/z 700.1 $[M+H]^+$, 350.5 $[½M+H]^+$.

Compound BS-FC-203 was prepared by reacting fangchinoline with paratrifluoro-methoxybenzyl bromide according to the process for preparing BS-FC-206 using the same reagents:

LC-MS: retention time: 1.21 min (94.06%); m/z 782.9 $[M+H]^+$, 392.0 $[½M+H]^+$.

$^1H$ NMR (301 MHz, partial assignment of signals in $CDCl_3$) δ 2.43 (s, 3H, N—$CH_3$), 2.52 (s, 3H, N—$CH_3$), 3.49 (s, 3H, 6'-$OCH_3$), 3.75 (s, 3H, 6-$OCH_3$), 3.94 (s, 3H, 12-$OCH_3$), 4.34 (d, 1H, J=8.1 Hz), 4.70 (d, 1H, J=8.1 Hz), 5.89 (s, 1H, 8'-H), 6.31 (d, 1H, J=8.4, 11'-H), 6.40 (s, 1H, H-benzene ring), 6.47 (s, 1H, H-benzene ring), 6.60 (s, 1H, H-benzene ring), 6.86 (d, 2H, J=8.7 Hz, H-benzene ring), 6.93 (m, 3H, H-benzene ring), 7.06 (d, 1H, J=8.4 Hz, 13'-H), 7.13 (d, 1H, J=8.1 Hz, 13'-H), 7.42 (d, 1H, J=8.1 Hz, 14'-H).

Compound BS-FC-204 was prepared by reacting fangchinoline with 2,3-difluorobenzyl bromide according to the process for preparing BS-FC-206 using the same reagents:

LC-MS: retention time: 1.11 min (99.35%); m/z 735.0 $[M+H]^+$, 368.0 $[½M+H]^+$.

$^1H$ NMR (301 MHz, partial assignment of signals in $CDCl_3$) δ 2.36 (s, 3H, N—$CH_3$), 2.55 (s, 3H, N—$CH_3$), 3.37 (s, 3H, 6'-$OCH_3$), 3.74 (s, 3H, 6-$OCH_3$), 3.92 (s, 3H, 12-$OCH_3$), 4.46 (d, 1H, J=8.1 Hz), 4.65 (d, 1H, J=8.1 Hz), 5.75 (s, 1H, 8'-H), 6.27 (d, 1H, J=8.4, 11'-H), 6.35 (s, 1H, H-benzene ring), 6.46 (s, 1H, H-benzene ring), 6.51 (s, 1H, H-benzene ring), 6.86 (m, 2H, H-benzene ring), 6.95-7.13 (m, 4H, H-benzene ring), 7.15 (dd, 1H, J=2.1, 8.1 Hz, 13'-H), 7.36 (dd, 1H, J=2.1, 8.1 Hz, 14'-H).

Compound BS-FC-205 was prepared by reacting fangchinoline with 3-chloro-4-fluorobenzyl bromide according to the process for preparing BS-FC-206 using the same reagents:

LC-MS: retention time: 1.09 min (96.28%); m/z 751.2 $[M+H]^+$, 376.2 $[½M+H]^+$.

$^1H$ NMR (301 MHz, partial assignment of signals in $CDCl_3$) δ 2.41 (s, 3H, N—$CH_3$), 2.61 (s, 3H, N'—$CH_3$), 3.41 (s, 3H, 6'-$OCH_3$), 3.75 (s, 3H, 6-$OCH_3$), 3.94 (s, 3H, 12-$OCH_3$), 5.79 (s, 1H, 8'-H), 6.32 (m, 1H, 11'-H), 6.36 (s, 1H, 5-H), 6.49 (s, 1H, H-benzene ring), 6.54 (s, 1H, H-benzene ring), 6.82-6.99 (m, 3H, H-benzene ring), 7.11 (m, 2H, H-benzene ring), 7.34 (m, 1H, 14'-H).

Compound BS-FC-208 was prepared by reacting fangchinoline with bromomethyl cyclopropane according to the process for preparing BS-FC-206 using the same reagents:

LC-MS: retention time: 1.06 min (95.93%); m/z 663.0 $[M+H]^+$, 332.0 $[½M+H]^+$.

$^1H$ NMR (301 MHz, partial assignment of signals in $CDCl_3$) δ 2.71 (s, 3H, N'—$CH_3$), 3.41 (s, 3H, 6'-$OCH_3$), 3.75 (s, 3H, 6-$OCH_3$), 3.94 (s, 3H, 12-$OCH_3$), 5.79 (s, 1H, 8'-H).

Compound BS-FC-213 was prepared by reacting fangchinoline with bromopropylene according to the process for preparing BS-FC-206 using the same reagents:

LC-MS: retention time: 1.04 min (97.48%); m/z 649.1 $[M+H]^+$, 324.9 $[½M+H]^+$.

$^1H$ NMR (301 MHz, partial assignment of signals in $CDCl_3$) δ 2.39 (s, 3H, N—$CH_3$), 2.62 (s, 3H, N'—$CH_3$), 3.39 (s, 3H, 6'-$OCH_3$), 3.75 (s, 3H, 6-$OCH_3$), 3.93 (s, 3H, 12-$OCH_3$), 5.97 (s, 1H, 8'-H), 6.30 (m, 2H, H-benzene ring), 6.53 (m, 2H, H-benzene ring), 6.87 (m, 3H, H-benzene ring), 7.15 (m, 1H, 13'-H), 7.38 (m, 1H, 14'-H).

Compound BS-FC-215 was prepared by reacting fangchinoline with paramethoxybenzyl bromide according to the process for preparing BS-FC-206 using the same reagents:

LC-MS: retention time: 1.03 min (89.37%); m/z 729.2 $[M+H]^+$, 365.1 $[½M+H]^+$.

$^1H$ NMR (301 MHz, partial assignment of signals in $CDCl_3$) δ 2.56 (s, 3H, N—$CH_3$), 3.38 (s, 3H, 6'-$OCH_3$), 3.75 (s, 6H, $OCH_3$), 3.93 (s, 3H, 12-$OCH_3$), 5.79 (s, 1H, 8'-H), 6.39 (m, 1H, H-benzene ring), 6.51 (m, 2H, H-benzene ring), 6.79 (m, 1H, H-benzene ring), 6.91 (m, H-benzene ring).

Compound BS-FC-216 was prepared by reacting fangchinoline with paratrifluoro methoxybenzyl bromide according to the process for preparing BS-FC-206 using the same reagents:

LC-MS: retention time: 1.08 min (94.44%); m/z 767.1 $[M+H]^+$, 384.0 $[½M+H]^+$.

Compound BS-FC-217 was prepared by reacting fangchinoline with 6-chloro-2-fluorobenzyl bromide according to the process for preparing BS-FC-206 using the same reagents:

LC-MS: retention time: 1.06 min (95.06%); m/z 751.2 $[M+H]^+$, 376.2 $[½M+H]^+$.

$^1H$ NMR (301 MHz, partial assignment of signals in $CDCl_3$) δ 2.46 (s, 3H, N—$CH_3$), 2.76 (s, 3H, N'—$CH_3$), 3.34 (s, 3H, 6'-$OCH_3$), 3.79 (s, 3H, 6-$OCH_3$), 3.93 (s, 3H, 12-$OCH_3$), 6.26 (m, 1H, 11'-H), 6.34 (s, 1H, 5-H), 6.44 (s, 1H, H-benzene ring), 6.50 (s, 1H, H-benzene ring), 6.74 (m, 1H, 10'-H), 6.80 (m, 2H, H-benzene ring), 7.16 (m, 3H, H-benzene ring), 7.40 (m, 2H, H-benzene ring).

Compound BS-FC-220 was prepared by reacting fangchinoline with iodocyclopentane according to the process for preparing BS-FC-206 using the same reagents:

LC-MS: retention time: 1.00 min (99.74%); m/z 677.1 $[M+H]^+$, 339.0 $[½M+H]^+$.

$^1H$ NMR (301 MHz, partial assignment of signals in $CDCl_3$) δ 2.42 (s, 3H, N—$CH_3$), 2.72 (s, 3H, N'—$CH_3$), 3.37 (s, 3H, 6'-$OCH_3$), 3.74 (s, 3H, 6-$OCH_3$), 3.93 (s, 3H, 12-$OCH_3$), 5.89 (s, 1H, 8'-H), 6.35 (m, 2H, H-benzene ring), 6.51 (s, 1H, H-benzene ring), 6.53 (s, 1H, H-benzene ring), 6.83 (m, 1H, H-benzene ring), 6.89 (d, 1H, J=8.1 Hz, H-benzene ring), 7.16 (dd, 1H, J=2.1, 8.1 Hz, 13'-H), 7.42 (dd, 1H, J=2.1, 8.1 Hz, 14'-H).

Compound BS-FC-221 was prepared by reacting fangchinoline with 3-bromo-2-methylpropylene using the same reagents as above according to the process for preparing BS-FC-206:

LC-MS: retention time: 1.00 min (99.72%); m/z 663.2 $[M+H]^+$, 332.0 $[½M+H]^+$.

Example 3

The Synthesis of Compound BS-FC-304

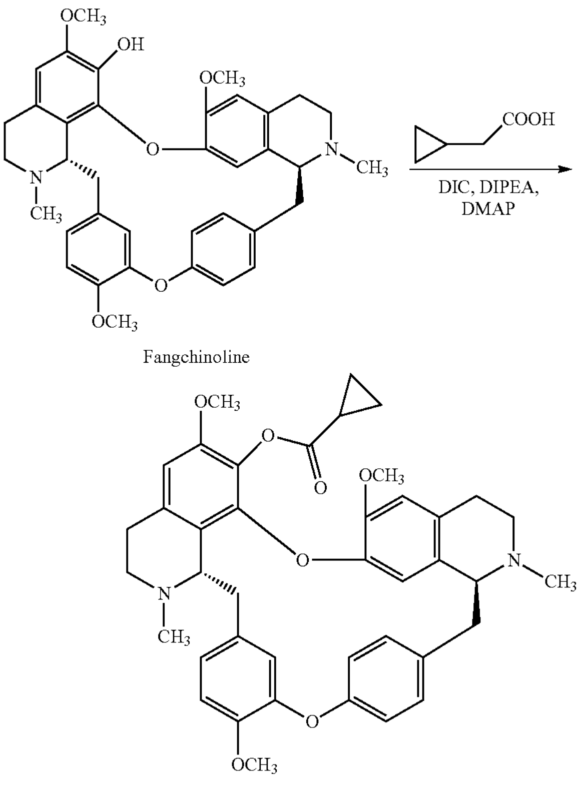

Fangchinoline

BS-FC-304 wherein: DIC is N,N'-diisopropylcarbodiimide; DMAP is 4-dimethylaminopyridine.

To dichloromethane (2 mL) were added fangchinoline (80 mg, 0.13 mmol) and cyclopropanecarboxylic acid (17 mg, 0.2 mmol), followed by N,N'-diisopropylcarbodiimide (34 mg, 0.26 mmol), 4-dimethylaminopyridine (16 mg, 0.26 mmol) and N,N-diisopropylethylamine (34 mg, 0.26 mmol). The reaction solution was heated up to 40° C. and stirred for 2 hours. After the reaction was completed, dichloromethane (20 mL) was added to the reaction solution, which was then washed with saturated salt solution. The separated organic phase was dried with anhydrous sodium sulfate and rotavapped. The resulted crude product was separated and purified through preparative thin layer chromatography to give an off-white powdery compound BS-FC-304 (54.7 mg, yield 52%).

LC-MS: retention time: 0.80 min (100.0%); m/z 677 $[M+H]^+$, 338 $[½M+H]$+.

$^1H$ NMR (301 MHz, partial assignment of signals in $CDCl_3$) δ 2.52 (s, 3H, N—$CH_3$), 2.77 (s, 3H, N—$CH_3$), 3.45 (s, 3H, 6'-$OCH_3$), 3.85 (s, 3H, 6-$OCH_3$), 3.93 (s, 3H, 12-$OCH_3$), 5.99 (s, 1H, 8'-H), 6.29 (m, 1H, 11'-H), 6.40 (s, 1H, H-benzene ring), 6.48 (s, 1H, H-benzene ring), 6.56 (s, 1H, H-benzene ring), 6.87 (m, 1H, H-benzene ring), 6.90 (d, 1H, J=8.1 Hz, H-benzene ring), 6.95-7.13 (m, 4H, H-benzene ring), 7.13 (d, 1H, J=8.7 Hz, 13'-H), 7.36 (d, 1H, J=8.7 Hz, 14'-H).

Compound BS-FC-301 was prepared by reacting fangchinoline with 3-pyridine carboxylic acid according to the process for preparing BS-FC-304 using the same reagents:

LC-MS: retention time: 0.92 min (96.55%); m/z 714.2 $[M+H]^+$, 357.6 $[½M+H]^+$.

$^1H$ NMR (301 MHz, partial assignment of signals in $CDCl_3$) δ 3.73 (s, 3H, 6-$OCH_3$), 3.95 (s, 3H, 12-$OCH_3$), 6.45 (s, 2H, H-benzene ring), 6.90-7.12 (m, 3H, H-benzene ring), 7.35 (m, 1H, H-benzene ring).

Compound BS-FC-302 was prepared by reacting fangchinoline with 4-pyridinecarboxylic acid according to the process for preparing BS-FC-304 using the same reagents:

LC-MS: retention time: 0.96 min (98.29%); m/z 714.0 $[M+H]^+$, 357.5 $[½M+H]^+$.

$^1H$ NMR (301 MHz, partial assignment of signals in $CDCl_3$) δ 2.03 (s, 3H, N—$CH_3$), 2.53 (s, 3H, N'—$CH_3$), 3.48 (s, 3H, 6'-$OCH_3$), 3.71 (s, 3H, 6-$OCH_3$), 3.93 (s, 3H, 12-$OCH_3$), 6.46 (s, 2H, H-benzene ring), 6.79 (m, 1H, H-benzene ring), 6.90 (m, 1H, H-benzene ring), 7.09-7.29 (m, 2H, H-benzene ring), 8.69 (m, 2H).

Compound BS-FC-305 was prepared by reacting fangchinoline with N-methyl-D-alanine according to the process for preparing BS-FC-304 using the same reagents:

LC-MS: retention time: 0.75 min (99.65%); m/z 694.2 $[M+H]^+$, 347.5 $[½M+H]^+$.

Compound BS-FC-307 was prepared by reacting fangchinoline with N,N-dimethylglycine according to the process for preparing BS-FC-304 using the same reagents:

LC-MS: retention time: 0.92 min (95.29.00%); m/z 694.0 $[M+H]^+$.

Compound BS-FC-308 was prepared by reacting fangchinoline with N,N-dimethyl aminobenzoic acid according to the process for preparing BS-FC-304 using the same reagents:

LC-MS: retention time: 1.13 min (91.31%); m/z 756.0 $[M+H]^+$, 378.5 $[½M+H]^+$.

Compound BS-FC-309 was prepared by reacting fangchinoline with paratrifluoromethoxy benzoic acid according to the process for preparing BS-FC-304 using the same reagents:

LC-MS: retention time: 1.15 min (91.13%); m/z 797.2 $[M+H]^+$, 399.2 $[½M+H]^+$.

$^1H$ NMR (301 MHz, partial assignment of signals in $CDCl_3$) δ 2.07 (s, 3H, N—$CH_3$), 2.39 (m, 3H, N—$CH_3$), 3.54 (s, 3H, 6'-$OCH_3$), 3.72 (s, 3H, 6-$OCH_3$), 3.95 (s, 3H, 12-$OCH_3$), 6.42 (s, 2H, H-benzene ring), 6.87 (m, 2H, H-benzene ring), 7.10 (m, 1H, H-benzene ring), 7.17 (m, 1H, H-benzene ring), 7.20 (m, 1H, H-benzene ring), 7.66 (m, 1H, H-benzene ring).

Compound BS-FC-310 was prepared by reacting fangchinoline with 3,5-difluorobenzoic acid according to the process for preparing BS-FC-304 using the same reagents:

LC-MS: retention time: 1.11 min (98.02%); m/z 748.9 $[M+H]^+$, 374.9 $[½M+H]^+$.

$^1H$ NMR (301 MHz, partial assignment of signals in $CDCl_3$) δ 2.12 (s, 3H, N—$CH_3$), 2.23 (s, 3H, N—$CH_3$), 3.67 (s, 3H, 6-$OCH_3$), 3.90 (s, 3H, 12-$OCH_3$), 6.37 (s, 1H, H-benzene ring), 6.86 (m, 3H, H-benzene ring).

Compound BS-FC-311 was prepared by reacting fangchinoline with 3,5-dimethoxybenzoic acid according to the process for preparing BS-FC-304 using the same reagents:

LC-MS: retention time: 1.11 min (99.22%); m/z 773.0 $[M+H]^+$, 387.0 $[½M+H]^+$.

Compound BS-FC-313 was prepared by reacting fangchinoline with 4-pyridazine carboxylic acid u according to the process for preparing BS-FC-304 sing the same reagents:

LC-MS: retention time: 0.89 min (95.53%); m/z 715.1 $[M+H]^+$, 358.1 $[½M+H]^+$.

Compound BS-FC-314 was prepared by reacting fangchinoline with tetrahydropyran-4-carboxylic acid according to the process for preparing BS-FC-304 using the same reagents:

LC-MS: retention time: 0.89 min (97.72%); m/z 721.1 $[M+H]^+$, 361.0 $[½M+H]^+$.

Compound BS-FC-315 was prepared by reacting fangchinoline with 6-chloro-2-fluorobenzoic acid according to the process for preparing BS-FC-304 using the same reagents:

LC-MS: retention time: 1.04 min (99.51%); m/z 765.2 $[M+H]^+$, 383.2 $[½M+H]^+$.

$^1H$ NMR (301 MHz, partial assignment of signals in $CDCl_3$) δ 2.38 (s, 3H, N—$CH_3$), 3.47 (s, 3H, 6'-$OCH_3$), 3.69 (s, 3H, 6-$OCH_3$), 3.94 (s, 3H, 12-$OCH_3$), 6.03 (s, 1H, 8'-H), 6.50 (m, 3H, H-benzene ring).

Compound BS-FC-318 was prepared by reacting fangchinoline with carbamic acid according to the process for preparing BS-FC-304 using the same reagents:

LC-MS: retention time: 0.73 min (95.42%); m/z 666.1 $[M+H]^+$, 333.5 $[½M+H]^+$.

Compound BS-FC-324 was prepared by reacting fangchinoline with glutaric anhydride according to the process for preparing BS-FC-304 using the same reagents:

LC-MS: retention time: 0.97 min (98.81%); m/z 723.0 $[M+H]^+$, 362.0 $[½M+H]^+$.

$^1H$ NMR (301 MHz, partial assignment of signals in $CDCl_3$) δ 2.84 (s, 3H, N'—$CH_3$), 3.50 (s, 3H, 6'-$OCH_3$), 3.73 (s, 3H, 6-$OCH_3$), 3.95 (s, 3H, 12-$OCH_3$), 6.00 (s, 1H, 8'-H), 6.30 (m, 2H, H-benzene ring), 6.36 (m, 1H, H-benzene ring), 6.40 (m, 1H, H-benzene ring), 6.56 (m, 1H, H-benzene ring), 6.90 (s, 2H, H-benzene ring), 7.25-7.37 (m, 3H, H-benzene ring).

Compound BS-FC-501 was prepared by reacting fangchinoline with benzoic acid according to the process for preparing BS-FC-304 using the same reagents:

LC-MS: retention time: 2.30 min (96.19%); m/z 713.0 $[M+H]^+$, 357.1 $[½M+H]^+$.

$^1H$ NMR (301 MHz, partial assignment of signals in $CDCl_3$) δ 1.87 (s, 3H), 2.49 (s, 3H), 2.73-2.62 (m, 2H), 2.90 (s, 3H), 3.54 (d, 4H), 3.71 (dd, J=8.6, 5.2 Hz, 10H), 3.76 (s, 1H), 3.93 (s, 3H), 6.84 (dd, 9H, H-benzene ring), 7.87-7.30 (m, 6H, H-benzene ring).

Compound BS-FC-502 was prepared by reacting fangchinoline with paramethylbenzoic acid according to the process for preparing BS-FC-304 using the same reagents:

LC-MS: retention time: 2.44 min (97.24%); m/z 727.1 $[M+H]^+$, 364.2 $[½M+H]^+$.

$^1H$ NMR (301 MHz, partial assignment of signals in $CDCl_3$) δ 1.25 (s, 1H), 1.32 (s, 1H), 1.96-1.87 (m, 2H), 2.36 (s, 6H), 3.06-2.44 (m, 9H), 3.21 (s, 1H), 3.51 (t, 6H), 3.68 (s, 3H), 3.92 (s, 3H), 7.20-5.66 (m, 12H, H-benzene ring), 7.75-7.41 (m, 2H, H-benzene ring).

Compound BS-FC-503 was prepared by reacting fangchinoline with paramethoxybenzoic acid according to the process for preparing BS-FC-304 using the same reagents:

LC-MS: retention time: 2.36 min (95.46%); m/z 743.0 $[M+H]^+$, 372.1 $[½M+H]^+$.

$^1H$ NMR (301 MHz, partial assignment of signals in $CDCl_3$) δ 2.03 (s, 4H), 2.39 (s, 3H), 2.84-2.50 (m, 7H), 3.00 (s, 2H), 3.24 (s, 1H), 3.52 (t, 6H), 3.69 (s, 3H), 3.83 (s, 3H), 3.92 (s, 3H), 7.18-5.69 (m, 12H, H-benzene ring), 7.66 (d, 2H, H-benzene ring).

Compound BS-FC-504 was prepared by reacting fangchinoline with paramethylamino benzoic acid according to the process for preparing BS-FC-304 using the same reagents:

LC-MS: retention time: 2.32 min (100%); m/z 742.0 $[M+H]^+$, 372.0 $[½M+H]^+$.

$^1H$ NMR (301 MHz, partial assignment of signals in $CDCl_3$) δ 2.05 (s, 3H), 2.17 (s, 3H), 3.27-2.38 (m, 15H), 3.48 (s, 1H), 3.63 (s, 1H), 3.69 (s, 3H), 3.87-3.72 (m, 3H), 3.92 (s, 3H), 7.23-5.72 (m, 10H, H-benzene ring), 8.12-7.31 (m, 4H, H-benzene ring).

Compound BS-FC-505 was prepared by reacting fangchinoline with 4-(diethylamino) benzoic acid according to the process for preparing BS-FC-304 using the same reagents:

LC-MS: retention time: 2.66 min (92.21%); m/z 784.1 $[M+H]^+$, 392.6 $[½M+H]^+$.

$^1H$ NMR (301 MHz, partial assignment of signals in $CDCl_3$) δ 1.18 (t, J=7.0 Hz, 6H), 7.60 (dddd, 4H), 1.39-1.27 (m, 4H), 1.67 (dd, 1H), 2.36 (s, 3H), 2.65 (dd, 5H), 2.98 (dd, 2H), 3.45 (dd, 6H), 3.67 (s, 3H), 3.90 (d, J=16.6 Hz, 3H), 4.31-4.11 (m, 1H), 7.25-5.53 (m, 10H, H-benzene ring).

Compound BS-FC-506 was prepared by reacting fangchinoline with paraisopropylbenzoic acid according to the process for preparing BS-FC-304 using the same reagents:

LC-MS: retention time: 2.72 min (99.20%); m/z 755.0 $[M+H]^+$, 378.0 $[½M+H]^+$.

$^1H$ NMR (301 MHz, partial assignment of signals in $CDCl_3$) δ 1.26-1.17 (m, 9H), 2.02-1.52 (m, 4H), 3.08-2.40 (m, 13H), 3.48 (s, 1H), 3.63 (s, 2H), 3.68 (s, 3H), 3.93 (s, 3H), 4.34-4.09 (m, 1H), 7.24-5.38 (m, 11H, H-benzene ring), 8.25-7.29 (m, 3H, H-benzene ring).

Compound BS-FC-507 was prepared by reacting fangchinoline with paraminobenzoic acid according to the process for preparing BS-FC-304 using the same reagents:

LC-MS: retention time: 2.16 min (100%); m/z 728.0 $[M+H]^+$, 364.0 $[½M+H]^+$.

$^1H$ NMR (301 MHz, partial assignment of signals in $CDCl_3$) δ 1.42-1.26 (m, 9H), 1.79-1.59 (m, 2H), 2.80-2.48 (m, 4H), 3.04 (s, 3H), 3.56 (d, 3H), 3.77-3.67 (m, 3H), 3.95 (d, 3H), 4.25-4.18 (m, 3H), 6.60-5.69 (m, 4H, H-benzene ring), 6.83 (dd, 2H, H-benzene ring), 7.13 (s, 1H, H-benzene ring), 7.34 (d, J=8.1 Hz, 1H, H-benzene ring), 7.65-7.42 (m, 3H, H-benzene ring), 7.70 (dd, J=5.7, 3.3 Hz, 1H, H-benzene ring), 8.23-8.02 (m, 1H, H-benzene ring).

Example 4

The Synthesis of Compound BS-FC-400

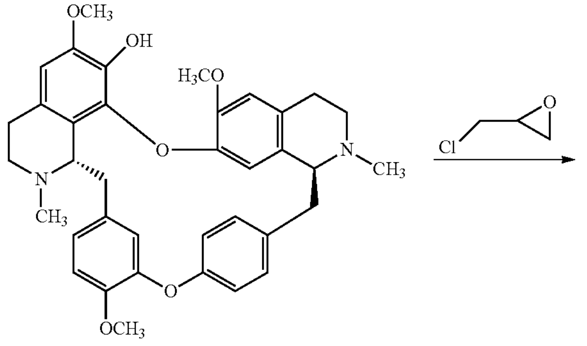

Fangchinoline

-continued

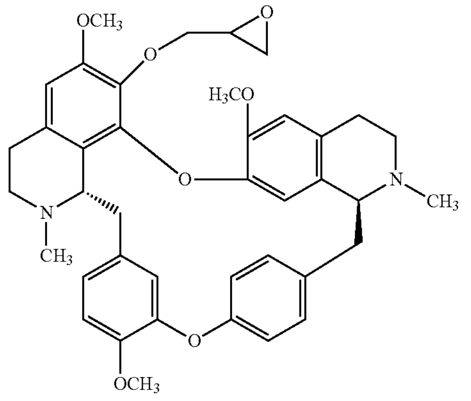

BS-FC-400

Fangchinoline (1 g, 1.64 mmol) was added to dimethylsulfoxide (5 mL), followed by the addition of potassium tert-butoxide (560 mg, 4.91 mmol) at 0° C. After the mixed solution was stirred for 0.5 hr at room temperature, cyclochloroethane (180 mg, 1.97 mmol) dissolved in dimethylsulfoxide (2 mL) was added dropwise thereto. The reaction solution was heated up to 40° C. and stirred for 3 hr. After the reaction was complete, water (50 mL) was added to the reaction solution at 0° C. and dichloromethane (10 mL*4) was used for extraction. The organic phases were combined, washed with saturated salt solution, dried and rotavapped. The resulted product BS-FC-400 was directly used in the subsequent reaction without purification.

LC-MS: retention time: 0.88 min (92.01%); m/z 665.0 $[M+H]^+$, 333.1 $[12M+H]^+$.

$^1H$ NMR (301 MHz, partial assignment of signals in $CDCl_3$) δ 2.38 (s, 3H, N—$CH_3$), 2.70 (s, 3H, N'—$CH_3$), 3.38 (s, 3H, 6'-$OCH_3$), 3.70 (s, 3H, 6-$OCH_3$), 3.90 (s, 3H, 12-$OCH_3$), 6.00 (m, 1H, 8'-H), 6.24 (m, 2H, H-benzene ring), 6.46 (m, 2H, H-benzene ring), 6.86-7.00 (m, 3H, H-benzene ring), 7.11 (m, 1H, 13'-H), 7.36 (m, 1H, 14'-H).

Example 5

The Synthesis of Compound BS-FC-418

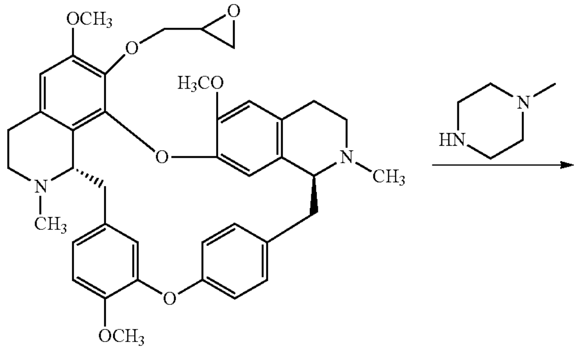

BS-FC-400

-continued

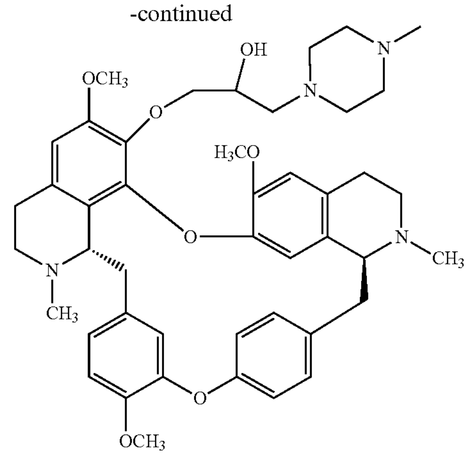

BS-FC-418

Compound BS-FC-400 (100 mg, 0.15 mmol) obtained from the last step was added to ethanol (2 mL), followed by the addition of N-methyl-piperazine (30 mg, 0.3 mmol). Under airtight conditions, the reaction solution was heated up to 120° C. and reacted for 3 hr. After the reaction was completed, the reaction solution was concentrated to give a crude product, which was then separated and purified through preparative thin layer chromatography (dichloromethane: methanol=8:1) to give the white powdery compound BS-FC-418 (30 mg, yield 26%).

LC-MS: retention time: 0.7 min (96%); m/z 764.9 $[M+H]^+$. 383.2 $[½M+H]^+$.

$^1H$ NMR (301 MHz, partial assignment of signals in $CDCl_3$) δ 2.34-2.15 (m, 10H), 2.59-2.40 (m, 10H), 2.65 (t, J=4.4 Hz, 4H), 2.80-2.70 (m, 3H), 2.96-2.83 (m, 4H), 3.36-3.22 (m, 6H), 3.45-3.37 (m, 2H), 3.58-3.45 (m, 3H), 3.73 (t, J=3.2 Hz, 5H), 3.91 (s, 5H), 5.98 (d, J=2.2 Hz, 1H), 6.32-6.27 (m, 2H), 6.52-6.47 (m, 2H), 6.88-6.77 (m, 3H), 7.13 (dd, J=8.2, 2.4 Hz, 1H), 7.34 (dt, J=8.1, 2.5 Hz, 1H).

Compound BS-FC-401 was prepared by reacting compound BS-FC-4 with 4-dimethylamino pyridine according to the process for preparing BS-FC-418 using the same reagents:

LC-MS: retention time: 0.71 min (95.72%); m/z 793.1 $[M+H]^+$, 397.4 $[½M+H]^+$.

$^1H$ NMR (301 MHz, partial assignment of signals in $CDCl_3$) δ 2.30 (s, 3H, N—$CH_3$), 2.38 (s, 6H, N—$(CH_3)_2$) 2.64 (s, 3H, N'—$CH_3$), 3.35 (s, 3H, 6'-$OCH_3$), 3.74 (s, 3H, 6-$OCH_3$), 3.92 (s, 3H, 12-$OCH_3$), 5.98 (s, 1H, 8'-H), 6.30 (m, 2H, H-benzene ring), 6.52 (m, 2H, H-benzene ring), 6.84-6.86 (m, 3H, H-benzene ring), 7.14 (m, 1H, 13'-H), 7.34 (m, 1H, 14'-H).

Compound BS-FC-402 was prepared by reacting compound BS-FC-4 with 3-hydroxy piperidine according to the process for preparing BS-FC-418 using the same reagents:

LC-MS: retention time: 0.74 min (93.36%); m/z 766.1 $[M+H]^+$, 383.8 $[½M+H]^+$.

$^1H$ NMR (301 MHz, partial assignment of signals in $CDCl_3$) δ 2.29 (s, 3H, N—$CH_3$), 3.33 (s, 3H, 6'-$OCH_3$), 3.70 (s, 3H, 6-$OCH_3$), 3.89 (s, 3H, 12-$OCH_3$), 6.03 (m, 1H, 8'-H), 6.27 (m, 2H, 5, 11'-H), 6.46 (m, 1H, H-benzene ring), 6.52 (m, 1H, H-benzene ring), 6.80 (m, 3H, H-benzene ring), 7.12 (m, 1H, 13'-H), 7.34 (m, 1H, 14'-H).

Compound BS-FC-403 was prepared by reacting compound BS-FC-4 with piperidine according to the process for preparing BS-FC-418 using the same reagents:

LC-MS: retention time: 0.75 min (88.00%); m/z 750.0 $[M+H]^+$, 375.7 $[½M+H]^+$.

$^1H$ NMR (301 MHz, partial assignment of signals in $CDCl_3$) δ 2.30 (s, 3H, N—$CH_3$), 2.62 (s, 3H, N'—$CH_3$), 3.34 (s, 3H, 6'-$OCH_3$), 3.71 (s, 3H, 6-$OCH_3$), 3.92 (s, 3H, 12-$OCH_3$), 5.97 (s, 1H, 8'-H), 6.25 (m, 2H, H-benzene ring), 6.48 (m 211, H-benzene ring), 6.77 (m, 3H, H-benzene ring), 7.09 (m, 1H, 13'-H), 7.33 (m, 1H, 14'-H).

Compound BS-FC-404 was prepared by reacting compound BS-FC-4 with N-isopropyl piperazine according to the process for preparing BS-FC-418 using the same reagents:

LC-MS: retention time: 0.73 min (95.62%); m/z 793.1 $[M+H]^+$, 397.4 $[½M+H]^+$.

$^1H$ NMR (301 MHz, partial assignment of signals in $CDCl_3$) δ 1.16 (m, 6H, $CH_3$), 2.29 (s, 3H, N—$CH_3$), 2.67 (s, 3H, N'—$CH_3$), 3.39 (s, 3H, 6'-$OCH_3$), 3.70 (s, 3H, 6-$OCH_3$), 389 (s, 3H, 12-$OCH_3$), 5.98 (m, 1H, 8'-H), 6.24 (m, 2H, H-benzene ring), 6.48 (m, 2H, H-benzene ring), 6.86 (m, 3H, H-benzene ring), 7.11 (m, 1H, 13'-H), 7.33 (m, 1H, 14'-H).

Compound BS-FC-405 was prepared by reacting compound BS-FC-4 with cyclopropane methylamine according to the process for preparing BS-FC-418 using the same reagents:

LC-MS: retention time: 0.78 min (96.5%); m/z 736.1 $[M+H]^+$, 368.8 $[½M+H]^+$.

$^1H$ NMR (301 MHz, partial assignment of signals in $CDCl_3$) δ 2.32 (s, 3H, N—$CH_3$), 2.91 (m, 3H, N'—$CH_3$), 3.38 (s, 3H, 6'-$OCH_3$), 3.68 (s, 3H, 6-$OCH_3$), 3.90 (s, 3H, 12-$OCH_3$), 6.08 (d, 1H, 8'-H), 6.29 (m, 2H, H-benzene ring), 6.50 (s, 2H, H-benzene ring), 6.76 (m, 1H, 10'-H), 6.83 (m, 2H, H-benzene ring), 7.14 (m, 1H, 13'-H), 7.34 (m, 1H, 14'-H).

Compound BS-FC-406 was prepared by reacting compound BS-FC-4 with N-ethylmethylamine according to the process for preparing BS-FC-418 using the same reagents:

LC-MS: retention time: 0.72 min (86.27%); m/z 723.9 $[M+H]^+$, 362.7 $[½M+H]^+$.

Compound BS-FC-407 was prepared by reacting compound BS-FC-4 with N-methylethanolamine according to the process for preparing BS-FC-418 using the same reagents:

LC-MS: retention time: 0.73 min (93.23%); m/z 740.1 $[M+H]^+$, 370.8 $[½M+H]^+$.

$^1H$ NMR (301 MHz, partial assignment of signals in $CDCl_3$) δ 2.28 (s, 3H, N—$CH_3$), 2.38 (s, 3H, N—$CH_3$), 2.68 (m, 3H, N—$CH_3$), 3.35 (s, 3H, 6'-$OCH_3$), 3.73 (s, 3H, 6-$OCH_3$), 3.91 (s, 3H, 12-$OCH_3$), 6.02 (m, 1H, 8'-H), 6.28 (m, 2H, H-benzene ring), 6.45 (m, 1H, 10-H), 6.52 (s, 1H, 5'-H), 6.84 (m, 3H, H-benzene ring), 7.13 (m, 1H, 13'-H), 7.34 (m, 1H, 14'-H).

Compound BS-FC-408 was prepared by reacting compound BS-FC-4 with N-methylhomopiperazine according to the process for preparing BS-FC-418 using the same reagents:

LC-MS: retention time: 0.69 min (94.45%); m/z 779.0 $[M+H]^+$, 390.2 $[½M+H]^+$.

$^1H$ NMR (301 MHz, partial assignment of signals in $CDCl_3$) δ 2.31 (s, 3H, N—$CH_3$), 2.39 (s, 3H, N—$CH_3$), 2.53 (m, 3H, N—$CH_3$), 3.34 (s, 3H, 6'-$OCH_3$), 3.72 (s, 3H, 6-$OCH_3$), 3.89 (s, 3H, 12-$OCH_3$), 6.01 (d, 1H, J=8.1 Hz, 8'-H), 6.29 (m, 2H, H-benzene ring), 6.49 (m, 2H, H-benzene ring), 6.76-6.83 (m, 3H, H-benzene ring), 7.13 (m, 1H, 13'-H), 7.34 (m, 1H, 14'-H).

Compound BS-FC-409 was prepared by reacting compound BS-FC-4 with N-allylmethylamine according to the process for preparing BS-FC-418 using the same reagents:

LC-MS: retention time: 0.76 min (91.38%); m/z 736.1 $[M+H]^+$, 368.8 $[½M+H]^+$.

$^1$H NMR (301 MHz, partial assignment of signals in $CDCl_3$) δ 2.33 (s, 6H, N—$CH_3$), 2.60 (m, 3H, N—$CH_3$), 3.35 (s, 3H, 6'-$OCH_3$), 3.73 (s, 3H, 6-$OCH_3$), 3.91 (s, 3H, 12-$OCH_3$), 6.02 (s, 1H, 8'-H), 6.30 (m, 2H, H-benzene ring), 6.50 (m, 2H, H-benzene ring), 6.79-6.88 (m, 1H, H-benzene ring), 7.13 (m, 1H, 13'-H), 7.34 (m, 1H, 14'-H).

Compound BS-FC-410 was prepared by reacting compound BS-FC-4 with 3-methylpiperidine according to the process for preparing BS-FC-418 using the same reagents:

LC-MS: retention time: 0.80 min (100.00%); m/z 764.1 $[M+H]^+$, 382.9 $[½M+H]^+$.

$^1$H NMR (301 MHz, partial assignment of signals in $CDCl_3$) δ 2.28 (s, 6H, N—$CH_3$), 2.61 (m, 3H, N—$CH_3$), 3.25 (s, 3H, 6'-$OCH_3$), 3.64 (s, 3H, 6-$OCH_3$), 3.90 (s, 3H, 12-$OCH_3$), 5.99 (s, 1H, 8'-H), 6.27 (m, 2H, H-benzene ring), 6.50 (m, 2H, H-benzene ring), 6.75-6.83 (m, 3H, H-benzene ring), 7.12 (m, 1H, 13'-H), 7.31 (m, 1H, 14'-H).

Compound BS-FC-413 was prepared by reacting compound BS-FC-4 with trifluoroethylamine according to the process for preparing BS-FC-418 using the same reagents:

LC-MS: retention time: 0.70 min (81.20%); m/z 763.8 $[M+H]^+$, 382.7 $[½M+H]^+$.

Compound BS-FC-414 was prepared by reacting compound BS-FC-4 with ethanolamine according to the process for preparing BS-FC-418 using the same reagents:

LC-MS: retention time: 0.71 min (80.58%); m/z 725.9 $[M+H]^+$, 363.7 $[½M+H]^+$.

$^1$H NMR (301 MHz, partial assignment of signals in $CDCl_3$) δ 2.32 (s, 3H, N—$CH_3$), 2.69 (m, 3H, N—$CH_3$), 3.35 (s, 3H, 6'-$OCH_3$), 3.72 (s, 3H, 6-$OCH_3$), 3.91 (s, 3H, 12-$OCH_3$), 6.02 (d, 1H, J=8.7 Hz, 8'-H), 6.28 (m, 2H, H-benzene ring), 6.48 (s, 1H, H-benzene ring), 6.52 (d, 1H, J=1.8 Hz, H-benzene ring), 6.85 (m, 3H, H-benzene ring), 7.11 (m, 1H, 13'-H), 7.36 (m, 1H, 14'-H).

Compound BS-FC-416 was prepared by reacting compound BS-FC-4 with morpholine according to the process for preparing BS-FC-418 using the same reagents:

LC-MS: retention time: 0.75 min (90.99%); m/z 752.1 $[M+H]^+$, 376.8 $[½M+H]^+$.

$^1$H NMR (301 MHz, partial assignment of signals in $CDCl_3$) δ 2.32 (s, 3H, N—$CH_3$), 2.63 (m, 3H, N'—$CH_3$), 3.36 (s, 3H, 6'-$OCH_3$), 3.66 (s, 3H, 6-$OCH_3$), 3.93 (s, 3H, 12-$OCH_3$), 5.98 (m, 1H, 8'-H), 6.33 (m, 2H, H-benzene ring), 6.51 (m, 2H, H-benzene ring), 6.85 (m, 3H, H-benzene ring), 7.13 (m, 1H, 13'-H), 7.35 (m, 1H, 14'-H).

Compound BS-FC-417 was prepared by reacting compound BS-FC-4 with thiomorpholine according to the process for preparing BS-FC-418 using the same reagents:

LC-MS: retention time: 0.78 min (100%); m/z 768.0 $[M+H]^+$, 384.8 $[½M+H]^+$.

$^1$H NMR (301 MHz, partial assignment of signals in $CDCl_3$) δ 2.31 (s, 3H, N—$CH_3$), 2.64 (m, 3H, N'—$CH_3$), 3.31 (s, 3H, 6'-$OCH_3$), 3.73 (s, 3H, 6-$OCH_3$), 3.91 (s, 3H, 12-$OCH_3$), 5.98 (s, 1H, 8'-H), 6.28 (m, 2H, H-benzene ring), 6.50 (m, 2H, H-benzene ring), 6.83 (m, 3H, H-benzene ring), 7.11 (m, 1H, 13'-H), 7.35 (m, 1H, 14'-H).

Compound BS-FC-419 was prepared by reacting compound BS-FC-4 with 4-hydroxypiperidine according to the process for preparing BS-FC-418 using the same reagents:

LC-MS: retention time: 0.71 min (88.32%); m/z 765.9 $[M+H]^+$, 383.7 $[½M+H]^+$.

$^1$H NMR (301 MHz, partial assignment of signals in $CDCl_3$) δ 2.27 (s, 3H, N—$CH_3$), 2.62 (m, 3H, N'—$CH_3$), 3.33 (s, 3H, 6'-$OCH_3$), 3.71 (s, 3H, 6-$OCH_3$), 3.90 (s, 3H, 12-$OCH_3$), 5.97 (s, 1H, 8'-H), 6.28 (m, 2H, H-benzene ring), 6.50 (m, 2H, H-benzene ring), 6.83 (m, 3H, H-benzene ring), 7.09 (m, 1H, 13'-H), 7.34 (m, 1H, 14'-H).

Compound BS-FC-420 was prepared by reacting compound BS-FC-4 with N-ethylpiperazine according to the process for preparing BS-FC-418 using the same reagents:

LC-MS: retention time: 0.72 min (94.99%); m/z 779.1 $[M+H]^+$, 390.3 $[½M+H]^+$.

$^1$H NMR (301 MHz, partial assignment of signals in $CDCl_3$) δ 2.29 (s, 3H, N—$CH_3$), 2.50 (m, 3H, N'—$CH_3$), 3.35 (s, 3H, 6'-$OCH_3$), 3.73 (s, 3H, 6-$OCH_3$), 3.91 (s, 3H, 12-$OCH_3$), 5.97 (m, 1H, 8'-H), 6.29 (m, 2H, H-benzene ring), 6.50 (m, 2H, H-benzene ring), 6.84 (m, 1H, 10'-H), 6.84 (m, 2H, H-benzene ring), 7.14 (m, 1H, 13'-H), 7.31 (m, 1H, 14'-H).

Compound BS-FC-421 was prepared by reacting compound BS-FC-4 with N-cyanopiperazine according to the process for preparing BS-FC-418 using the same reagents:

LC-MS: retention time: 0.77 min (92.20%); m/z 775.1 $[M+H]^+$, 388.3 $[½M+H]^+$.

$^1$H NMR (301 MHz, partial assignment of signals in $CDCl_3$) δ 2.31 (s, 3H, N—$CH_3$), 2.66 (m, 3H, N'—$CH_3$), 3.34 (s, 3H, 6'-$OCH_3$), 3.71 (s, 3H, 6-$OCH_3$), 3.89 (s, 3H, 12-$OCH_3$), 5.96 (s, 1H, 8'-H), 6.29 (s, 2H, H-benzene ring), 6.50 (m, 2H, H-benzene ring), 6.90 (m, 3H, H-benzene ring), 7.09 (m, 1H, 13'-H), 7.32 (m, 1H, 14'-H).

Compound BS-FC-422 was prepared by reacting compound BS-FC-4 with N-hydroxyethylpiperazine according to the process for preparing BS-FC-418 using the same reagents:

LC-MS: retention time: 0.67 min (92.80%); m/z 794.9 $[M+H]^+$, 398.2 $[½M+H]^+$.

$^1$H NMR (301 MHz, partial assignment of signals in $CDCl_3$) δ 2.28 (s, 3H, N—$CH_3$), 2.66 (m, 3H, N'—$CH_3$), 3.34 (s, 3H, 6'-$OCH_3$), 3.71 (s, 3H, 6-$OCH_3$), 3.89 (s, 3H, 12-$OCH_3$), 5.96 (s, 1H, 8'-H), 6.28 (s, 2H, H-benzene ring), 6.48 (m, 2H, H-benzene ring), 6.82 (m, 3H, H-benzene ring), 7.09 (m, 1H, 13'-H), 7.32 (m, 1H, 14'-H).

Compound BS-FC-424 was prepared by reacting compound BS-FC-4 with 3-methoxypropylamine according to the process for preparing BS-FC-418 using the same reagents:

LC-MS: retention time: 0.74 min (85.62%); m/z 753.9 $[M+H]^+$, 377.7 $[½M+H]^+$.

$^1$H NMR (301 MHz, partial assignment of signals in $CDCl_3$) δ 2.30 (s, 3H, N—$CH_3$), 2.67 (m, 3H, N'—$CH_3$), 3.30 (s, 3H, O—$CH_3$), 3.44 (s, 3H, O—$CH_3$), 3.73 (s, 3H, 6-$OCH_3$), 3.92 (s, 3H, 12-$OCH_3$), 6.00 (d, 1H, J=9.6 Hz, 8'-H), 6.29 (m, 2H, H-benzene ring), 6.50 (s, 1H, H-benzene ring), 6.53 (s, 1H, H-benzene ring), 6.78 (m, 1H, 10'-H), 6.86 (s, 2H, 13, 14-H), 7.19 (dd, 1H, J=2.1, 8.4 Hz, 13'-H), 7.36 (dd, 1H, J=2.1, 8.4 Hz, 14'-H).

Compound BS-FC-425 was prepared by reacting compound BS-FC-4 with furfurylamine according to the process for preparing BS-FC-418 using the same reagents:

LC-MS: retention time: 0.77 min (87.94%); m/z 761.9 $[M+H]^+$, 381.7 $[½M+H]^+$.

Example 6

Evaluation of the 7-Substituted Fangchinoline Derivatives of the Present Invention for their Anti-Leukemia Activities (1) Experimental Materials Leukemia cell lines: leukemia cell lines: K562adr (drug-resistant, chronic myeloid leukemia, CML), NB4 (acute promyelocytic leukemia, AML), Kasumi-1 (acute myeloid leukemia M2 type, AML-M2), Jurkat (acute lymphoblastic leukemia, ALL), all of which were donated by Cancer Research Institute of Zhejiang University, China; and H9 (acute lymphoblastic leukemia, ALL), which was purchased from China Center for Type Culture Collection.

Reagents: The standard sample of fangchinoline (FAN) was purchased from Ci Yuan Biotechnology Co., Ltd., Shaanxi, China; and the 7-substituted fangchinoline derivatives according to the present invention.

phoblastic leukemia) activity of BS-FC-308 increased more than 4-fold and 3-fold respectively over fangchinoline; the anti-NB4 (acute promyelocytic leukemia) activity of BS-FC-104, BS-FC-311 and BS-FC-410 increased by more than 2-fold; additionally, the anti-Kasumi-1 (acute myeloid leukemia M2 type) activity of BS-FC-311 increased by almost 2-fold over fangchinoline.

TABLE 1

Determination of the inhibiting concentrations of the fangchinoline derivatives on leukemia, human multiple myeloma and lymphoma cell growth (72 h, $IC_{50}$ (μg/mL) value and $IC_{90}$ (μg/mL) value).

| | K562/ADR | | Kasumi-1 | | NB4 | | Jurkat | | H9 | |
|---|---|---|---|---|---|---|---|---|---|---|
| Compound | IC50 | IC90 | IC50 | IC90 | IC50 | IC90 | IC50 | IC90 | IC50 | IC90 |
| FAN | 0.36 | 4.13 | 1.11 | 4.11 | 0.58 | 2.59 | 1.73 | 5.25 | 2.40 | 6.60 |
| BS-FC-102 | 0.40 | 3.03 | 1.93 | 4.32 | 0.38 | 0.94 | 0.72 | 1.97 | 2.40 | 6.40 |
| BS-FC-104 | 0.42 | 2.65 | 0.95 | 3.68 | 0.28 | 0.92 | 0.45 | 3.03 | 1.00 | 4.99 |
| BS-FC-204 | 0.38 | 1.92 | 1.29 | 3.16 | 0.39 | 2.57 | 2.23 | 3.86 | 2.20 | 3.70 |
| BS-FC-208 | 0.28 | 2.35 | 0.97 | 4.01 | 0.48 | 2.48 | 0.75 | 1.88 | 2.01 | 4.28 |
| BS-FC-213 | 0.38 | 1.72 | 0.93 | 3.66 | 0.66 | 2.32 | 0.64 | 3.29 | 2.20 | 4.00 |
| BS-FC-216 | 0.60 | 2.15 | 3.22 | 7.22 | 0.99 | 2.93 | 1.42 | 2.91 | 1.80 | 3.30 |
| BS-FC-220 | 0.43 | 4.00 | 1.15 | 3.72 | 0.66 | 3.16 | 0.93 | 3.09 | 3.23 | 6.64 |
| BS-FC-221 | 0.33 | 1.31 | 1.00 | 3.39 | 0.57 | 1.88 | 0.52 | 1.89 | 1.96 | 4.00 |
| BS-FC-304 | 0.44 | 3.00 | 1.54 | 3.94 | 1.24 | 3.99 | 0.81 | 2.94 | 3.60 | 7.05 |
| BS-FC-308 | 0.08 | 0.47 | 0.81 | 1.90 | 0.37 | 0.98 | 0.36 | 1.62 | 0.70 | 1.80 |
| BS-FC-311 | 0.48 | 2.83 | 0.57 | 1.85 | 0.22 | 0.96 | 0.51 | 0.98 | 1.20 | 2.00 |
| BS-FC-315 | 0.26 | 2.14 | 0.85 | 3.04 | 0.33 | 1.32 | 0.59 | 1.24 | 2.00 | 3.77 |
| BS-FC-403 | 0.05 | 0.83 | 0.88 | 2.00 | 0.30 | 0.78 | 0.58 | 0.96 | 0.88 | 1.90 |
| BS-FC-405 | 0.60 | 1.73 | 0.76 | 1.75 | 0.47 | 0.95 | 0.56 | 0.99 | 1.45 | 2.90 |
| BS-FC-409 | 0.16 | 1.38 | 1.46 | 4.82 | 0.59 | 1.76 | 1.02 | 3.33 | 0.90 | 2.00 |
| BS-FC-410 | 0.05 | 0.63 | 0.84 | 1.86 | 0.28 | 0.91 | 0.64 | 1.61 | 1.13 | 2.00 |
| BS-FC-417 | 0.19 | 2.15 | 1.45 | 3.63 | 0.99 | 2.86 | 1.24 | 5.47 | 1.30 | 3.60 |
| BS-FC-421 | 0.21 | 1.43 | 0.95 | 2.55 | 0.61 | 1.61 | 0.97 | 3.79 | 1.00 | 2.80 |

Main apparatuses: an incubator (Model: Thermo Scientific 3111) and a microplate reader (Model: Bio-Rad iMark).

(2) Experimental Method 6000 well-growing leukemia cells were obtained and inoculated into wells of a 96-well cell culture plate. The culture medium was a RPMI-1640 cell culture medium containing 10% fetal bovine serum. After adding the 7-substituted fangchinoline derivatives of different concentrations the next day and mixing uniformly, the plate was placed in a carbon dioxide cell incubator (5% $CO_2$) at 37° C. and incubating for 72 hours. Then the viable cell concentration was determined by the MTT method. In this experiment, the cell viability in control group (not treated with any compound) was set as 100%, and the cell viability (%) after treatment and the half maximal inhibitory concentration of the compound for the leukemia cell growth at 72 hours ($IC_{50}$ value 72 hours, μg/mL) were calculated.

(3) The Experimental Results

The experimental results are shown in Table 1.

Table 1 shows that the 7-substituted fangchinoline derivatives of the present invention can induce the cell death of human chronic myeloid leukemia cells, acute myeloid leukemia cells and acute lymphocytic leukemia cells and inhibit the growth of these leukemia cells. Compared with fangchinoline per se, the 7-substituted fangchinoline derivatives of the present invention exhibit significantly enhanced anti-leukemia cell activities, wherein the anti-K562adr (drug-resistant, chronic myeloid leukemia, CML) activity of the 7-substituted fangchinoline derivatives BS-FC-403 and BS-FC-410 of the present invention is particularly significant and increased by more than 7-fold over fangchinoline; the anti-Jurkat (acute lymphoblastic leukemia) activity and the anti-H9 (acute lym-

Example 7

Evaluation of the 7-Substituted Fangchinoline Derivatives of the Present Invention for their Anti-Human Multiple Myeloma Cell Activities (1) Experimental Materials Myeloma cell lines: RPMI8226 (multiple myeloma), purchased from Fuxiang Bio-tech Co. Ltd., Shanghai, China.

Reagents: the same as in Example 6.

Main apparatuses: a Thermo Scientific 3111 incubator and a Bio-Rad iMark microplate reader.

(2) Experimental Method 6000 well-growing cells were obtained and inoculated into wells of a 96-well cell culture plate. The culture medium was a RPMI-1640 cell culture medium containing 10% fetal bovine serum. After adding the 7-substituted fangchinoline derivatives of different concentrations the next day and mixing uniformly, the plate was placed in a carbon dioxide cell incubator (5% $CO_2$) at 37° C. and incubated for 72 hours. Then the viable cell concentration was determined by the MTT method. In this experiment, the cell viability in control group (not treated with any compound) was set as 100% and the cell viability (%) after treatment and the half maximal inhibitory concentration of the compound for cell growth at 72 hours ($IC_{50}$ value 72 hours, μg/mL) were calculated.

(3) The Experimental Results

The experimental results are shown in table 2.

Table 2 shows that some 7-substituted fangchinoline derivatives of the present invention can induce the death of human myeloma cells and inhibit the growth of these tumor cells, wherein the anti-RPMI8226 (multiple myeloma) activity of the 7-substituted fangchino line derivatives BS-FC-417 of the present invention increased by 2-fold over fangchinoline.

Example 8

Evaluation of the 7-Substituted Fangchinoline Derivatives of the Present Invention for their Anti-Human Solid Tumor Effect (1) Experimental Materials Human Solid Tumor Cell Lines:

Hep-2 (laryngeal carcinoma), A549 (human lung cancer), CaES-17 (esophageal cancer cell), PC-3 (prostate cancer), CNE (nasopharyngeal carcinoma cell) and SK-OV-3 (ovarian cancer cell), all of which were purchased from China Center For Type Culture Collection; RKO (human colon adenocarcinoma cell), MGC-803 (human gastric cancer cell), MG-63 (osteosarcoma), and U87-MG (malignant glioma cell), all of which were purchased from Fuxiang Bio-tech Co. Ltd., Shanghai, China; PANC-1 (pancreatic cancer), Becap37 (human breast cancer cell), Hela (human cervical cancer cell) and Hep G2 (human liver cancer cell), all of which were donated by Cancer Research Institute of Zhejiang University, China.

Reagents: the same as in Example 6.

Main apparatuses: a Thermo Scientific 3111 incubator and a Bio-Rad iMark microplate reader.

(2) Experimental Method 6000 well-growing human solid tumor cells were obtained and inoculated into wells of a 96-well cell culture plate. The culture medium was DMEM High Glucose cell culture medium containing 10% fetal bovine serum. The plate was placed in a carbon dioxide cell incubator (5% $CO_2$) at 37° C. and incubated for 24 hours. After added with 7-substituted fangchinoline derivatives of different concentration and mixing uniformly, the plate was placed in a carbon dioxide cell incubator (5% $CO_2$) at 37° C. and incubated for 72 hours. Then the viable cell concentration was determined by the MTT method. In this experiment, the cell viability of control group (not treated with any compound) was set as 100% and the cell viability (%) after treatment and the half maximal inhibitory concentration of the compound for the leukemia cell growth at 72 hours ($IC_{50}$ value 72 hours) were calculated.

(3) The Experimental Results

The experimental results are shown in Table 2.

Table 2 shows that the 7-substituted fangchinoline derivatives of the present invention can induce the death of human solid tumor cells and inhibit the growth of these tumor cells. As compared with fangchinoline per se, the 7-substituted fangchinoline derivatives of the present invention exhibit remarkably enhanced anti-human solid tumor cell activity, wherein the 7-substituted fangchinoline derivatives of the present invention BS-FC-403, BS-FC-405 and BS-FC-410 exhibit particularly significant enhancement: their anti-PANC-1 (pancreatic cancer), anti-Becap37 (human breast cancer cell) and anti-Hep G2 (human liver cancer cell) activities increased by almost 3-fold or more than 3-fold over fangchinoline per se and their anti-U87-MG (malignant glioma cell) activity increases by more than 1.5-fold; the anti-PC-3 (prostate cancer), anti-SK-OV-3 (ovarian cancer cell) and RKO (human colon adenocarcinoma cell) activities of BS-FC-403 increased by almost 3-fold or more than 3-fold over fangchinoline per se; the anti-A549 (human lung cancer) activity of BS-FC-308 increased by more than 3-fold; the anti-MG-63 (osteosarcoma) activity of BS-FC-221 and BS-FC-403 increased by more than 2-fold; the anti-Hela (human cervical cancer cell) activity of BS-FC-311 and the anti-CaEs-17 (esophageal cancer cell) activity of BS-FC-403 and BS-FC-405 both increased by almost 4-fold; the anti-CNE (nasopharyngeal carcinoma cell) activity of BS-FC-403, BS-FC-405 and BS-FC-421 increased by almost 3-fold; the anti-Hep-2 (laryngeal carcinoma) activity of BS-FC-311, BS-FC-403, BS-FC-405 and BS-FC-409 increased by more than 2-fold; additionally, the anti-MGC-803 (human gastric cancer cell) activity of BS-FC-403 and BS-FC-410 also increased by more than 2-fold over fangchinoline per se.

TABLE 2

Determination of the inhibitory concentrations of the fangchinoline derivatives on human solid tumor cell growth (72 h, $IC_{50}$ (μg/mL) value and $IC_{90}$ (μg/mL) value).

| | RPMI 8226 | | A549 | | PANC-1 | |
|---|---|---|---|---|---|---|
| Compound | IC50 | IC90 | IC50 | IC90 | IC50 | IC90 |
| FAN | 0.04 | 0.50 | 3.26 | 9.81 | 3.14 | 11.64 |
| BS-FC-102 | 0.14 | 0.77 | 2.41 | 6.55 | 3.16 | 6.75 |
| BS-FC-104 | 0.12 | 0.50 | 1.57 | 3.94 | 2.01 | 10.79 |
| BS-FC-204 | 0.42 | 1.58 | 2.16 | 3.94 | 2.23 | 6.85 |
| BS-FC-208 | 0.13 | 0.50 | 2.51 | 13.05 | 2.87 | 8.31 |
| BS-FC-213 | 0.12 | 0.50 | 2.19 | 4.92 | 3.46 | 10.36 |
| BS-FC-216 | 0.13 | 0.77 | 2.70 | 5.90 | 3.62 | 7.25 |
| BS-FC-220 | 0.12 | 0.50 | 2.55 | 4.97 | 2.79 | 7.68 |
| BS-FC-221 | 0.11 | 0.46 | 1.20 | 3.18 | 1.42 | 4.65 |
| BS-FC-304 | 0.16 | 0.98 | 2.24 | 5.59 | 3.73 | 10.39 |
| BS-FC-308 | 0.12 | 0.25 | 0.99 | 3.16 | 2.38 | 8.53 |
| BS-FC-311 | 0.13 | 0.49 | 1.36 | 4.38 | 2.95 | 4.80 |
| BS-FC-315 | 0.13 | 0.48 | 1.85 | 3.48 | 1.61 | 5.52 |
| BS-FC-403 | <0.125 | 0.13 | 1.84 | 6.34 | 1.03 | 3.17 |
| BS-FC-405 | 0.05 | 0.44 | 1.94 | 5.89 | 1.14 | 3.34 |
| BS-FC-409 | 0.04 | 0.50 | 2.98 | 8.43 | 3.17 | 7.14 |
| BS-FC-410 | <0.125 | 0.25 | 1.71 | 6.80 | 1.11 | 3.77 |
| BS-FC-417 | 0.02 | 0.50 | 3.77 | 11.70 | 5.55 | 9.00 |
| BS-FC-421 | <0.125 | 0.25 | 3.78 | 10.16 | 2.96 | 7.01 |

TABLE 2-continued

Determination of the inhibitory concentrations of the fangchinoline derivatives on human solid tumor cell growth (72 h, $IC_{50}$ (μg/mL) value and $IC_{90}$ (μg/mL) value).

| Compound | Becap-37 IC50 | Becap-37 IC90 | MG-63 IC50 | MG-63 IC90 | Hep G2 IC50 | Hep G2 IC90 | RKO IC50 | RKO IC90 |
|---|---|---|---|---|---|---|---|---|
| FAN | 1.79 | 6.2 | 1.7 | 3.7 | 1.81 | 5.23 | 0.92 | 3.11 |
| BS-FC-102 | 2.49 | 4 | 3.18 | 4.83 | 1.56 | 3.94 | 1.44 | 2.33 |
| BS-FC-104 | 1.92 | 3.94 | 2.71 | 3.88 | 1.44 | 3.9 | 0.74 | 1.76 |
| BS-FC-204 | 4.87 | 7.89 | 2.6 | 3.5 | 3.73 | 7.96 | 1.66 | 2.95 |
| BS-FC-208 | 2.35 | 5.55 | 1.6 | 2.5 | 1.94 | 5.95 | 1.64 | 4.64 |
| BS-FC-213 | 2.54 | 5.29 | 2.4 | 3.8 | 2.12 | 5.92 | 1.58 | 3.46 |
| BS-FC-216 | 3.36 | 5.3 | 3.4 | 5.5 | 2.54 | 5.91 | 1.69 | 5.79 |
| BS-FC-220 | 3.19 | 6.1 | 2.8 | 3.6 | 2.37 | 7.01 | 1.25 | 3.73 |
| BS-FC-221 | 1.91 | 3.86 | 0.8 | 1.9 | 1.48 | 4.37 | 1.37 | 2.76 |
| BS-FC-304 | 3.15 | 7.22 | 2.32 | 5.72 | 2.49 | 9.42 | 1.79 | 3.45 |
| BS-FC-308 | 1.03 | 1.95 | 1.3 | 1.8 | 1.12 | 4.35 | 0.71 | 1.51 |
| BS-FC-311 | 1.53 | 3.03 | 2 | 4.37 | 1.4 | 2.76 | 1.32 | 3.24 |
| BS-FC-315 | 2.1 | 3.79 | 2.4 | 3.9 | 1.39 | 3.74 | 1.15 | 2.23 |
| BS-FC-403 | 0.59 | 2.09 | 0.6 | 1.3 | 0.55 | 2.23 | 0.34 | 0.79 |
| BS-FC-405 | 0.74 | 1.88 | 0.96 | 1.7 | 0.71 | 1.7 | 0.46 | 0.92 |
| BS-FC-409 | 1.44 | 4.8 | 1.1 | 1.99 | 1.27 | 3.24 | 0.65 | 1.27 |
| BS-FC-410 | 0.73 | 2.48 | 1.1 | 1.7 | 0.66 | 1.51 | 0.44 | 0.95 |
| BS-FC-417 | 2.42 | 6.16 | 2 | 3.6 | 1.8 | 5.79 | 1.09 | 2.27 |
| BS-FC-421 | 1.15 | 3.96 | 1.6 | 2.4 | 1.16 | 3.25 | 0.61 | 2.33 |

| Compound | U87-MG IC50 | U87-MG IC90 | Hela IC50 | Hela IC90 | CaEs-17 IC50 | CaEs-17 IC90 | CNE IC50 | CNE IC90 |
|---|---|---|---|---|---|---|---|---|
| FAN | 1.12 | 3.79 | 1.96 | 6.12 | 1.94 | 8.98 | 2.40 | 5.70 |
| BS-FC-102 | 1.79 | 5.39 | 1.44 | 3.39 | 2.47 | 7.91 | 3.50 | 6.90 |
| BS-FC-104 | 1.63 | 4.50 | 1.00 | 3.42 | 2.00 | 7.42 | 2.50 | 4.90 |
| BS-FC-204 | 2.38 | 9.10 | 0.50 | 1.00 | 4.60 | 14.52 | 2.70 | 5.20 |
| BS-FC-208 | 1.99 | 7.48 | 1.74 | 4.00 | 1.79 | 6.87 | 2.70 | 6.00 |
| BS-FC-213 | 1.85 | 9.23 | 1.68 | 3.89 | 1.68 | 9.16 | 2.70 | 5.60 |
| BS-FC-216 | 2.11 | 7.74 | 1.58 | 3.84 | 3.10 | 7.59 | 3.38 | 7.34 |
| BS-FC-220 | 2.28 | 7.03 | 1.43 | 3.71 | 2.60 | 9.32 | 3.20 | 7.60 |
| BS-FC-221 | 1.13 | 4.50 | 0.71 | 1.90 | 1.53 | 5.60 | 1.80 | 3.80 |
| BS-FC-304 | 1.68 | 4.97 | 1.87 | 4.65 | 2.35 | 10.72 | 3.80 | 7.20 |
| BS-FC-308 | 1.27 | 3.75 | 0.89 | 1.90 | 0.93 | 3.92 | 1.90 | 3.60 |
| BS-FC-311 | 1.25 | 3.80 | 0.50 | 2.89 | 1.95 | 7.37 | 1.83 | 5.04 |
| BS-FC-315 | 1.34 | 3.24 | 1.50 | 3.35 | 1.84 | 3.86 | 3.30 | 6.60 |
| BS-FC-403 | 0.71 | 1.73 | 0.90 | 2.96 | 0.43 | 1.99 | 0.87 | 2.20 |
| BS-FC-405 | 0.70 | 1.41 | 1.25 | 2.00 | 0.49 | 1.95 | 0.80 | 1.70 |
| BS-FC-409 | 1.07 | 2.68 | 1.05 | 3.52 | 0.91 | 4.90 | 0.95 | 3.94 |
| BS-FC-410 | 0.67 | 1.19 | 1.33 | 2.41 | 0.76 | 4.30 | 1.10 | 2.40 |
| BS-FC-417 | 1.49 | 4.25 | 1.73 | 4.47 | 1.82 | 7.67 | 1.66 | 5.24 |
| BS-FC-421 | 1.05 | 2.75 | 0.88 | 2.78 | 0.88 | 9.43 | 0.87 | 3.87 |

| Compound | Hep-2 IC50 | Hep-2 IC90 | MGC-803 IC50 | MGC-803 IC90 | PC-3 IC50 | PC-3 IC90 | SK-OV-3 IC50 | SK-OV-3 IC90 |
|---|---|---|---|---|---|---|---|---|
| FAN | 3.60 | 10.04 | 1.08 | 6.42 | 4.08 | 7.64 | 3.61 | 14.49 |
| BS-FC-102 | 3.99 | 11.05 | 1.71 | 4.95 | 3.17 | 5.85 | 1.92 | 8.07 |
| BS-FC-104 | 3.18 | 10.22 | 1.36 | 4.28 | 2.50 | 5.51 | 1.88 | 3.79 |
| BS-FC-204 | 3.18 | 8.31 | 2.94 | 8.50 | 3.80 | 6.39 | 12.23 | 16.00 |
| BS-FC-208 | 3.27 | 8.05 | 1.49 | 5.98 | 3.07 | 5.91 | 3.77 | 7.85 |
| BS-FC-213 | 3.63 | 9.90 | 1.49 | 6.02 | 3.24 | 7.37 | 5.00 | 11.78 |
| BS-FC-216 | 3.69 | 7.88 | 2.72 | 3.98 | 3.95 | 7.45 | 6.19 | 11.23 |
| BS-FC-220 | 4.20 | 10.27 | 1.40 | 3.96 | 4.55 | 7.61 | 5.41 | 14.25 |
| BS-FC-221 | 1.90 | 5.78 | 1.19 | 3.93 | 3.00 | 5.46 | 2.38 | 3.94 |
| BS-FC-304 | 4.95 | 12.24 | 1.87 | 10.25 | 4.02 | 10.50 | 6.45 | 15.38 |
| BS-FC-308 | 3.08 | 6.05 | 0.57 | 1.99 | 2.40 | 3.49 | 1.31 | 1.93 |
| BS-FC-311 | 1.64 | 4.85 | 1.40 | 4.79 | 3.08 | 8.39 | 2.87 | 3.96 |
| BS-FC-315 | 3.66 | 6.40 | 1.21 | 3.02 | 2.95 | 5.02 | 2.99 | 6.81 |
| BS-FC-403 | 1.76 | 5.66 | 0.40 | 4.14 | 1.49 | 3.96 | 1.03 | 3.85 |
| BS-FC-405 | 1.67 | 4.81 | 0.88 | 3.59 | 2.53 | 3.69 | 1.54 | 3.50 |
| BS-FC-409 | 1.79 | 5.54 | 0.94 | 16.00 | 2.89 | 5.80 | 2.82 | 9.85 |
| BS-FC-410 | 2.25 | 8.00 | 0.49 | 3.21 | 2.85 | 3.89 | 1.39 | 5.59 |
| BS-FC-417 | 2.36 | 6.03 | 1.49 | 12.89 | 3.68 | 9.36 | 4.60 | 12.91 |
| BS-FC-421 | 1.92 | 8.95 | 0.84 | 4.44 | 2.72 | 6.07 | 2.36 | 11.01 |

Example 9

Evaluation of the In Vivo Anti-Tumor Activity of the 7-Substituted Fangchinoline Derivative of the Present Invention BS-FC-308 and Preliminary Evaluation of its Toxicity Experiment 9-1

The Inhibiting Effect of BS-FC-308 on the Transplanted Tumor of Liver Cancer in Nude Mice (1) Experimental Materials Liver cancer cell lines: Hep G2 (human liver cancer cell line);

Animal: BALBc nude mice (immunodeficient mice), 8 weeks, female, purchased from Shanghai Laboratory Animal Center of Chinese Academy of Sciences, China.

(2) Reagents:

BS-FC-308 (synthesized from experiments);

Erlotinib hydrochloride (Shandong Zibo Kai-Mei-Yuan Pharmaceutical Co. Ltd.)

(3) Main Apparatuses:

A cell incubator (Thermo Scientific, 3111);

A laminar flow rack (Suhang Experimental Animal Equipment Factory, DJ-2).

(4) Experimental Method

Under sterile conditions, the Hep G2 cells in the logarithmic growth phase were respectively collected and injected subcutaneously in an amount of $2.3\times10^7$/0.2 mL/nude mice (cell viability >90%) into the left subaxillary of the nude mice, thus establishing a transplanted tumor model of liver cancer in nude mice. The mice were administered from the second day after inoculation. The experimental group was intragastrically administered with the experimentally designed amount, the negative control group was intragastrically administered with sterile water, and the positive control group was intragastrically administered with erlotinib hydrochloride. Each mouse was intragastrically administered in 0.4 ml each time and 3 times a day, at 8:00, 14:00 and 20:00, with 6-hour intervals. The administrations were successive for 10 days. The day before administration was deemed as Day 0 and the weight and tumor size of the mice were determined every 5 days to produce a dynamic plot on weight and tumor growth (the experimental results are presented as mean±SD). On Day 28, the mice were sacrificed and the tumors were taken out and weighed. The tumor inhibition rate (%) after the effect of the medicament was calculated based on a tumor inhibition rate of the control group being zero.

The experimental data for each group were analyzed by using the One-way ANOVA method in the SPSS 19.0 statistical software and were compared with the control group for significance of difference.

TABLE 3

The effect of BS-FC-308 on the weight of the nude mice

| Group | Dosage (mg/kg/time) | Number of animals Initial | Number of animals Final | Body Weight (g) Initial | Body Weight (g) Final |
|---|---|---|---|---|---|
| Sterile water | — | 3 | 3 | 22.4 ± 0.21 | 21.4 ± 0.91 |
| Erlotinib hydrochloride | 20 | 3 | 3 | 21.4 ± 0.26 | 20.4 ± 1.72 |
| BS-FC-308 | 35 | 3 | 3 | 21.8 ± 0.62 | 19.0 ± 0.49 |

TABLE 4

The effect of BS-FC-308 on the Hep G2 transplanted tumor in the nude mice

| Group | Dosage (mg/kg/time) | Mass of tumor (mg) | Tumor Inhibition rate (%) |
|---|---|---|---|
| Sterile water | — | 1281 ± 353.53 | — |
| Erlotinib hydrochloride | 20 | 839 ± 270.62 | 34.5 |
| BS-FC-308 | 35 | 566 ± 112.26* | 55.82 |

Note:
as compared with the control group, *means $P < 0.05$.

FIG. 1 shows the curve displaying the dynamic effect of BS-FC-308 on the body weight of nude mice.

Figure 2:
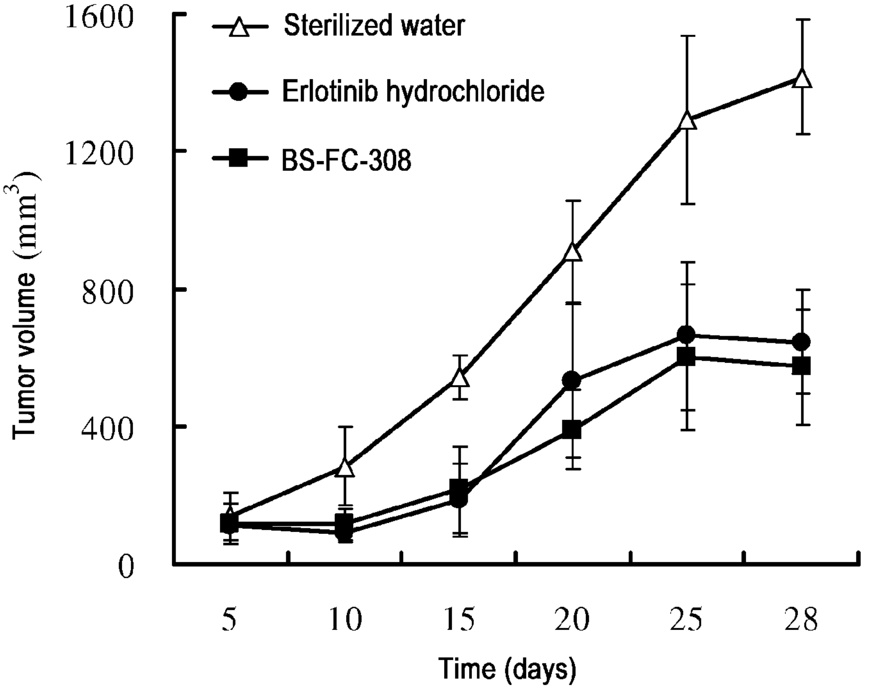
FIG. 2 is a curve showing the dynamic effect of BS-FC-308 on the volume of Hep G2 transplanted tumors in nude mice.

FIG. 2 shows the curve displaying the dynamic effect of BS-FC-308 on the volume of the Hep G2 transplanted tumors in nude mice.

Figure 3:
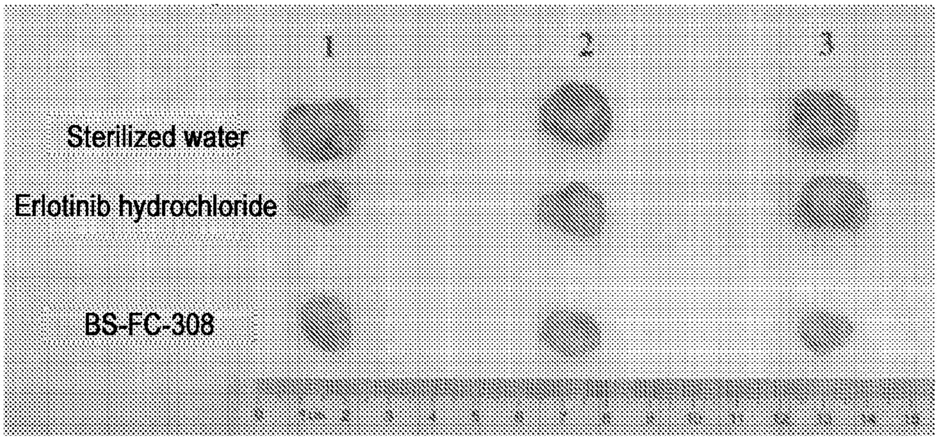
FIG. 3 shows the effect of BS-FC-308 on the size of Hep G2 transplanted tumors in nude mice.

FIG. 3 shows that BS-FC-308 significantly reduces the weight of the Hep G2 transplanted tumors in nude mice.

Figure 4:
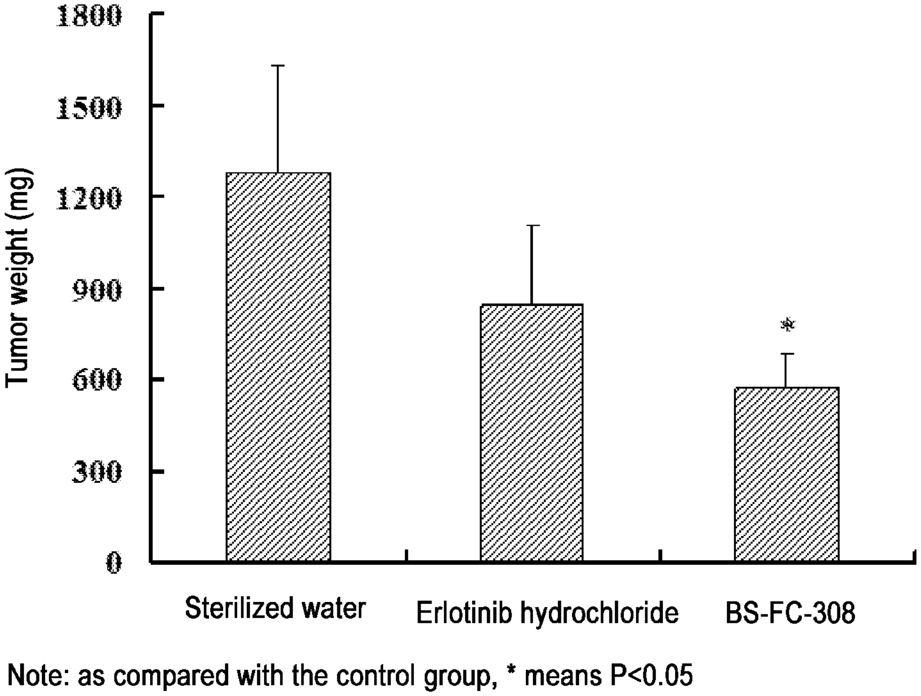
FIG. 4 shows the effect of BS-FC-308 on the weight of Hep G2 transplanted tumors in nude mice.

FIG. 4 shows the effect of BS-FC-308 on the weight of the Hep G2 transplanted tumors in nude mice.

Figure 5:
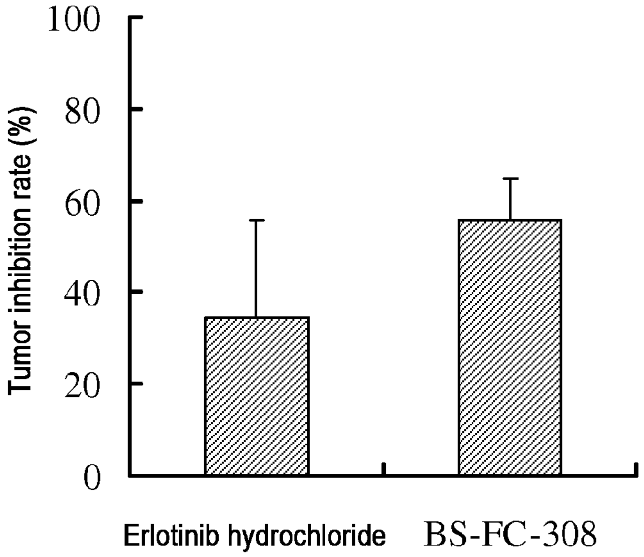
FIG. 5 shows the inhibiting effect of BS-FC-308 on Hep G2 transplanted tumors in nude mice.

FIG. 5 shows the inhibiting effect of BS-FC-308 on the Hep G2 transplanted tumors in nude mice As is shown in the above tables and figures, in the in vivo animal experiments, at the dosage of 35 mg/kg/time and three administrations per day, BS-FC-308 can effectively inhibit the growth of the Hep G2 transplanted tumor of the liver cancer cell with an inhibition rate of 55.82%. During the administration, the animal's body weight was reduced, which indicates certain toxic and side effects on the animal by the compound. After the administration stops, however, the animal's weight rebounded.

Experiment 9-2

The Effect of BS-FC-308 on the Transplanted Tumor of Leukemia in Nude Mice (1) Experimental Materials Leukemia cell lines: KCL-22M (human chronic myeloid leukemia mutant strain);

Animal: BALBc nude mice (immunodeficient mice), 8 weeks, female, purchased from Shanghai Laboratory Animal Center of Chinese Academy of Sciences, China.

(2) Reagents:

BS-FC-308 (synthesized from experiments).

(3) Main Apparatuses:

A cell incubator (Thermo Scientific, 3111);

A laminar flow rack (Suhang Experimental Animal Equipment Factory, DJ-2).

(4) Experimental Method

Under sterile conditions, the KCL-22M cells in the logarithmic growth phase were respectively collected and injected subcutaneously in an amount of $1\times10^7$/0.2 mL/nude mice (cell viability >90%) into the left subaxillary of the nude mice, thus establishing a transplanted tumor model of leukemia in nude mice. The mice were administered from the second day after the inoculation. The experimental group was intragastrically administered with the experimentally designed amount while the negative control group is intragastrically administered with sterile water. Each mouse was intragastrically administered in 0.4 ml each time and 3 times a day, at 8:00, 14:00 and 20:00. The administrations were successive for 10 days. The day before administration was deemed as Day 0 and the weight and tumor size of the mice were determined every 5 days to produce a dynamic plot on weight and tumor growth (the experimental results are presented as mean±SD). On Day 25, the mice were sacrificed and the tumors are taken out and weighed. The tumor inhibition rate (%) was calculated after the effect of the medicament based on a tumor inhibition rate of the control group being zero.

The experimental data for each group were analyzed by using the One-way ANOVA method in the SPSS 19.0 statistical software and were compared with the control group for significance of difference.

TABLE 5

The effect of BS-FC-308 on the body weight of the nude mice

| Groups | Dosage (mg/kg/time) | Number of animals Initial | Final | Body Weight (g) Initial | Final |
|---|---|---|---|---|---|
| Sterile water | — | 3 | 3 | 20.2 ± 0.2 | 18.9 ± 2.07 |
| BS-FC-308 | 30 | 3 | 3 | 19.5 ± 0.2 | 15.4 ± 1.51 |

TABLE 6

The effect of BS-FC-308 on the KCL-22M transplanted tumor in the nude mice

| Group | Dosage (mg/kg/time) | Mass of tumor (g) | Tumor Inhibition rate (%) |
|---|---|---|---|
| Control | — | 2037.7 ± 964.58 | — |
| BS-FC-308 | 30 | 520.7 ± 248.54* | 74.45 |

Note:
as compared with the control group, *means $P < 0.05$.

Figure 6:
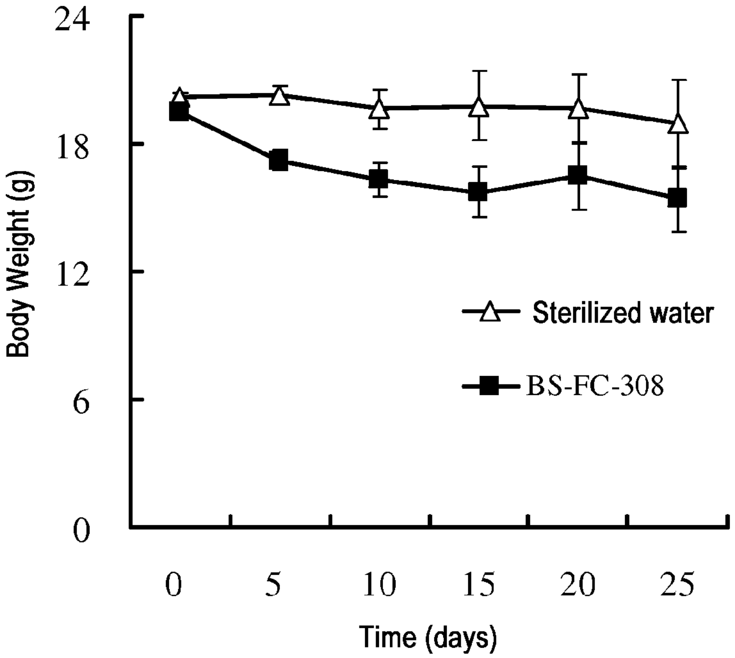
FIG. 6 is a curve showing the dynamic effect of BS-FC-308 on the body weight of nude mice.

FIG. 6 shows the curve displaying the dynamic effect of BS-FC-308 on the body weight of nude mice.

Figure 7:
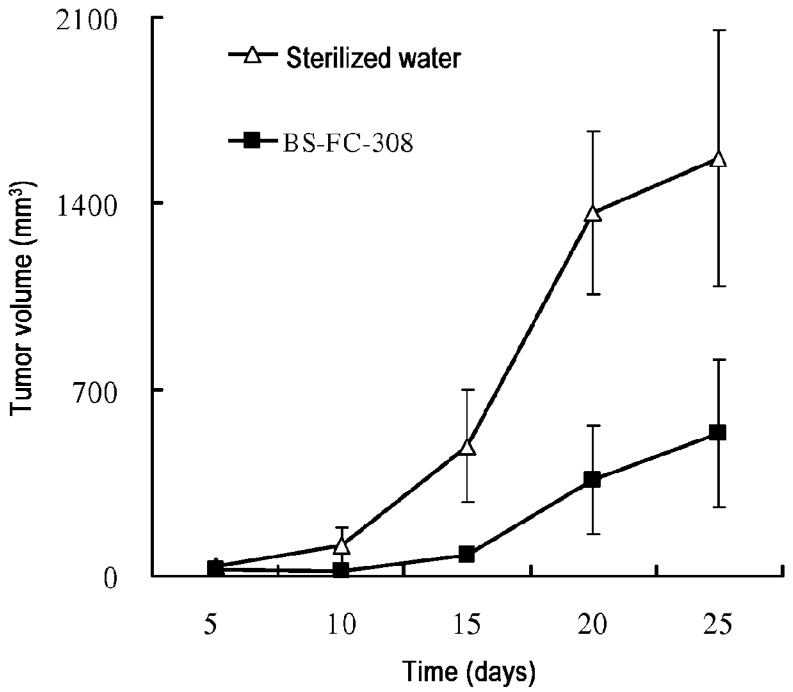
FIG. 7 is a curve showing the dynamic effect of BS-FC-308 on the volume of to KCL-22M transplanted tumors in nude mice.

FIG. 7 shows the curve displaying the dynamic effect of BS-FC-308 on the volume of the KCL-22M transplanted tumors in nude mice.

Figure 8:
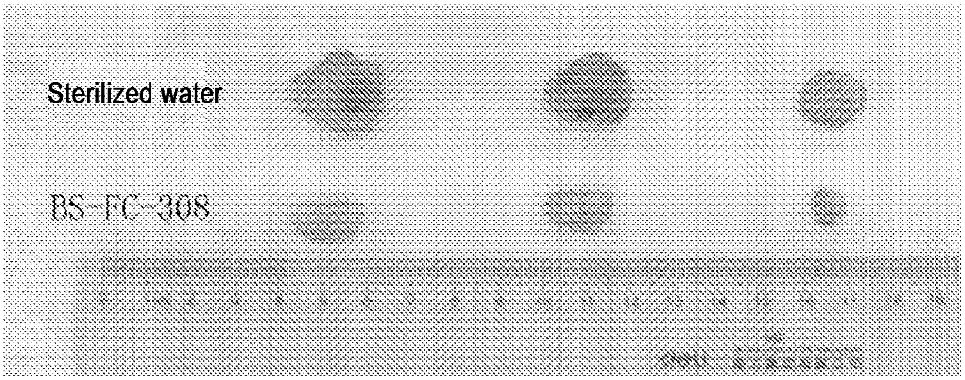
FIG. 8 shows the effect of BS-FC-308 on the size of KCL-22M transplanted tumors in nude mice.

FIG. 8 shows the effect of BS-FC-308 on the size of the KCL-22M transplanted tumors in nude mice.

Figure 9:
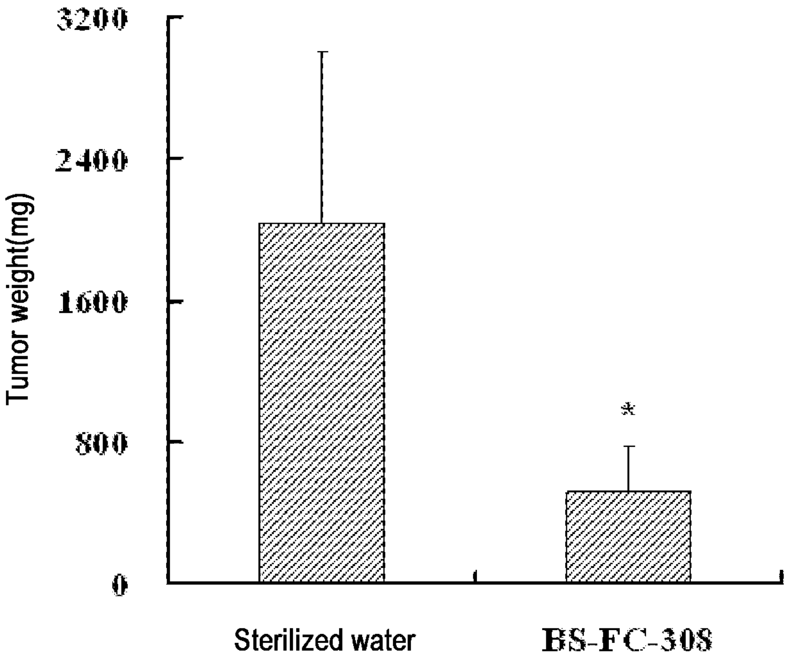
FIG. 9 shows the effect of BS-FC-308 on the weight of KCL-22M transplanted tumors in nude mice.

FIG. 9 shows the effect of BS-FC-308 on the weight of the KCL-22M transplanted tumors in nude mice.

Figure 10:
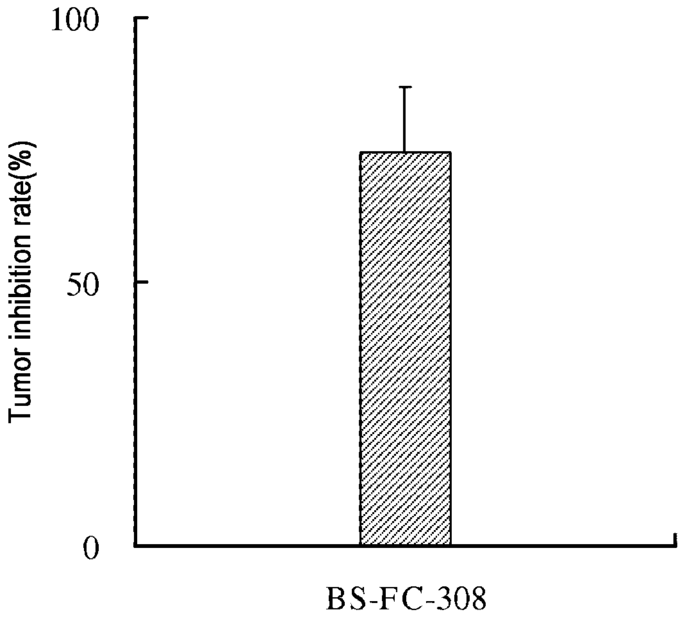
FIG. 10 shows the inhibiting effect of BS-FC-308 on the KCL-22M transplanted tumors in nude mice.

FIG. 10 shows the inhibiting effect of BS-FC-308 on the KCL-22M transplanted tumors in nude mice.

As is shown in the above tables and figures, in the in vivo experiments, the present experiment verified that, at the dosage of 30 mg/kg/time and three administrations per day, BS-FC-308 can effectively inhibit the growth of the KCL-22M transplanted tumor of leukemia cell with an inhibition rate of 74.45%. During the administration, the animal's weight was reduced, which indicates certain toxic and side effects on the animal by the compound. After the administration was stopped, however, the animal's weight rebounded.

The invention claimed is:

1. A compound of formula (I), or a pharmaceutically acceptable salt thereof,

I

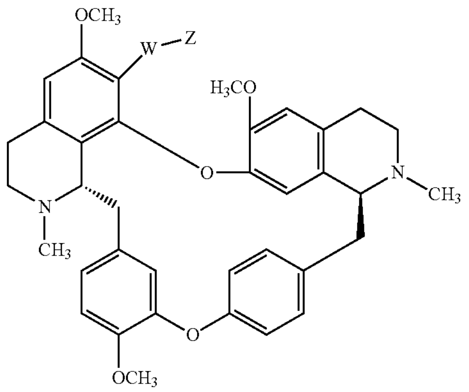

wherein

W is —$OSO_2$— or —OC(O)—;

Z is selected from the group consisting of H, $C_1$-$C_6$ alkyl substituted with a substituent, $C_2$-$C_6$ alkenyl optionally substituted with a substituent, $C_3$-$C_7$ cycloalkyl or cycloalkenyl optionally substituted with a substituent, heterocyclyl optionally substituted with a substituent, aryl or heteroaryl optionally substituted with a substituent, and $R_2R_3NCH_2CH(OH)$—;

$R_2$ and $R_3$ are independently H, $C_1$-$C_6$ alkyl or $C_2$-$C_6$ alkenyl optionally substituted with hydroxyl, $C_1$-$C_6$ alkoxy, halogen, $C_3$-$C_7$ cycloalkyl or cycloalkenyl, aryl or heteroaryl, or $R_2$ and $R_3$, together with the nitrogen atom to which they are attached, form 3-7 membered nitrogen-containing heterocycle; said nitrogen-containing heterocycle optionally comprises an additional heteroatom selected from oxygen, sulfur and nitrogen and is optionally substituted with a substituent;

wherein said substituent is selected from the group consisting of halogen, amino, $C_1$-$C_6$ alkyl amino, di($C_1$-$C_6$alkyl)amino, nitro, cyano, hydroxyl, $C_1$-$C_6$alkoxy, $C_1$-$C_6$ haloalkoxy, mercapto and $C_1$-$C_6$ alkylthio; for said aryl, heteroaryl, $C_3$-$C_7$ cycloalkyl or cycloalkenyl, heterocyclyl and nitrogen-containing heterocyclyl, said substituent is also selected from the group consisting of $C_1$-$C_6$ alkyl, hydroxyl $C_1$-$C_6$ alkyl and $C_1$-$C_6$ haloalkyl;

wherein said heteroaryl refers to an aromatic ring group having 1-4 heteroatoms in the ring as ring atom(s), the heteroatom is selected from the group consisting of nitrogen, oxygen and sulfur, and the heteroaryl is a monocyclic heteroaryl having 5-7 ring atoms or a bicyclic heteroaryl having 7-11 ring atoms;

wherein said heterocyclyl refers to a non-aromatic cyclic group containing 1-4 heteroatoms as ring members, the heteroatom refers to nitrogen, oxygen or sulfur, and the heterocyclyl is a monocyclic heterocyclyl having 4-8 ring atoms or a bicyclic heterocyclyl having 7-11 ring atoms;

and wherein when W is —OC(O)—, Z is not methyl, ethyl or propyl.

2. The compound or a pharmaceutically acceptable salt thereof according to claim 1, wherein W is —$OSO_2$—;

Z is selected from the group consisting of H, $C_1$-$C_6$ alkyl substituted with a substituent, $C_2$-$C_6$ alkenyl optionally substituted with a substituent, $C_3$-$C_7$ cycloalkyl or cycloalkenyl optionally substituted with a substituent, a heterocyclyl optionally substituted with a substituent, and aryl or a heteroaryl optionally substituted with a substituent;

wherein said substituent is selected from the group consisting of halogen, amino, $C_1$-$C_6$ alkyl amino, di($C_1$-$C_6$ alkyl)amino, nitro, cyano, hydroxyl, $C_1$-$C_6$alkoxy, $C_1$-$C_6$ haloalkoxy, mercapto and $C_1$-$C_6$ alkylthio; for said aryl, heteroaryl, $C_3$-$C_7$ cycloalkyl or cycloalkenyl, and heterocyclyl, said substituent is also selected from the group consisting of $C_1$-$C_6$ alkyl, hydroxyl $C_1$-$C_6$ alkyl and $C_1$-$C_6$ haloalkyl.

3. The compound or a pharmaceutically acceptable salt thereof according to claim 2, wherein Z is selected from the group consisting of $C_1$-$C_6$ alkyl substituted with a substituent, and aryl or heteroaryl optionally substituted with a substituent;

wherein said substituent is selected from the group consisting of halogen, amino, $C_1$-$C_6$ alkyl amino, di($C_1$-$C_6$ alkyl)amino, nitro, cyano, hydroxyl, $C_1$-$C_6$ alkoxy, $C_1$-$C_6$ haloalkoxy, mercapto and $C_1$-$C_6$ alkylthio; for said aryl and heteroaryl, said substituent is also selected from the group consisting of $C_1$-$C_6$ alkyl, hydroxyl $C_1$-$C_6$ alkyl and $C_1$-$C_6$ haloalkyl.

4. The compound or a pharmaceutically acceptable salt thereof according to claim 3, wherein Z is selected from the group consisting of $C_1$-$C_6$ alkyl substituted with a substituent, and phenyl optionally substituted with a substituent;

wherein said substituent is selected from the group consisting of halogen, $C_1$-$C_6$ alkoxy and $C_1$-$C_6$ haloalkoxy; said phenyl can also be substituted with a substituent selected from the group consisting of $C_1$-$C_6$ alkyl, hydroxyl $C_1$-$C_6$ alkyl and $C_1$-$C_6$ haloalkyl.

5. The compound or a pharmaceutically acceptable salt thereof according to claim 1, wherein Z is phenyl optionally substituted with $C_1$-$C_6$ alkyl.

6. The compound or a pharmaceutically acceptable salt thereof according to claim 1, wherein W is —OC(O)—;

Z is selected from the group consisting of $C_1$-$C_6$ alkyl substituted with a substituent, $C_2$-$C_6$ alkenyl optionally substituted with a substituent, $C_3$-$C_7$ cycloalkyl or cycloalkenyl optionally substituted with a substituent, heterocyclyl optionally substituted with a substituent, and aryl or heteroaryl optionally substituted with a substituent;

wherein said substituent is selected from the group consisting of halogen, amino, $C_1$-$C_6$ alkyl amino, di($C_1$-$C_6$alkyl)amino, nitro, cyano, hydroxyl, $C_1$-$C_6$alkoxy, $C_1$-$C_6$ haloalkoxy, mercapto and $C_1$-$C_6$ alkylthio; for said aryl, heteroaryl, $C_3$-$C_7$ cycloalkyl, cycloalkenyl and heterocyclyl, said substituent is also selected from the group consisting of $C_1$-$C_6$ alkyl, hydroxyl $C_1$-$C_6$ alkyl and $C_1$-$C_6$ haloalkyl.

7. The compound or a pharmaceutically acceptable salt thereof according to claim 1, wherein Z is phenyl, pyridyl, or pyridazinyl, each of which is optionally substituted with a substituent selected from methyl, ethyl, isopropyl, amino, methylamino, dimethylamino, diethylamino, methoxyl, trifluoromethoxy and halogen.

8. The compound or a pharmaceutically acceptable salt thereof according to claim 1, selected from the group consisting of the following compounds:

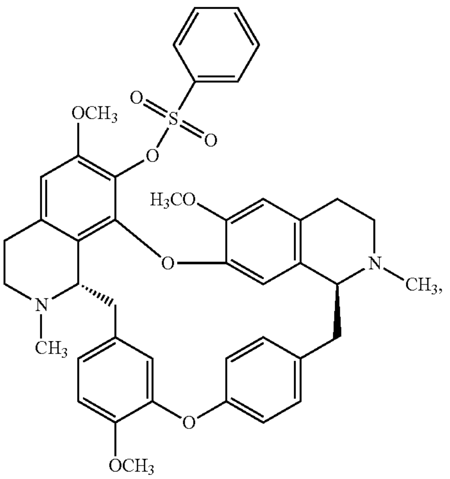

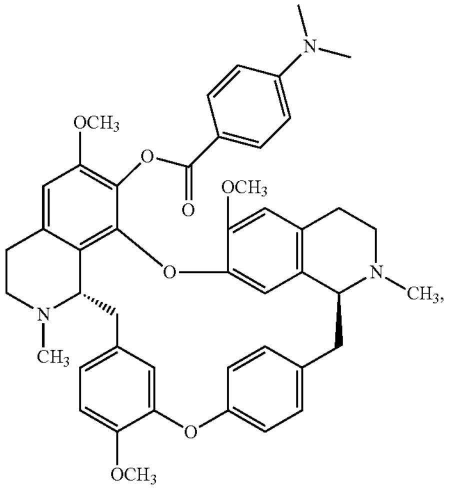

and

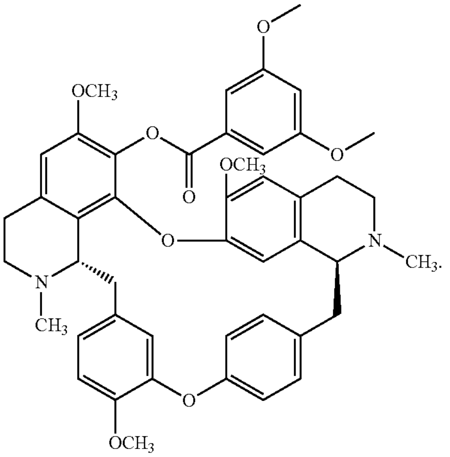

9. A process for preparing a compound of formula (I) according to claim 1, wherein the compound of formula (I-1), (I-1)

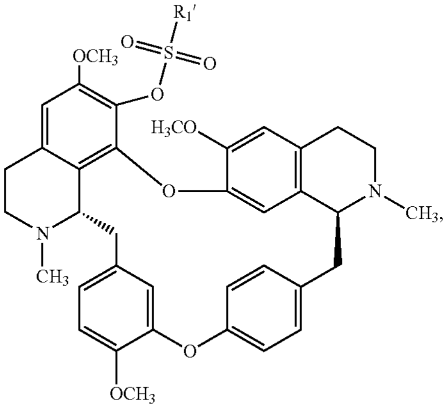

is produced by reacting fangchinoline (FAN), (FAN)

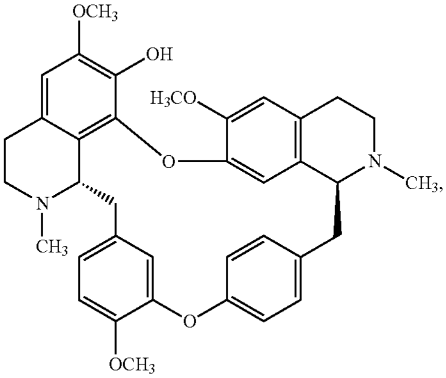

with a corresponding alkyl or aromatic sulfonyl chloride ($R_1$'$SO_2Cl$) in the presence of an alkali at room temperature, wherein $R_1$' is selected from the group consisting of H, $C_1$-$C_6$ alkyl substituted with a substituent, $C_2$-$C_6$ alkenyl optionally substituted with a substituent, $C_3$-$C_7$ cycloalkyl or cycloalkenyl optionally substituted with a substituent, heterocyclyl optionally substituted with a substituent, and aryl or heteroaryl optionally substituted with a substituent, in which said substituent is as defined according to claim 1; or wherein the compound of formula (I-2), (I-2)

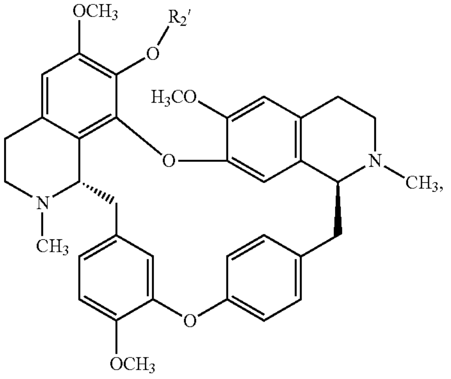

is produced by reacting fangchinoline (FAN) firstly with a strong alkali and then with a corresponding halohydrocarbon ($R_2$'X) in the presence of an alkali at room temperature or under heating conditions, wherein $R_2$' is —$CHR_1Z$, in which $R_1$ and Z are as defined according to claim 1 without Z being $R_2R_3NCH_2CH(OH)$—; or wherein the compound of formula (I-3), (I-3)

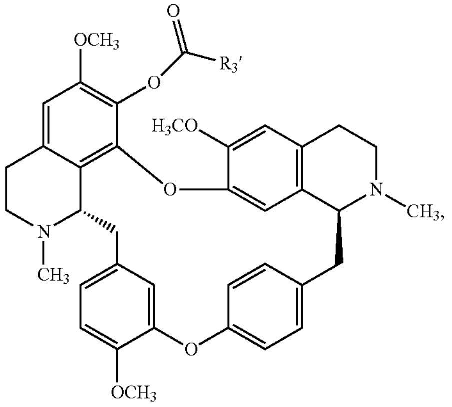

is produced by reacting fangchinoline (FAN) with the corresponding organic acid ($R_3$'$CO_2H$) in the presence of a condensing agent and an alkali at room temperature, wherein $R_3$' is $C_1$-$C_6$ alkyl substituted with a substituent, $C_2$-$C_6$ alkenyl optionally substituted with a substituent, $C_3$-$C_7$ cycloalkyl or cycloalkenyl optionally substituted with a substituent, heterocyclyl optionally substituted with a substituent, or aryl or heteroaryl optionally substituted with a substituent, in which the substituent is as defined according to claim 1.

10. A pharmaceutical composition, comprising the compound or a pharmaceutically acceptable salt thereof according to claim 1 and optionally a pharmaceutically acceptable excipient.

11. A method for treating a subject suffering from cancer, comprising administrating to the subject in need thereof an effective amount of the compound or a pharmaceutically acceptable salt thereof according to claim 1, wherein the cancer is selected from the group consisting of chronic myeloid leukemia, acute myeloid leukemia, acute promyelocytic leukemia, acute lymphocytic leukemia, multiple myeloma, lymphoma, liver cancer, gastric cancer, breast cancer, pancreatic cancer, lung cancer, colorectal cancer, osteosarcoma, human cervical cancer, glioma, nasopharyngeal carcinoma, laryngeal carcinoma, esophageal cancer, and prostate cancer.

12. A compound of formula (I), or a pharmaceutically acceptable salt thereof,

I

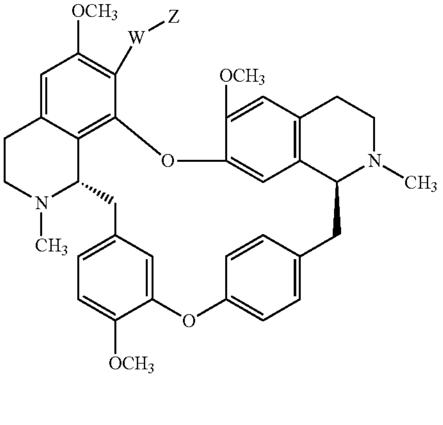

wherein

W is —$OCHR_1$—;

Z is selected from the group consisting of $C_2$-$C_6$ alkenyl optionally substituted with a substituent, $C_3$-$C_7$ cycloalkenyl optionally substituted with a substituent, heterocyclyl optionally substituted with a substituent, aryl or heteroaryl substituted with a substituent, and $R_2R_3NCH_2CH(OH)$—, or Z and $R_1$, together with the carbon atom to which they are attached, form $C_3$-$C_7$ cycloalkyl optionally substituted with a substituent;

$R_1$ is H, or $R_1$ and Z, together with and the carbon atom to which they are attached, form $C_3$-$C_7$ cycloalkyl optionally substituted with a substituent;

$R_2$ and $R_3$ are independently H, $C_1$-$C_6$ alkyl or $C_2$-$C_6$ alkenyl optionally substituted with hydroxyl, $C_1$-$C_6$ alkoxy, halogen, $C_3$-$C_7$ cycloalkyl or cycloalkenyl, aryl or heteroaryl, or $R_2$ and $R_3$, together with the nitrogen atom to which they are attached, form 3-7 membered nitrogen-containing heterocycle; said nitrogen-containing heterocycle optionally comprises an additional heteroatom selected from oxygen, sulfur and nitrogen and is optionally substituted with a substituent;

wherein said substituent is selected from the group consisting of halogen, amino, $C_1$-$C_6$ alkyl amino, di($C_1$-$C_6$ alkyl)amino, nitro, cyano, hydroxyl, $C_1$-$C_6$ alkoxy, $C_1$-$C_6$ haloalkoxy, mercapto and $C_1$-$C_6$ alkylthio; for said aryl, heteroaryl, $C_3$-$C_7$ cycloalkyl or cycloalkenyl, heterocyclyl and nitrogen-containing heterocyclyl, said substituent is also selected from the group consisting of $C_1$-$C_6$ alkyl, hydroxyl $C_1$-$C_6$ alkyl and $C_1$-$C_6$ haloalkyl;

wherein said heteroaryl refers to an aromatic ring group having 1-4 heteroatoms in the ring as ring atom(s), the heteroatom is selected from the group consisting of nitrogen, oxygen and sulfur, and the heteroaryl is a monocyclic heteroaryl having 5-7 ring atoms or a bicyclic heteroaryl having 7-11 ring atoms;

and wherein said heterocyclyl refers to a non-aromatic cyclic group containing 1-4 heteroatoms as ring members, the heteroatom refers to nitrogen, oxygen or sulfur, and the heterocyclyl is a monocyclic heterocyclyl having 4-8 ring atoms or a bicyclic heterocyclyl having 7-11 ring atoms.

13. The compound or a pharmaceutically acceptable salt thereof according to claim 12, wherein the compound is selected from the group consisting of

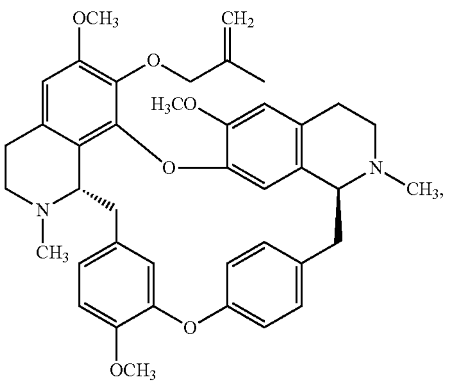

-continued

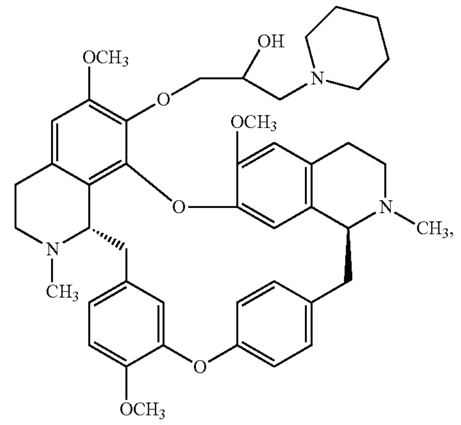

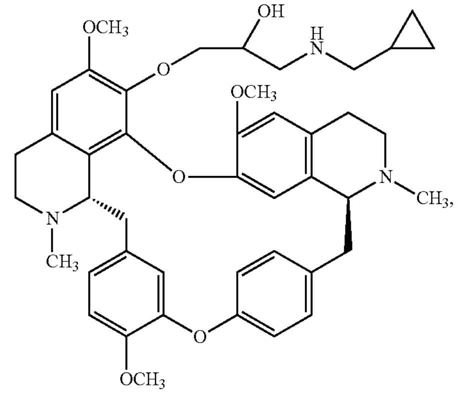

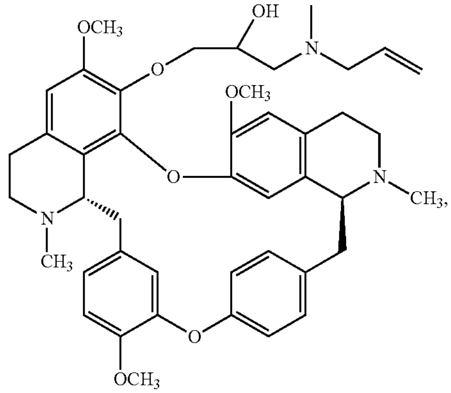

and

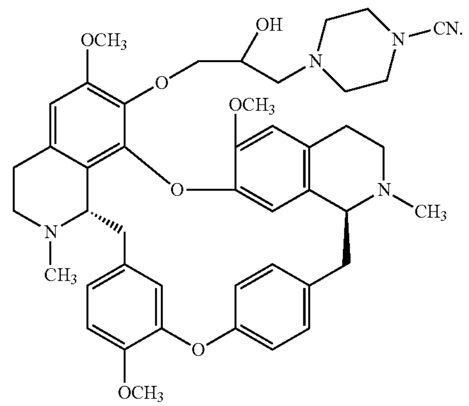 [SMILES: COc1ccc2cc1Oc1ccc(cc1)C[C@H]1c3cc(c(OC)cc3CCN1C)Oc1c(OCC(O)CN3CCN(C#N)CC3)c(OC)cc3c1[C@H](C2)N(C)CC3]

14. A process for preparing a compound of formula (I) according to claim 12, wherein the compound of formula (I-4), (I-4)

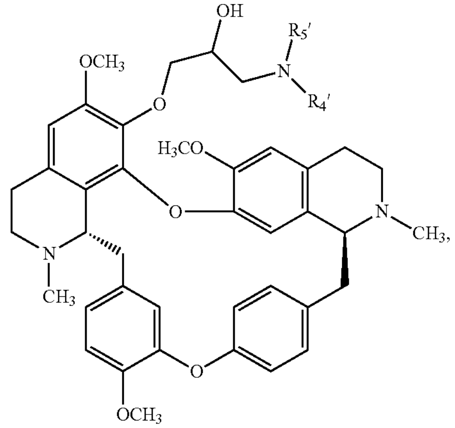

is produced by a two-step reaction: firstly reacting fangchinoline (FAN), (FAN)

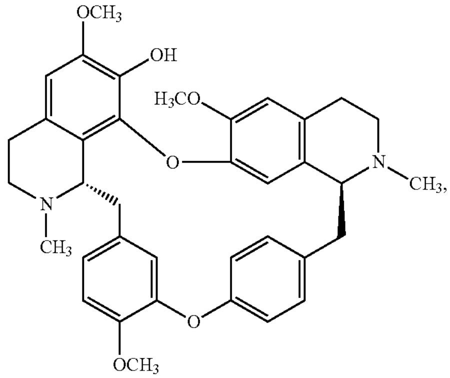

with potassium tert-butoxide and chloromethyl propylene oxide to give an intermediate, and then reacting this intermediate with a corresponding organic amine to give I-4, wherein $R_4$' and $R_5$' are defined as $R_2$ and $R_3$ according to claim 12.

15. A pharmaceutical composition, comprising the compound or a pharmaceutically acceptable salt thereof according to claim 12 and optionally a pharmaceutically acceptable excipient.

16. A method for treating a subject suffering from cancer, comprising administrating to the subject in need thereof an effective amount of the compound or a pharmaceutically acceptable salt thereof according to claim 12, wherein the cancer is selected from the group consisting of chronic myeloid leukemia, acute myeloid leukemia, acute promyelocytic leukemia, acute lymphocytic leukemia, multiple myeloma, lymphoma, liver cancer, gastric cancer, breast cancer, pancreatic cancer, lung cancer, colorectal cancer, osteosarcoma, human cervical cancer, glioma, nasopharyngeal carcinoma, laryngeal carcinoma, esophageal cancer, and prostate cancer.

17. The compound or a pharmaceutically acceptable salt thereof according to claim 12, wherein W is —$OCH_2$—;

Z is selected from the group consisting of $C_2$-$C_6$ alkenyl optionally substituted with a substituent, $C_3$-$C_7$ cycloalkenyl optionally substituted with a substituent, heterocyclyl optionally substituted with a substituent, aryl or heteroaryl substituted with a substituent, and $R_2R_3NCH_2CH(OH)$—;

$R_2$ and $R_3$ are independently H, $C_1$-$C_6$ alkyl or $C_2$-$C_6$ alkenyl optionally substituted with hydroxyl, $C_1$-$C_6$ alkoxy, halogen, $C_3$-$C_7$ cycloalkyl or cycloalkenyl, aryl or heteroaryl, or $R_2$ and $R_3$, together with the nitrogen atom to which they are attached, form 3-7 membered nitrogen-containing heterocycle; said nitrogen-containing heterocycle optionally comprises an additional heteroatom selected from the group consisting of oxygen, sulfur and nitrogen and is optionally substituted with a substituent;

wherein said substituent is selected from the group consisting of halogen, amino, $C_1$-$C_6$ alkyl amino, di($C_1$-$C_6$ alkyl)amino, nitro, cyano, hydroxyl, $C_1$-$C_6$ alkoxy, $C_1$-$C_6$ haloalkoxy, mercapto and $C_1$-$C_6$ alkylthio; for said aryl, heteroaryl, $C_3$-$C_7$ cycloalkyl or cycloalkenyl, heterocyclyl and nitrogen-containing heterocyclyl, said substituent is also selected from the group consisting of $C_1$-$C_6$ alkyl, hydroxyl $C_1$-$C_6$ alkyl and $C_1$-$C_6$ haloalkyl.

18. The compound or a pharmaceutically acceptable salt thereof according to claim 17, wherein Z is aryl or heteroaryl substituted with a substituent;

wherein said substituent is selected from the group consisting of halogen, amino, $C_1$-$C_6$ alkyl amino, di($C_1$-$C_6$alkyl)amino, nitro, cyano, hydroxyl, $C_1$-$C_6$alkoxy, $C_1$-$C_6$ haloalkoxy, mercapto, $C_1$-$C_6$alkylthio, $C_1$-$C_6$ alkyl, hydroxyl $C_1$-$C_6$ alkyl and $C_1$-$C_6$haloalkyl.

19. The compound or a pharmaceutically acceptable salt thereof according to claim 18, wherein Z is phenyl substituted with a substituent selected from the group consisting of halogen, $C_1$-$C_6$ alkyl, $C_1$-$C_6$ halo alkyl, $C_1$-$C_6$alkoxy, hydroxyl $C_1$-$C_6$ alkyl and $C_1$-$C_6$ halo alkyl.

20. The compound or a pharmaceutically acceptable salt thereof according to claim 17, wherein Z is $R_2R_3NCH_2CH(OH)$—;

$R_2$ and $R_3$ are independently H, $C_1$-$C_6$ alkyl or $C_2$-$C_6$ alkenyl optionally substituted with hydroxyl, $C_1$-$C_6$alkoxy, halogen, $C_3$-$C_7$cycloalkyl or cycloalkenyl, aryl or heteroaryl, or $R_2$ and $R_3$, together with the nitrogen atom to which they are attached, form 3-7 membered nitrogen-containing heterocycle; said nitrogen-containing heterocycle optionally comprises an additional heteroatom selected from the group consisting of oxygen, sulfur and nitrogen, and is optionally substituted with a substituent;

wherein said substituent is selected from the group consisting of halogen, amino, $C_1$-$C_6$ alkyl amino, di($C_1$-$C_6$alkyl)amino, nitro, cyano, hydroxyl, $C_1$-$C_6$alkoxy, $C_1$-$C_6$ haloalkoxy, mercapto, $C_1$-$C_6$alkylthio, $C_1$-$C_6$ alkyl, hydroxyl $C_1$-$C_6$ alkyl and $C_1$-$C_6$haloalkyl.

21. The compound or a pharmaceutically acceptable salt thereof according to claim 20, wherein said nitrogen-containing heterocycle is piperidinyl, piperazinyl, morpholinyl, thiazinyl, pyrrolidinyl, oxazolidinyl or thiazolidyl, which are optionally substituted with a substituent selected from the group consisting of halogen, amino, $C_1$-$C_6$ alkyl amino, di($C_1$-$C_6$ alkyl)amino, nitro, cyano, hydroxyl, $C_1$-$C_6$alkoxy, $C_1$-$C_6$ haloalkoxy, mercapto, $C_1$-$C_6$ alkylthio, $C_1$-$C_6$ alkyl, hydroxyl $C_1$-$C_6$ alkyl and $C_1$-$C_6$haloalkyl.

22. The compound or a pharmaceutically acceptable salt thereof according to claim 21, wherein said nitrogen-containing heterocycle is piperidinyl optionally substituted with $C_1$-$C_6$ alkyl, thiazinyl substituted with $C_1$-$C_6$ alkyl, or piperazinyl optionally substituted with N-cyano.

23. The compound or a pharmaceutically acceptable salt thereof according to claim 20, wherein $R_2$ and $R_3$ are independently H, methyl, ethyl, hydroxyethyl, cyclopropylmethyl, allyl, methoxypropyl, or furfuryl.

24. The compound or a pharmaceutically acceptable salt thereof according to claim 17, wherein Z is $C_2$-$C_6$ alkenyl or $C_3$-$C_7$ cycloalkenyl.

25. The compound or a pharmaceutically acceptable salt thereof according to claim 24, wherein Z is vinyl, 1-methylvinyl or cyclopropyl.

26. The compound or a pharmaceutically acceptable salt thereof according to claim 12, wherein W is —$OCHR_1$—, Z and $R_1$, together with the carbon atom to which they are attached, form $C_3$-$C_7$cycloalkyl optionally substituted with a substituent, wherein said substituent is selected from the group consisting of halogen, amino, $C_1$-$C_6$ alkyl amino, di($C_1$-$C_6$alkyl)amino, nitro, cyano, hydroxyl, $C_1$-$C_6$alkoxy, $C_1$-$C_6$ haloalkoxy, mercapto, $C_1$-$C_6$alkylthio, $C_1$-$C_6$ alkyl, hydroxyl $C_1$-$C_6$ alkyl and $C_1$-$C_6$haloalkyl.

27. The compound or a pharmaceutically acceptable salt thereof according to claim 24, wherein Z and $R_1$, together with the carbon atom to which they are attached, form cyclopentyl or cyclohexyl.

* * * * *